(12) United States Patent
Ravindranathan et al.

(10) Patent No.: US 11,823,782 B2
(45) Date of Patent: Nov. 21, 2023

(54) SYSTEMS, METHODS, APPARATUSES, AND COMPUTER PROGRAM PRODUCTS FOR ADMINISTERING PAIN MANAGEMENT SOLUTIONS REMOTELY

(71) Applicant: Optum, Inc., Minnetonka, MN (US)

(72) Inventors: Rama S. Ravindranathan, Edison, NJ (US); Marilyn Lisa Gordon, Cherry Hill, NJ (US); Gregory J. Boss, Saginaw, MI (US)

(73) Assignee: Optum, Inc., Minnetonka, MN (US)

( * ) Notice: Subject to any disclaimer, the term of this patent is extended or adjusted under 35 U.S.C. 154(b) by 822 days.

(21) Appl. No.: 16/807,674

(22) Filed: Mar. 3, 2020

(65) Prior Publication Data

US 2021/0280286 A1    Sep. 9, 2021

(51) Int. Cl.
*A61F 13/00* (2006.01)
*A61M 35/00* (2006.01)
(Continued)

(52) U.S. Cl.
CPC ............ *G16H 20/10* (2018.01); *A61M 35/00* (2013.01); *A61N 1/36021* (2013.01);
(Continued)

(58) Field of Classification Search
CPC ........... A61F 13/00; A61K 9/00; A61K 37/00; A61K 31/70; A61K 31/71; A61K 9/51;
(Continued)

(56) References Cited

U.S. PATENT DOCUMENTS 7,590,449 B2 * 9/2009 Mann .................. A61N 1/36564
607/23
7,883,488 B2 * 2/2011 Shantha ................ A61M 5/427
604/112

(Continued)

FOREIGN PATENT DOCUMENTS

WO    2000/047108 A1    8/2000

OTHER PUBLICATIONS

Maxey, Kyle, Personalized Medicine on a Wearable Patch, Apr. 3, 2014, Engineering.com, 2 pages, https://www.engineering.com/Education/EducationArticles/ArticleID/7416/Personalized-Medicine-on-a-Wearable-Patch.aspx, May 29, 2020.

*Primary Examiner* — Catharine L Anderson
*Assistant Examiner* — Ilya Y Treyger
(74) *Attorney, Agent, or Firm* — Alston & Bird LLP

(57) ABSTRACT

Certain embodiments provide systems, methods, and computer program products that administer pain management treatments remotely, according to a dynamic prescription. In some embodiments, the dynamic prescription provides for changes in a dosage of a medication or electrical stimulation, based for instance upon changes in the patient's pain tolerance level, biological indicators, or behavioral characteristics. In some embodiments, if it is determined that a dosage change is needed, the dosage change can be compared against the dynamic prescription to determine whether the dosage change is permitted within the scope of the dynamic prescription. In some embodiments, if the dosage change is determined to be outside what is permitted by the scope of the dynamic prescription, the updated dosage information can be provided to the patient's physician for authorization of the updated dosage.

20 Claims, 11 Drawing Sheets

(51) Int. Cl.
*G16H 20/10* (2018.01)
*A61N 1/36* (2006.01)
*A61K 9/00* (2006.01)
*A61K 31/70* (2006.01)
*A61K 9/51* (2006.01)

(52) U.S. Cl.
CPC . *A61N 1/36031* (2017.08); *A61M 2205/3303* (2013.01); *A61M 2230/00* (2013.01); *A61M 2230/06* (2013.01); *A61M 2230/30* (2013.01); *A61M 2230/42* (2013.01); *A61M 2230/50* (2013.01); *A61M 2230/62* (2013.01); *A61M 2230/63* (2013.01)

(58) Field of Classification Search
CPC ........ G16H 20/10; G16H 80/00; G16H 40/67; A61M 35/00; A61M 2205/3303; A61M 2230/00; A61M 2230/06; A61M 2230/42; A61M 2230/50; A61M 2230/62; A61M 2230/63; A61N 1/36021; A61N 1/36031; A61N 1/0492; A61N 1/0529; A61N 1/0551
See application file for complete search history.

(56) References Cited

U.S. PATENT DOCUMENTS

| | | |
|---|---|---|
| 8,874,233 B2 | 10/2014 | McLaughlin et al. |
| 2006/0154642 A1 | 7/2006 | Scannell, Jr. |
| 2014/0052465 A1 | 2/2014 | Madan et al. |
| 2014/0100829 A1 | 4/2014 | Mould |
| 2014/0276549 A1 | 9/2014 | Osorio |
| 2016/0082262 A1 | 3/2016 | Parramon et al. |
| 2018/0070875 A1 | 3/2018 | Kshetrapal |

\* cited by examiner

SYSTEMS, METHODS, APPARATUSES, AND COMPUTER PROGRAM PRODUCTS FOR ADMINISTERING PAIN MANAGEMENT SOLUTIONS REMOTELY

BACKGROUND

In the field of pain management, medications such as opioids have conventionally been administered, typically in pill form, to patients experiencing pain. However, opioid addiction is a growing issue, which has led to the development of alternative approaches for pain management. For example, neuromodulation has gained popularity in recent years as an alternative pain management treatment, in addition to other alternative treatments such as physical therapy, Ayurveda and other similar treatments. However, with neuromodulation, as with medications in, e.g., pill form, the administered dosage is static and, if a patient's symptoms and/or pain management needs change after the physician provides the initial prescription or initially configures the device for a particular dosage, patients need to return to their physician for dosage adjustments or adjustments of the neuromodulation device. This process causes lot of hassle for patients and physicians alike, leads to a lag in prescriptions changes in response to symptom or pain tolerance changes, and may exacerbate the opioid addiction problem.

BRIEF SUMMARY

In general, embodiments of the present invention provide methods, apparatus, systems, computing devices, computing entities, and/or the like for administering pain management solutions remotely. Certain embodiments utilize systems, methods, and computer program products that provide pain management remotely, according to a dynamic prescription. In some embodiments, the dynamic prescription provides for changes in a dosage of a medication or electrical stimulation, based for instance upon changes in the patient's pain tolerance level, biological indicators, or behavioral characteristics. In some embodiments, if it is determined that a dosage change is needed, the dosage change can be compared against the dynamic prescription to determine whether the dosage change is permitted within the scope of the situation and patient's conditions which include socio economic and other environmental areas. In some embodiments, if the dosage change is determined to be outside what is permitted by the scope of the dynamic prescription, the updated dosage information can be provided to the patient's physician for authorization of the updated dosage. In some embodiments, the patient's pain tolerance level, biological indicators, or behavioral characteristics may be provided to the patient's physician along with the updated dosage information in order for the physician to determine if the updated dosage is warranted.

In accordance with a first aspect, a system can be provided for carrying out dynamic pain management remotely. In some embodiments, the system can comprise: an epidermal treatment device configured to be placed in operable contact with a patient's epidermis and provide an initial dosage of a pain management treatment to the patient's epidermis according to an initial prescription; and a prescription management unit in wireless communication with the transdermal patch, the prescription management unit configured to: receive patient behavior information, determine, based at least upon the patient behavior information, the patient's current pain tolerance, and determine, based on at least the patient's current pain tolerance, an updated prescription comprising updated dosage information for pain management treatment. In some embodiments, the prescription management unit is further configured to provide the updated prescription to the epidermal treatment device, wherein the epidermal treatment device is further configured, upon receiving the updated prescription from the prescription management unit, to provide an updated dosage different from the initial dosage of the pain management treatment to the patient's epidermis according to the updated prescription. In some embodiments, the system can further comprise: a patient monitoring unit configured to monitor one or more biometric characteristics of the patient, generate the patient behavior information, and provide the patient behavior information to the prescription management unit. In some embodiments, the patient monitoring unit can be or be hosted on or provided by a user device or a control device. In some embodiments, the patient monitoring unit, user device, and/or control device can comprise or be in operable communication with one or more devices configured to detect, measure, determine, monitor, evaluate, sense, calculate, estimate, or otherwise provide for generation or provision of the patient behavior information and/or the one or more biometric characteristics of the patient. In some embodiments, the patient monitoring unit, user device, and/ or control device may comprise or be in operable communication with one or more cameras configured to capture images or video of a patient, a portion of the patient, a face of the patient, a portion of the face of the patient, and/or the like. In some embodiments, the patient monitoring unit, user device, and/or control device may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the patient monitoring unit, user device, and/or control device may comprise or be in operable communication with one or more microphones configured to capture audio associated with a patient, vocal audio of the patient, non-verbal sounds associated with the patient, and/ or the like. In some embodiments, the patient monitoring unit, user device, and/or control device may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the patient monitoring unit, user device, and/ or control device may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the patient monitoring unit, user device, and/ or control device may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, an apparatus comprising one or more processors and one or more memory storing computer program instructions for storing and processing such information data and/or the like. In some embodiments, such as when one of the patient monitoring unit, user device, or control unit comprises a camera and is configured to capture images or video of a patient's face, the device or system can further comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time. In some embodiments, the one or more biometric characteristics are selected from among posture, gait, speech patterns, eye movements, heart rate, blood pressure, core temperature, epidermal temperature, respiration rate, epidermal perspiration rate, facial expressions, changes in facial expressions, and Prkachin and Solomon Pain Intensity (PSPI) indicators. In some embodiments, the patient behavior information is generated based at least upon the one or more biometric characteristics and at least one of: manual inputs from the patient regarding the patient's current pain level, the patient's medical records, the dosage information from the initial prescription, and the patient's historical prescription information. In some embodiments, the system can further comprise: a prescription authorization unit in wireless communication with the prescription management unit, the prescription management unit being further configured to communicate wirelessly to the prescription authorization unit at least one of: the patient behavior information, the patient's pain tolerance, the updated prescription, and the updated dosage information for pain management treatment. In some embodiments, the prescription authorization unit can be configured to: compare the updated prescription to a dynamic prescription comprising a dynamic preauthorized dosage range, and determine whether the updated dosage is within the dynamic preauthorized dosage range. In some embodiments, the prescription authorization unit can be further configured to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription, receive from the medical provider a response regarding the updated prescription, and provide to the prescription management unit one of a message confirming receipt of the updated prescription, a message authorizing the updated prescription, a message amending the updated prescription, a message replacing the updated prescription with a further updated prescription, and a message rejecting the updated prescription; or, in an instance in which the updated dosage information is not within the dynamic preauthorized range and the prescription authorization unit does not have instructions to solicit manual authorization from the medical provider, provide to the prescription management unit a message rejecting the updated prescription. In some embodiments, the epidermal treatment device comprises one or more of a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, and a intrathecal drug delivery device.

In accordance with a second aspect, a method is provided. In one embodiment, the method comprises: disposing a pain management device onto a portion of a patient's epidermis, the pain management device configured to provide an initial dosage of a pain management treatment, according to an initial prescription, via the patient's epidermis; monitoring patient behavior to determine a current pain tolerance for the patient; and determining, based at least on the current pain tolerance, an updated prescription for an updated dosage different from the initial dosage of the pain management treatment. In some embodiments, the method can further comprise communicating with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the method can further comprise, in an instance in which the updated dosage information is within the dynamic preauthorized range, providing to the prescription management unit a message authorizing the updated prescription, in an instance in which the updated dosage information is not within the dynamic preauthorized range and the prescription authorization unit has instructions to solicit manual authorization from a medical provider, displaying for the medical provider the updated prescription, receiving from the medical provider a response regarding the updated prescription, and providing to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, providing to the prescription management unit a message rejecting the updated prescription.

In accordance with a third aspect, a computer program product is provided. The computer program product may comprise at least one computer-readable storage medium having computer-readable program code portions stored therein, the computer-readable program code portions comprising executable portions configured to: communicate with a pain management device disposed on a portion of a patient's epidermis, the pain management device configured to provide an initial dosage of a pain management treatment, according to an initial prescription, via the patient's epidermis; monitor patient behavior to determine a current pain tolerance for the patient and determine, based at least on the current pain tolerance, an updated prescription for an updated dosage different from the initial dosage of the pain management treatment. In some embodiments, the computer-readable program code portions can further comprise executable portions configured to: communicate with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the computer-readable program code portions can further comprise executable portions configured to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription; receive from the medical provider a response regarding the updated prescription; and provide to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, provide to the prescription management unit a message rejecting the updated prescription.

In accordance with a fourth aspect, an apparatus comprising at least one processor and at least one memory including computer program code is provided. In one embodiment, the at least one memory and the computer program code may be configured to, with the processor, cause the apparatus to: communicate with a pain management device disposed on a portion of a patient's epidermis, the pain management device configured to provide an initial dosage of a pain management treatment, according to an initial prescription, via the patient's epidermis; monitor patient behavior to determine a current pain tolerance for the patient and determine, based at least on the current pain tolerance, an updated prescription for an updated dosage different from the initial dosage of the pain management treatment. In some embodiments, the at least one memory and the computer program code may be configured to, with the processor, cause the apparatus to: communicate with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the at least one memory and the computer program code may be configured to, with the processor, cause the apparatus to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription; receive from the medical provider a response regarding the updated prescription; and provide to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, provide to the prescription management unit a message rejecting the updated prescription.

In accordance with a fourth aspect, an apparatus can comprise at least one processor and at least one memory including computer program code. In some embodiments, the apparatus can be configured to carry out dynamic pain management remotely. In some embodiments, the apparatus can comprise: an epidermal treatment device configured to be placed in operable contact with a patient's epidermis and provide an initial dosage of a pain management treatment to the patient's epidermis according to an initial prescription, wherein the apparatus is configured to: receive patient behavior information, determine, based at least upon the patient behavior information, the patient's current pain tolerance, and determine, based on at least the patient's current pain tolerance, an updated dosage different from the initial dosage, according to an updated prescription, for pain management treatment. In some embodiments, the apparatus can be further configured to: provide, via the epidermal treatment device, an updated dosage different from the initial dosage of the pain management treatment to the patient's epidermis according to the updated prescription. In some embodiments, the apparatus is further configured to receive the patient behavior information from a patient monitoring unit configured to monitor one or more biometric characteristics of the patient and generate the patient behavior information. In some embodiments, the apparatus can comprise or be in operable communication with one or more devices configured to detect, measure, determine, monitor, evaluate, sense, calculate, estimate, or otherwise provide for generation or provision of the patient behavior information and/or the one or more biometric characteristics of the patient. In some embodiments, the apparatus may comprise or be in operable communication with one or more cameras configured to capture images or video of a patient, a portion of the patient, a face of the patient, a portion of the face of the patient, and/or the like. In some embodiments, the apparatus may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the apparatus may comprise or be in operable communication with one or more microphones configured to capture audio associated with a patient, vocal audio of the patient, non-verbal sounds associated with the patient, and/or the like. In some embodiments, the apparatus may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the apparatus may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the apparatus may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, one or more processors and one or more memory storing computer program instructions for storing and processing such information data and/or the like. In some embodiments, such as when the apparatus comprises a camera and is configured to capture images or video of a patient's face, the apparatus can comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time. In some embodiments, the one or more biometric characteristics are selected from among posture, gait, speech patterns, eye movements, heart rate, blood pressure, core temperature, epidermal temperature, respiration rate, epidermal perspiration rate, facial expressions, changes in facial expressions, and Prkachin and Solomon Pain Intensity (PSPI) indicators. In some embodiments, the patient behavior information is generated based at least upon the one or more biometric characteristics and at least one of: manual inputs from the patient regarding the patient's current pain level, the patient's medical records, the dosage information from the initial prescription, and the patient's historical prescription information. In some embodiments, the apparatus can be further configured to: communicate wirelessly, to a prescription authorization unit, at least one of the patient behavior information, the patient's pain tolerance, the updated prescription, and the updated dosage information for pain management treatment. In some embodiments, the apparatus can be further configured to: receive, from the prescription authorization unit, one or more of a message confirming receipt of the updated prescription, a message approving the updated prescription, a message amending the updated prescription, a message replacing the updated prescription with a further updated prescription, and a message rejecting the updated prescription. In some embodiments, the epidermal treatment device comprises one or more of a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, and a intrathecal drug delivery device.

In accordance with a fifth aspect, there is provided a system for administering a pain management treatment remotely. The system can comprise an epidermal treatment device configured to store an initial prescription and operable to provide a pain management treatment to a patient (e.g., a user). In some embodiments, the epidermal treatment device can be coupled to the user, abutted to the user, embedded in the user's skin, implanted in the user, removably coupled to the user, or in any other manner caused to provide a pain management treatment to the patient when the patient is not with their provider (e.g., configured to administer the pain management treatment remotely). The system can further comprise a patient monitoring unit configured to iteratively, discretely, or continuously, observe the user and measure, monitor, estimate, calculate, interpolate, or otherwise determine biometric characteristics about the user. The system can further comprise a prescription management unit that is in operable communication with the patient monitoring unit, the prescription management unit being configured to review the user's biometric characteristics and to determine whether the initial prescription is sufficient to reduce or eliminate the user's pain based on the user's pain tolerance or pain threshold, which is determined based on at least the biometric characteristics. The prescription management unit can also be configured to determine when a change in the initial prescription dosage is necessary based on changes in the user's biometric characteristics. In an instance in which the prescription management unit determines that a change in the dosage of the pain management treatment is needed, based at least upon the user's biometric characteristics, the prescription management unit can a) determine that the change in dosage of the pain management treatment is automatically approved based upon some initial instructions regarding a change tolerance or margin about the initial dosage that the prescription management unit is instructed to automatically authorize, b) determine that the dosage change is an errant dosage change based upon the magnitude of the change relative to the dosage of the initial prescription and request further biometric characteristics be provided from the patient monitoring unit, or c) determine that the change in dosage of pain management treatment is needed but that it falls outside of any provided change tolerance or margin relative to the initial dosage, and request authorization for the updated dosage from a provider or a provider device. With regard to option c) from above, the system can further comprise a prescription authorization unit configured to store or receive a dynamic prescription associated with the user and with the particular pain management treatment. The dynamic prescription can be developed based upon provider-provided and/or patient-provided data such as electronic health records, individual health records, international or domestic health regulations, provider management systems, patient preferences, the patient's insurance details, the patient's historical biometric data, historical biological data, historical medical records, and the like. The dynamic prescription can comprise a set of 'if/then' elements or the like that the prescription authorization unit is configured to answer in a particular order. In some embodiments, the dynamic prescription can include an initial question or initial set of questions that relate, for instance, to a change in the patient's pain tolerance or pain threshold. In some embodiments, the dynamic prescription can include subsequent questions or set of questions that relate, for instance, to a provider-provide limit on the dosage of the pain management treatment that considers the patient's biometric, biological, medical, or other characteristics or data (e.g., the patient's heart rate, blood pressure, gait, or the like). In some embodiments, the dynamic prescription can also include a question or a set of questions related to domestic or international regulations related to what and how much pain management treatments can be administered/changed remotely, absolute or relative dosage limits, and/or the like. In some embodiments, the dynamic prescription can include a question or a set of questions related to past changes in the dosage, the rate and magnitude of such changes, the remaining supply of pain medication (when applicable), and/or the like. Said otherwise, the dynamic prescription, instead of providing a static dosage, can provide a dosage range that changes in response to changes in a patient's pain tolerance or pain threshold, accounting for medical or legal limits placed on dosage changes that are specific to the pain management treatment, jurisdiction, provider, application type, patient, provider, and/or the like. The dynamic prescription can be pre-authorized by the provider. In some embodiments, when the prescription management unit determines that the change in dosage of pain management treatment is needed but that it falls outside of any provided change tolerance or margin relative to the initial dosage, the prescription management unit may transmit a request for authorization of the updated dosage of the updated prescription to the prescription authorization unit. The prescription authorization unit can then review the request for the updated dosage of the updated prescription, e.g., by answering the questions related to the dynamic prescription to determine if the provider-pre-authorized dynamic prescription authorizes the updated dosage for the patient, and then a) automatically provides authorization for the updated prescription to the prescription management unit, b) automatically rejects the updated prescription (e.g., when the dosage change is suspected to be in error, when the dosage change would contravene a law, and/or the like), or c) requests approval for the updated prescription from the provider. In some embodiments, the prescription authorization unit can cause a notification, alert, message, request, or the like to be pushed to, displayed on, sent to, or otherwise provided to a provider device such as a computer, beeper, mobile phone, smart phone, tablet, or the like. The provider can then review the updated prescription and can instruct the prescription authorization unit to either allow or disallow the updated prescription, can mark the updated prescription as being a suspected errant request, can communicate with the patient/user to provide telemedical care or request that the patient/user visits the provider's office, amend the dynamic prescription based upon the updated prescription request, and/or the like. In an instance in which the prescription authorization unit or prescription management unit automatically authorizes the updated prescription, or in an instance in which the provider manually authorizes the updated prescription, the prescription management unit can communicate with either the patient monitoring unit or the epidermal treatment device to provide the updated prescription along with authorization for the epidermal treatment device to administer the pain management treatment to the user according to the updated prescription. The epidermal treatment device can then replace the initial prescription with the updated prescription and comply with the specific dosage/timing requirements of the updated prescription in administering the pain management treatment to the user.

In accordance with a sixth aspect, there is provided an apparatus for accurately determining a pain tolerance or a pain threshold for a patient remotely. The apparatus can comprise one or more processors and one or more memory storing computer program code. The apparatus can be configured to iteratively, discretely, or continuously, observe the user and measure, monitor, estimate, calculate, interpolate, or otherwise determine biometric, biological, medical, or other suitable characteristics about the patient. The apparatus can determine the patient's current pain tolerance or pain threshold based on at least the biometric, biological, medical, or other suitable characteristics. In some embodiments, the apparatus can comprise or be in operable communication with one or more devices configured to detect, measure, determine, monitor, evaluate, sense, calculate, estimate, or otherwise provide for generation or provision of the patient behavior information and/or the one or more biometric characteristics of the patient. In some embodiments, the apparatus may comprise or be in operable communication with one or more cameras configured to capture images or video of a patient, a portion of the patient, a face of the patient, a portion of the face of the patient, and/or the like. In some embodiments, the apparatus may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the apparatus may comprise or be in operable communication with one or more microphones configured to capture audio associated with a patient, vocal audio of the patient, non-verbal sounds associated with the patient, and/or the like. In some embodiments, the apparatus may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the apparatus may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the apparatus may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, one or more processors and one or more memory storing computer program instructions for storing and processing such information data and/or the like. In some embodiments, such as when the apparatus comprises a camera and is configured to capture images or video of a patient's face, the apparatus can comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time. The apparatus can comprise a display and a user interface configured to allow for the patient to interact with an application, program, browser, or the like stored on and/or hosted by the apparatus. In some embodiments, the patient may provide feedback about their current pain tolerance or pain threshold at certain intervals, e.g., regularly, irregularly, when they perceive a change in their pain tolerance or pain threshold, and/or the like. In some embodiments, the apparatus can include one or more sensors, one or more camera devices, one or more keyboards, one or more touchscreens or other such interactive input devices, and/or the like. In some embodiments, the apparatus can include one or more activity monitoring devices or healthcare monitoring devices, such as but not limited to: a gyroscope, a magnetometer, an accelerometer (e.g., a 3-axis accelerometer), a geospatial positioning system, a barometer, an altimeter, a step counter, a blood pressure monitor, a heart rate monitor, a respiration monitor, ambient pressure sensor, ambient temperature sensor, ambient oxygen sensor, an electrocardiogram device, an electroencephalogram device, skin temperature sensor, a myocardial sensor, a blood oxygen sensor, a elastomeric plethysmography (EP) device (e.g., one or more piezoelectric sensors on an elastic band for elastomeric plethysmography via current variation), an impedance plethysmography (IP) device, a respiratory inductive plethysmography (RIP) device, a photoplethysmography (PPG) device configured to measure blood oxygen saturation using pulse oximetry principles by measuring two adjacent peaks in a blood vessel variation waveform, a continuous glucose monitoring (CGM) device, or the like. In some embodiments, the apparatus can include one or more speakers and/or one or more microphones. In some embodiments, the apparatus is configured to monitor, measure, calculate, estimate, sense, observe, interpret, derive, or otherwise determine one or more biometric, biological, medical, or movement characteristics of the patient and the chance over time thereof, such as but not limited to: facial feature, facial expressions, facial micro-expressions, gait, heart rate, heart rate variability, heart rate irregularity, incidents of a fall experienced by the patient, step count, step pace, blood pressure, respiration rate, eye movements, blink rate, pupil dilation, vocal/speech pattern, speech pace, incidents of slurred speech, posture, perspiration rate, breathing rate, sudden reduction or loss of hearing (e.g., if a patient suddenly increases the speaker volume on the apparatus when interacting with the apparatus), dermal and subdermal perfusion rates, time spent sitting versus standing, limb and trunk movement and range of motion, sleep duration and sleep type patterns, combinations thereof, and/or the like. For instance, the apparatus can capture a patient's facial expressions when they are using the device, e.g., by using the front facing camera on a smart phone, and implement a facial action coding system (FACS) in conjunction with Prkachin Solomon Pain Intensity (PSPI) analysis to track pain tolerance or pain threshold changes in the patient. The apparatus can use an algorithm, neural network, machine learning model, and/or the like to determine changes in the patient's pain tolerance or pain threshold.

In accordance with a seventh aspect, there is provided a method for preparing a dynamic prescription of a pain management treatment for a patient. In some embodiment, the method can comprise determining the internet-of-things (IoT) devices and sensors available for a patient and the device and sensor boundaries with respect to particular biological indicators or characteristics. The method can further comprise establishing the patient's current pain threshold/pain tolerance and associating the patient's current pain threshold/pain tolerance with the patient's particular biological indicators or characteristics. The method can further comprise determining a current dosage of a pain management treatment being administered to the patient and associating the current dosage of the pain management treatment with the patient's current pain threshold/pain tolerance and the patient's particular biological indicators or characteristics. The method can further comprise receiving, from a provider, an outside dosage range indicating a magnitude of increase of the dosage and a magnitude of decrease of the dosage that are allowed for the patient. The method can further comprise receiving, from the provider, a set of conditions in which the current dosage of the pain management treatment can be changed, within the outside dosage range. As an initial non-limiting example, the provider may indicate that if the patient's pain tolerance increases to above 9/10 AND the patient belongs to a certain demographic area AND if the patient's age is within a particular age range, then the current dosage can be increased to an updated dosage higher than the current dosage for a particular time period, e.g., before re-analyzing patient pain tolerance/pain threshold or reverting back to the current dosage lower than the updated dosage. As a subsequent non-limiting example, the provider may indicate that if the patients pain tolerance/pain threshold reduces by more than a threshold reduction in pain tolerance/pain threshold AND the patient belongs to a certain demographic area OR if a particular biological indicator is within a predetermined range considered to be suitable for a reduction in dosage, then the current dosage can be decreased to an updated dosage lower than the current dosage for a particular time period, e.g., before re-analyzing patient pain tolerance/pain threshold or reverting back to the current dosage higher than the updated dosage. As a further non-limiting example, the patient may have a wearable device that sends a signal to a provider management system; for example, a cardiology patient taking statins that is determined to be involved in excessive/out-of-normal physical activity, causing a reduction in blood sugar level, which may necessitate a reduction in the dosage of a remotely administered diabetes medication for a particular time period. As yet another non-limiting example, for an oncology patient, to whom a medication is being administered remotely according to any of the processes or methods described herein, a provider may code a dynamic prescription for the oncology patient that indicates, if the oncology patient is exposed to conditions that are not optimal in view of their medical condition and medication being administered AND/OR if the patient is in a particular demographic group (e.g., a particular sex, race, nationality, geographic location, employment type, or any other suitable group of patients) AND/OR if the patient has an age that is within a particular predetermined age range AND/OR if the patient received their last oncology treatment (e.g., radiation therapy, chemotherapy, and/or the like) within a predetermined window preceding the date and time of analysis, then the dynamic prescription can automatically instruct the patient, the provider, the patient's remote pain management treatment administration device (e.g., transdermal patch, neuromodulation device, and/or the like) to increase their dosage of the pain management treatment for a predetermined time period. In some embodiments, in order for a provider to "code" the dynamic prescription via digital means within a provider management system, there may be an "INPUT" which needs to be "ANALYZED" before coding the prescription. For example, an "INPUT" may include without limitation one or more of (a) information related to the sensors or IoT devices that the patient has registered and/or that are in communication with the apparatus or system carrying out the method of establishing the dynamic prescription, (b) capabilities and configurations for the various sensors or IoT devices, either derived from the respective sensor/IoT device, culled from the above-mentioned information, or provided by or retrieved from a third party, (c) a summary of edge computing capabilities for each IoT device, (d) capabilities and configurations for each "coordinating device," such as a smart watch, smart home sensor, vehicle sensor, or the like, that coordinates multiple IoT devices, (e) hierarchy of sensors/IoT devices with regard to channels of communication and the configurations required for data collation and transmission from each of these devices, (f) information related to the interoperability of the various sensors/IoT devices the patient has registered, (g) information related to alternative hierarchies or channels of communication if one or more of the sensors/IoT devices that the patient has registered becomes unreachable or is suspected of being corrupted or providing erroneous data, and/or (h) other suitable information helpful or necessary for the establishment of a stable channel of communication between and within the network and the sensors/IoT devices such that the dynamic prescription can be generated and/or updated based upon inputs from the provider as well as feedback and data provided by the patient and the various sensors/IoT devices. The method for initial coding of the dynamic prescription, in addition to or alternative to the approach and process elements described above, can include presenting the provider with the available "INPUTS," allowing the provider to choose the appropriate collection of sensors/IoT devices that are appropriate for taking into account with regard to the dynamic prescription. The provider can then indicate or code in the dynamic prescription (which may for instance be carried out by selecting among a drop-down list or conducting a search) the appropriate biological indicators, patient movement data, healthcare metrics, and/or environmental data that should be considered from among the data received from the collection of approved sensors/IoT devices the patient has registered. The provider can then identify, for each sensor or IoT device and/or for each type of feedback or data, the expected range or value, optionally one or more secondary indicators or considerations that should be considered in such an instance, and a dosage change that should be carried out in such an instance. For example, for a patient's heart rate monitor, the provider can code a particular heart rate range that is expected for the patient, such that when the heart rate monitor returns a heart rate outside the provider-indicated expected range of heart rates, the dynamic prescription can increase or decrease the dosage based on such an indication. When coding the dynamic prescription, the provider may select a particular frequency or a particular time frame and iteration count for any or all of the analyses being done remotely to determine the patient's pain tolerance or pain threshold, and/or can indicate how the dosage should change based upon changes in the respective analyses. The provider may also indicate the duration of pain management treatment and/or can indicate one or more stages of pain management treatment (e.g., through a staged weaning period). When coding the dynamic prescription, the provider may select a particular activity or group of activities to indicate how the prescription changes based on a particular input, such as information related to the initial cause of pain, the intensiveness of any preceding surgeries or inpatient/outpatient treatments, how many calories the patient has consumed, the number of stiches the patient received following a surgery, or any other suitable input. When coding the dynamic prescription, the provider may select one or more user contexts, such as the demographic information of the patient, to consider when dynamically changing the prescription. When coding the dynamic prescription, the provider may select one or more environmental conditions or changes to consider when dynamically changing the prescription, such environmental conditions or changes including but not limited to exposure to contaminants or harsh environmental conditions, the frequency and/or type of human interaction the patient has (e.g., by tracking emails, SMS texts, phone calls, or the like for a period of time following a surgery), the patient's social media accounts and their interactions with others on these social media platforms, application programming interface (API) calls to the weather system or a third-party weather service, temperature sensor readings, barometric pressure sensor readings, patient activity/motion data, and/or the like. When coding the dynamic prescription, the provider may select a prescription renewal time, e.g., by analyzing the consumption rate of the drug, and authorize the dynamic prescription and/or associated machine learning algorithm or artificial intelligence program carrying out the dynamic prescription to suggest changes or pre-authorize changes only at particular times or with a consideration for the remaining stock of a drug that the patient has on hand. In some embodiments, when the dynamic prescription is updated and/or when their effective dosage is changed according to the dynamic prescription, the patient may be notified through push notification from an application, email, phone call, SMS text message, or the like regarding the change in their prescription or effective dosage. In some embodiments, when the dynamic prescription is updated and/or when their effective dosage is changed according to the dynamic prescription, the patient may be asked to authorize the change in their prescription or effective dosage. In some embodiments, when the dynamic prescription is updated and/or when their effective dosage is changed according to the dynamic prescription, the patient may be notified regarding the change in their prescription or effective dosage and given an opportunity to temporarily stop the change in their prescription or effective dosage until the provider has reviewed the change and has authorized the change. In some embodiments, the patient may be notified regarding the change in their prescription or effective dosage only when the dynamic prescription and/or associated machine learning algorithm or artificial intelligence program carrying out the dynamic prescription determines that the calculated necessary dosage change is outside the range preauthorized under the dynamic prescription, elevated the request for a dosage change to the provider, and the provider has authorized a change not only to the dosage but also to the dynamic prescription. In some embodiments, the dynamic prescription and/or associated machine learning algorithm or artificial intelligence program carrying out the dynamic prescription can track and/or request updates from the patient's sensors/IoT devices regarding the quantity of a remaining stock of the patient's medication. In some embodiments, in an instance in which the dynamic prescription and/or associated machine learning algorithm or artificial intelligence program carrying out the dynamic prescription determine that a change in the dosage will unduly diminish the quantity of the remaining stock of the patient's medication, and/or will result in a depletion of the patient's medication before such a time as the patient is scheduled (or legally allowed) to replenish their stock of the medication, can take these competing challenges and interests into account when determining a necessary change in the dosage of the patient's medication and/or can disallow changes to the dosage administered in order to maintain sufficient stock so that the patient does not run out of their medication before they receive a replenishing supply. In some embodiments, the dynamic prescription and/or associated machine learning algorithm or artificial intelligence program carrying out the dynamic prescription, upon determining that the patient's stock of a medication is low or that a change made to their dosage will result in a more rapid diminishment of the patient's stock of the medication, can provide an alert to the provider such that the provider can coordinate providing the patient with a replenishing supply of their medication, amend the patient's plan of care with regard to the time horizon for administering the drug, contravene the dosage change, and/or contact the patient for follow-up telemedical care.

BRIEF DESCRIPTION OF THE DRAWINGS

Figure 1A:
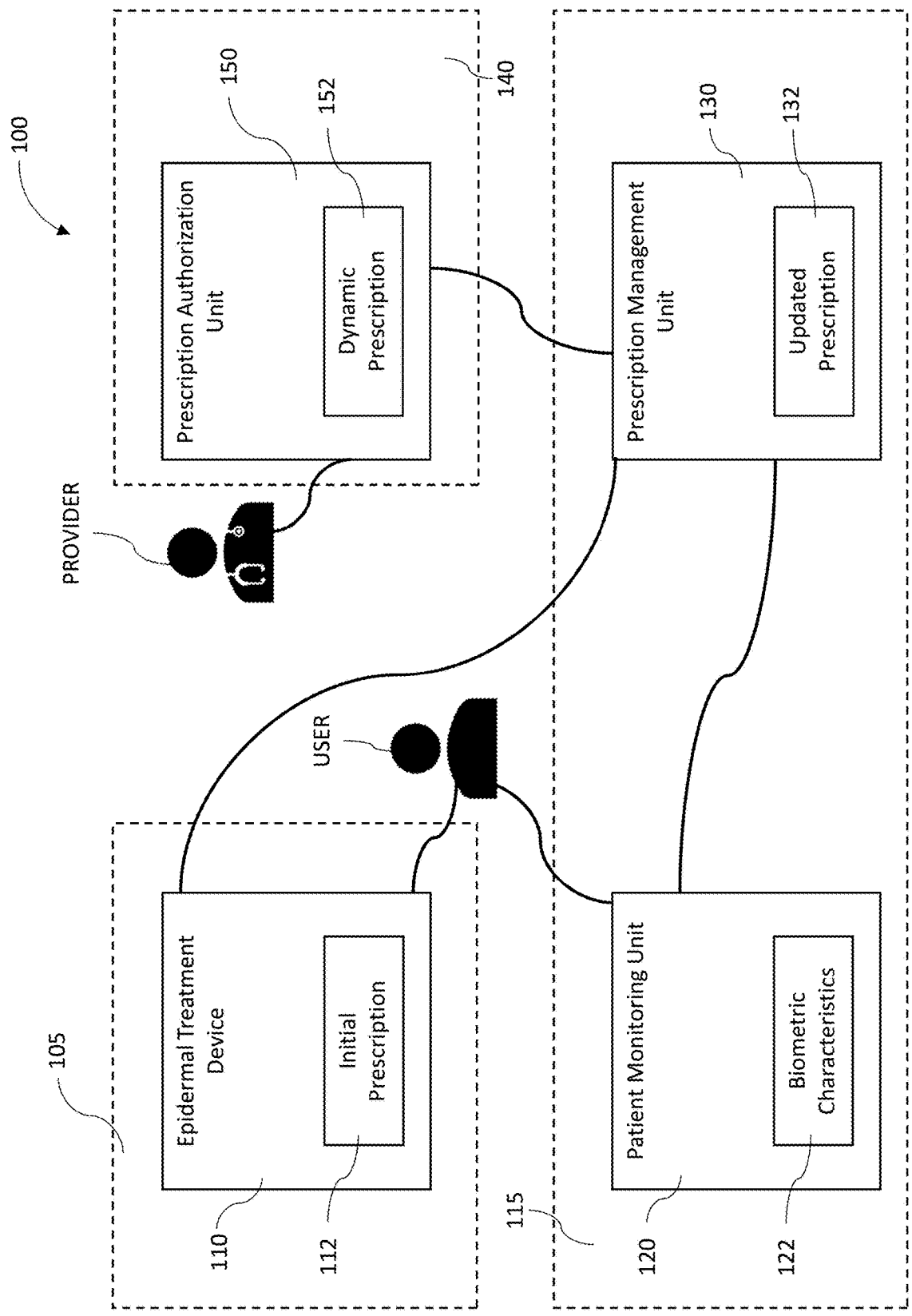
Figure 1B:
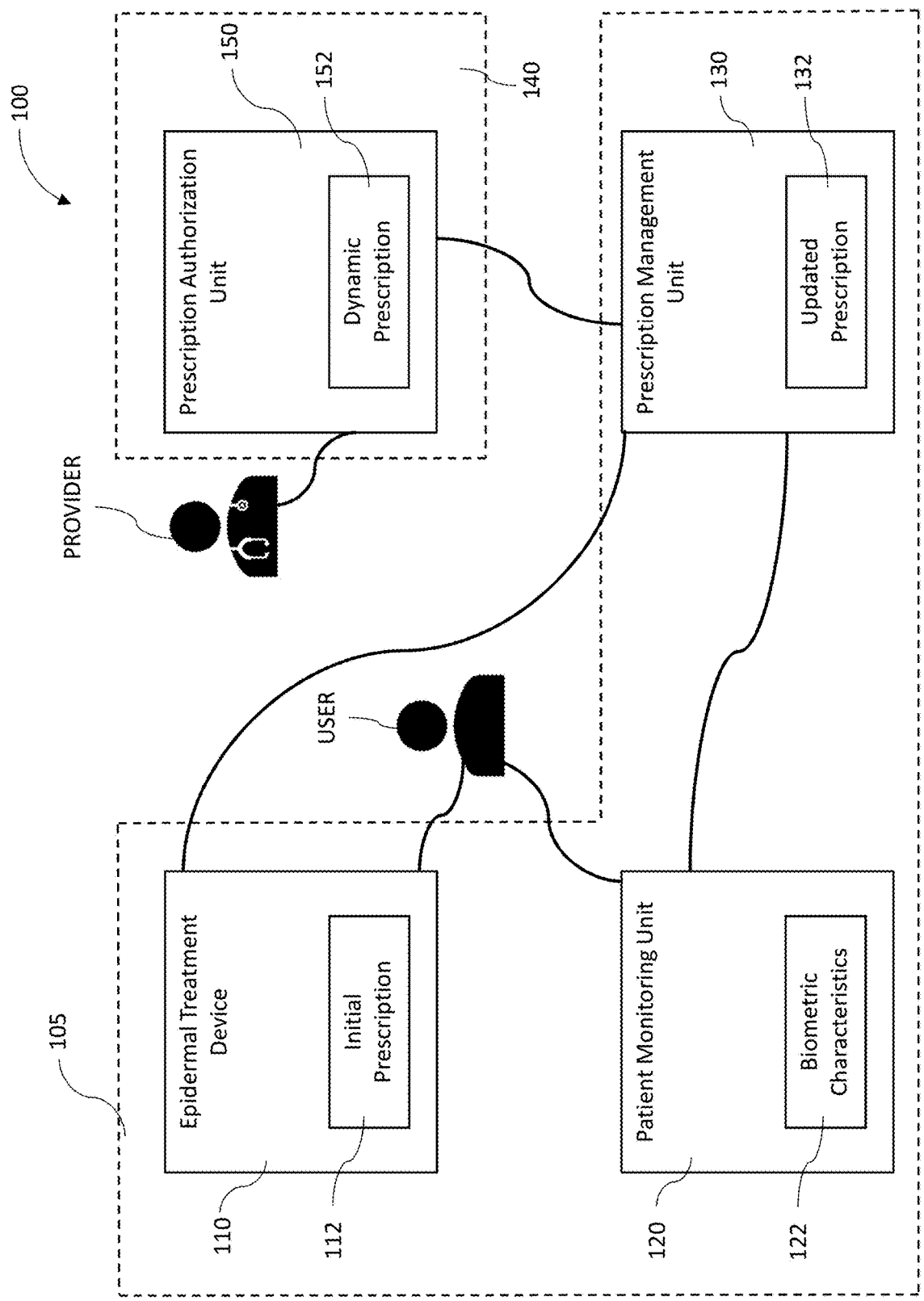
Figure 1C:
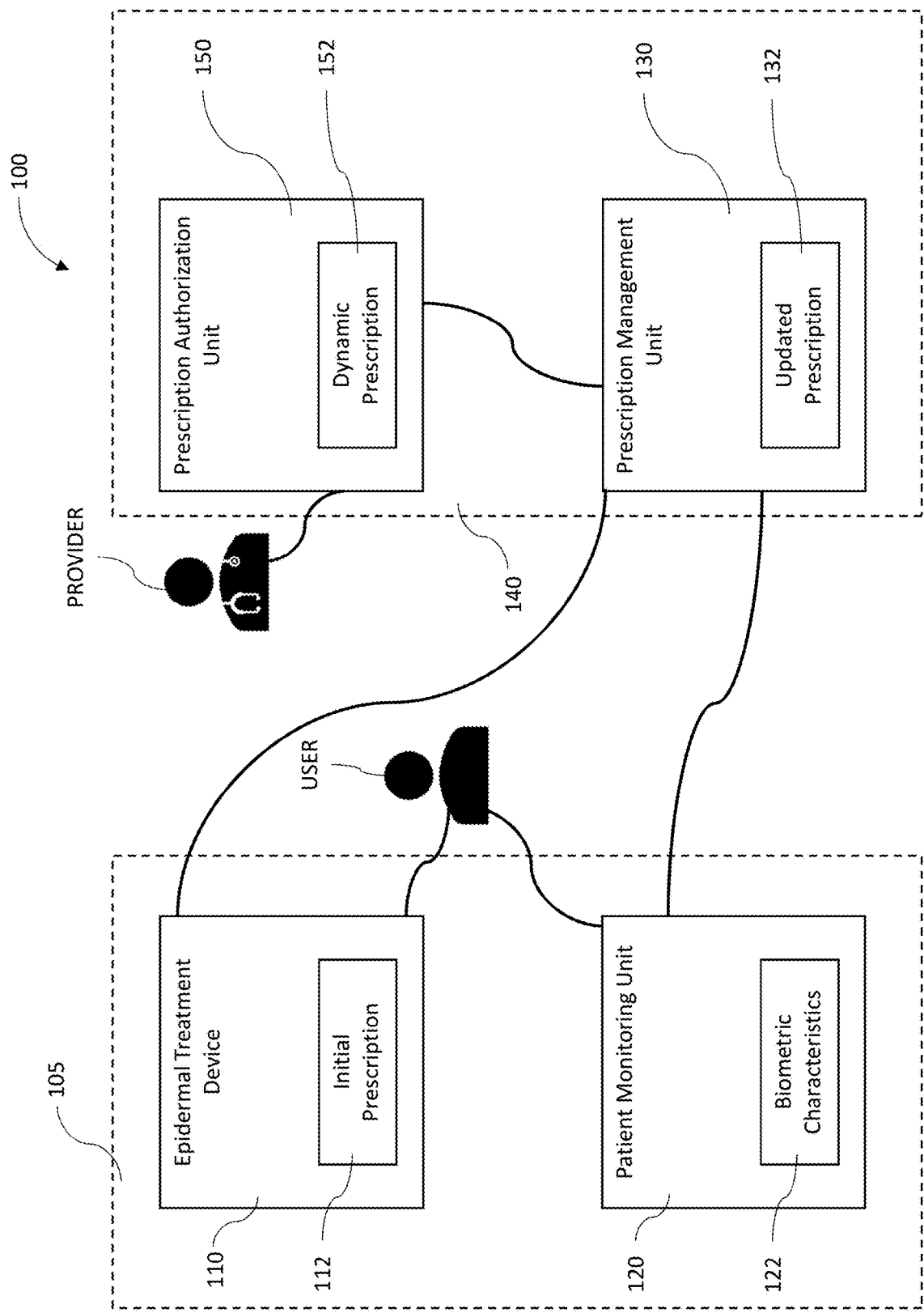
Figure 2A:
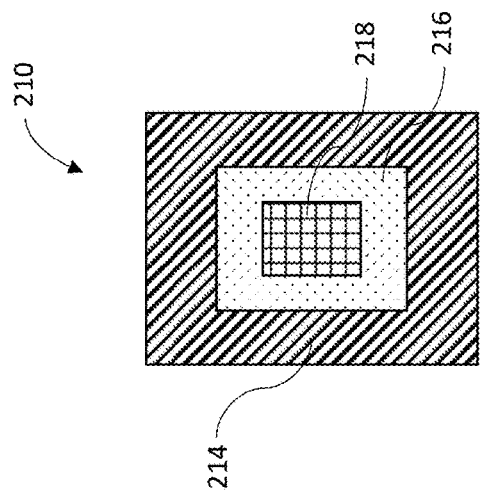
Figure 2B:
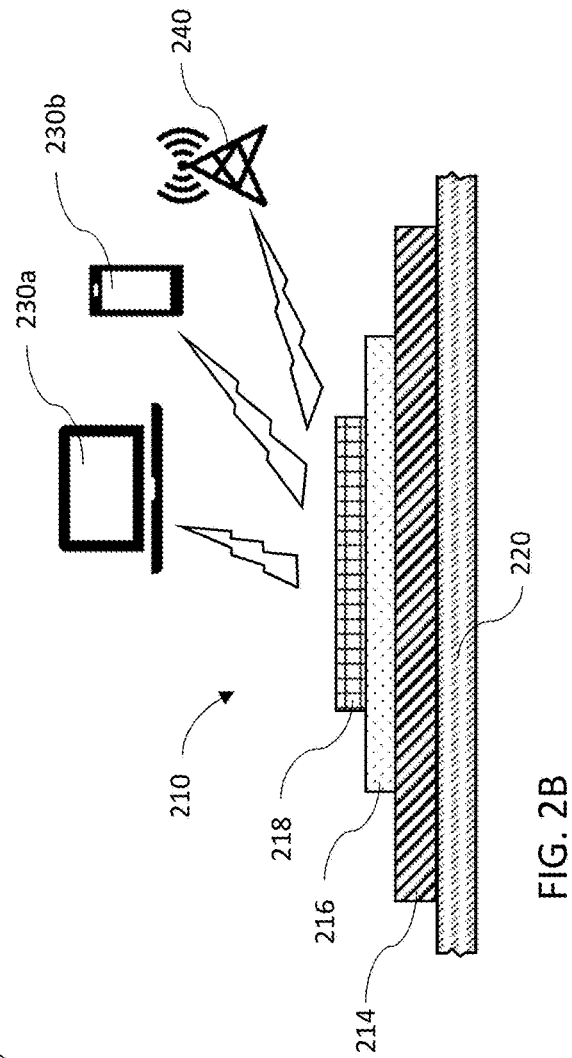
Figure 2C:
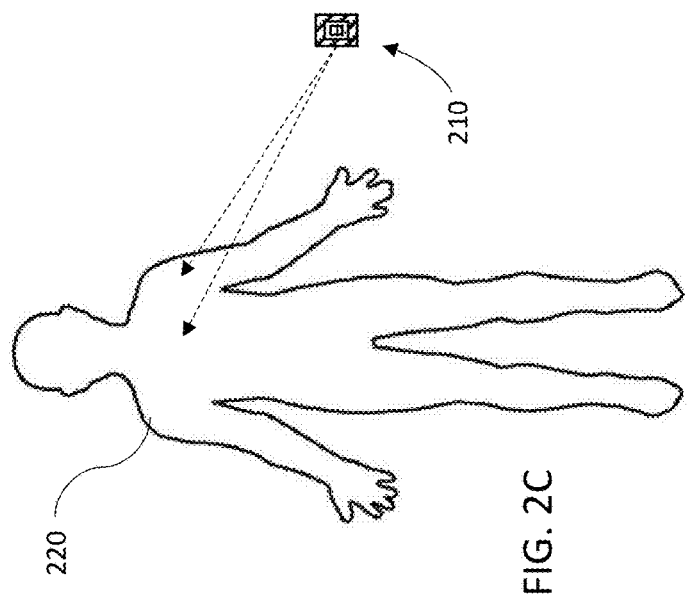
Figure 3B:
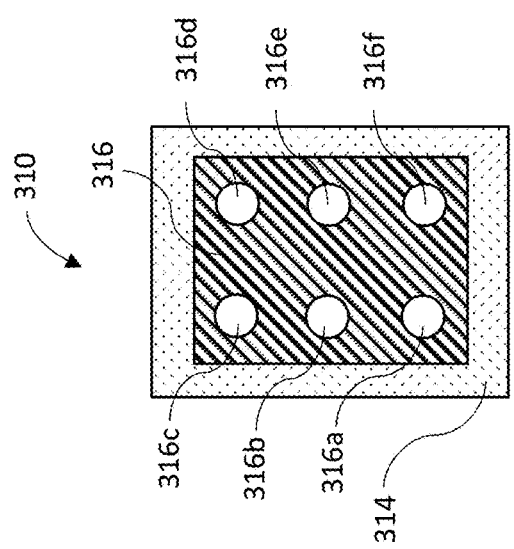
Figure 3A:
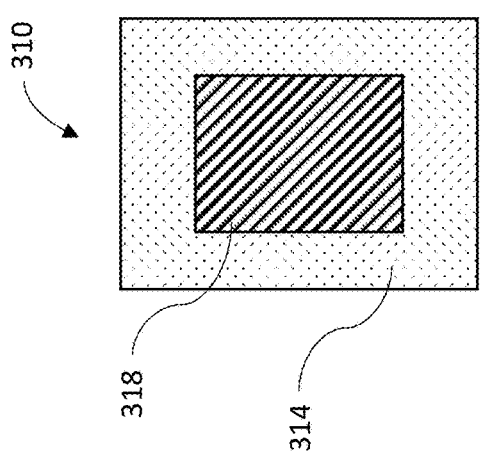
Figure 3D:
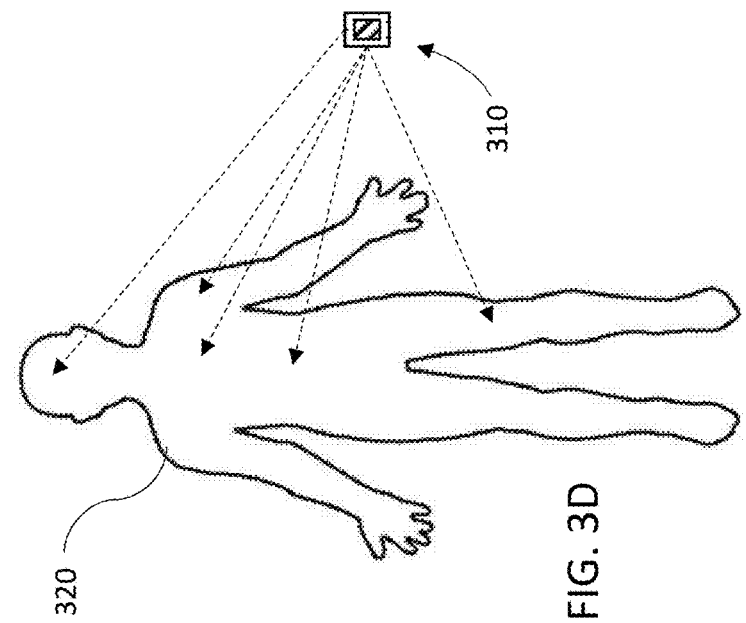
Figure 3C:
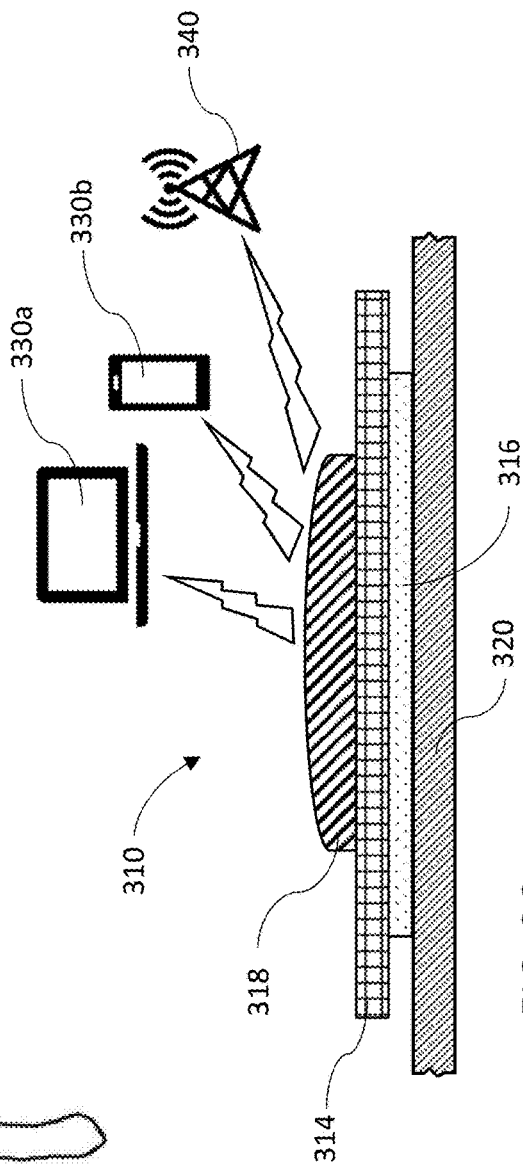
Figure 4:
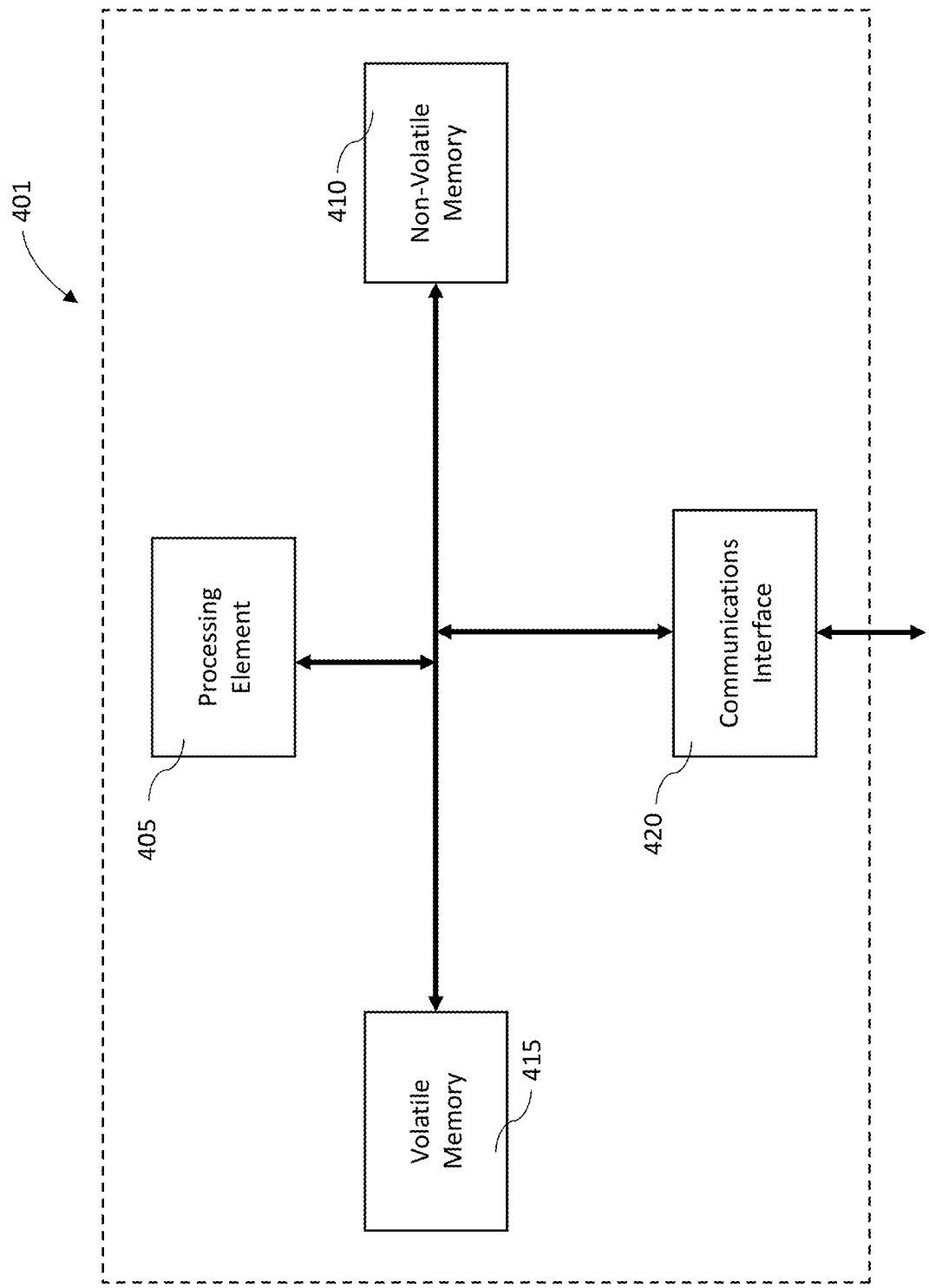
Figure 5:
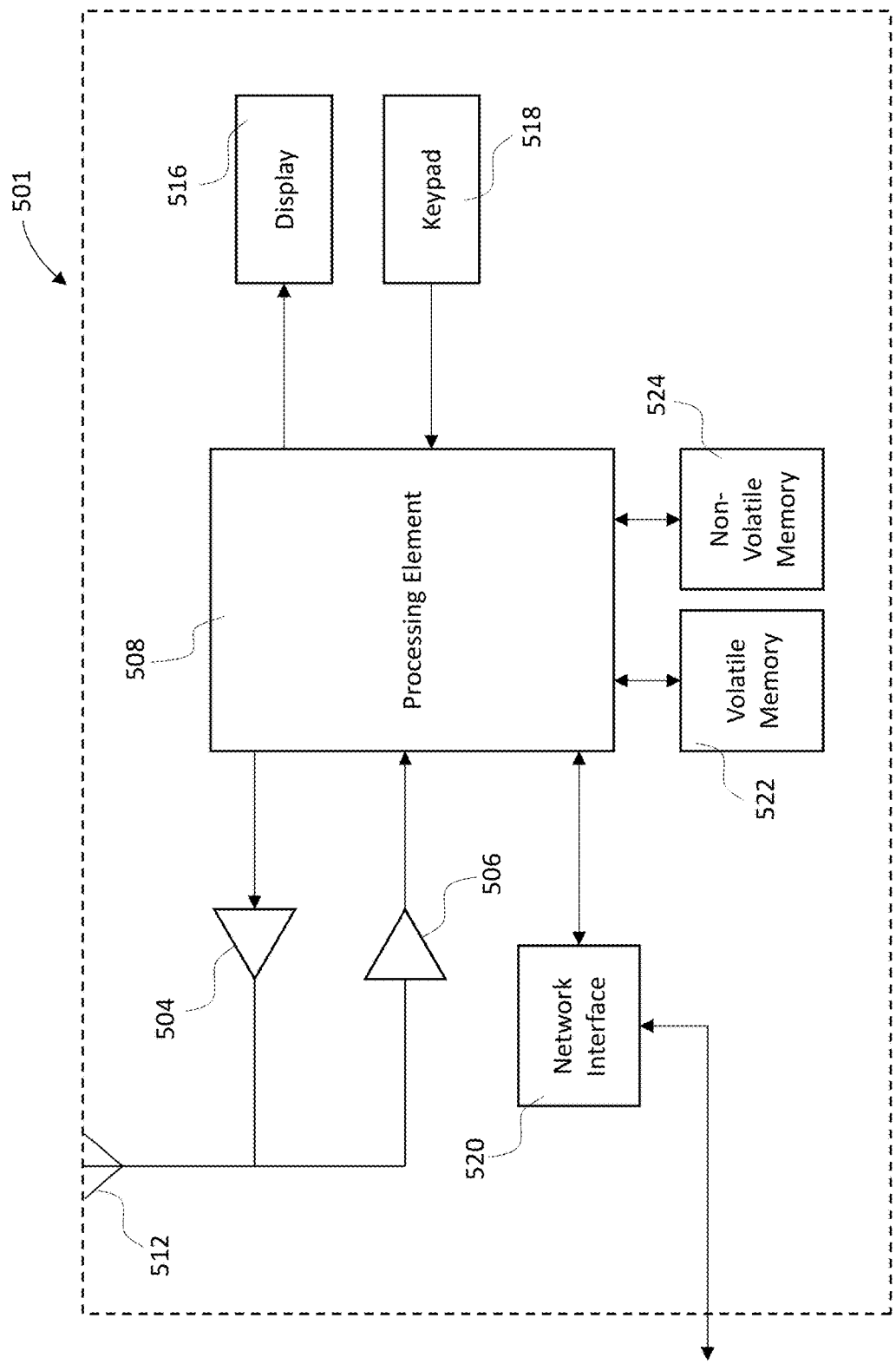
Figure 6:
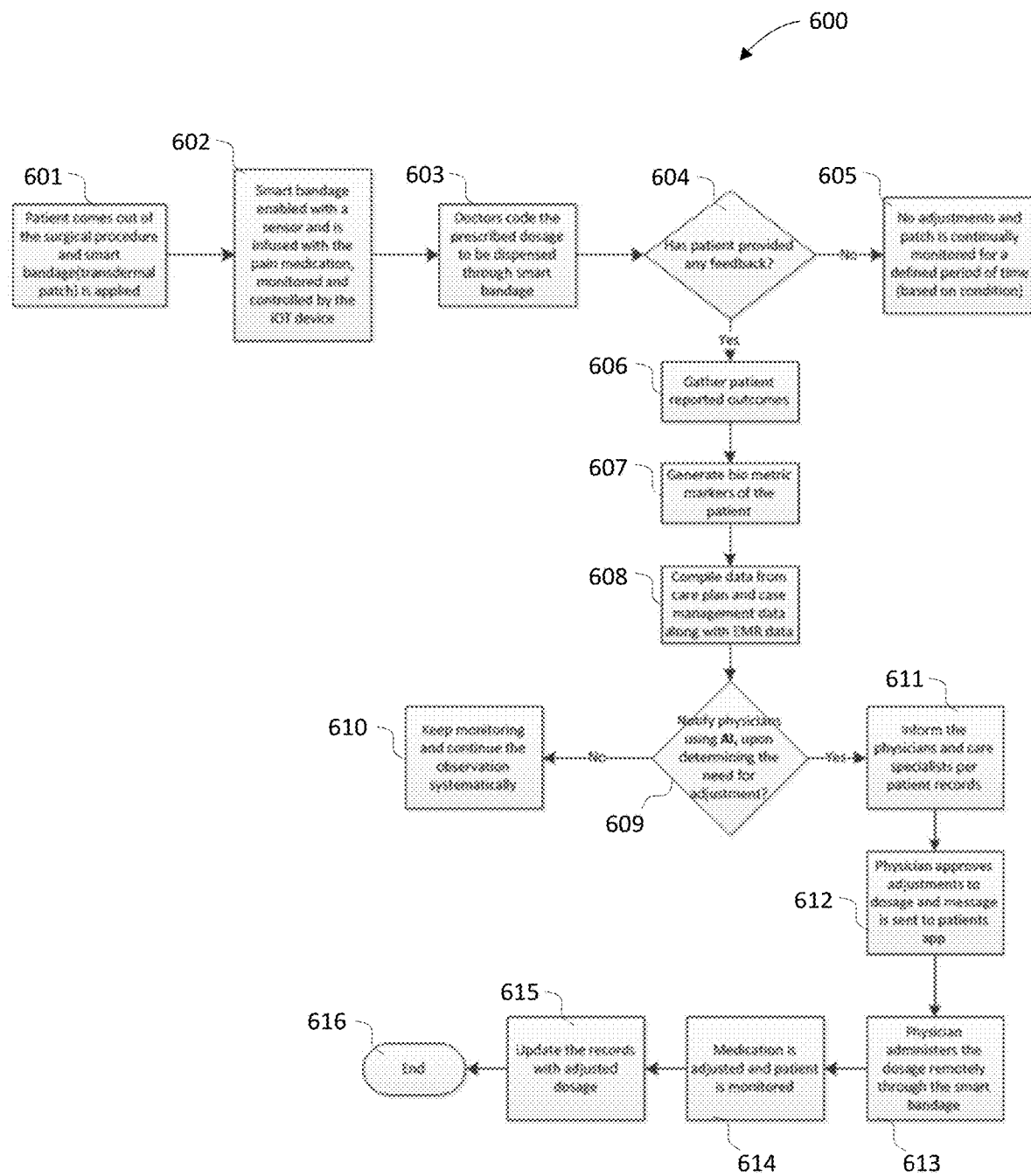
Figure 7:
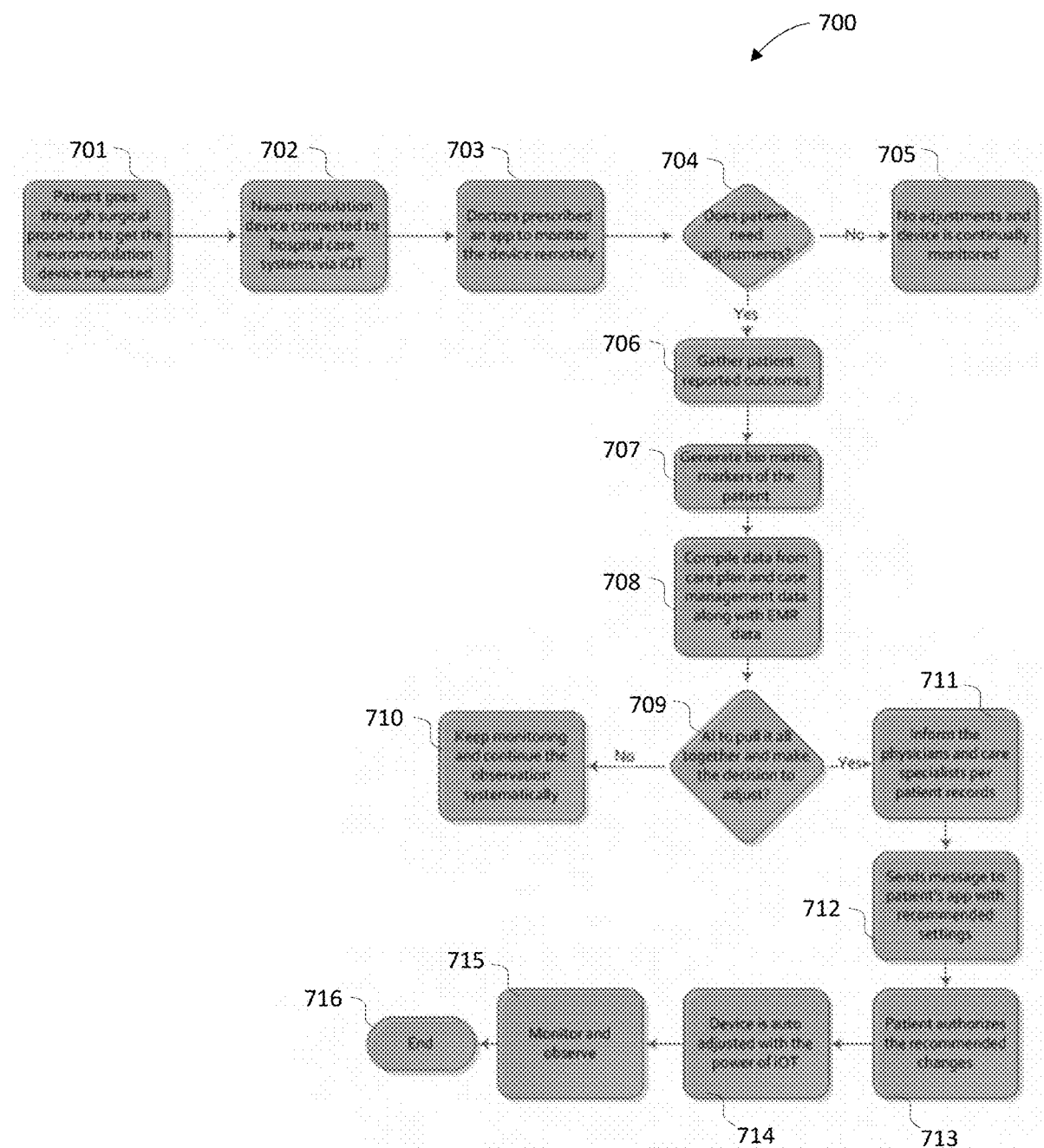
Figure 8:
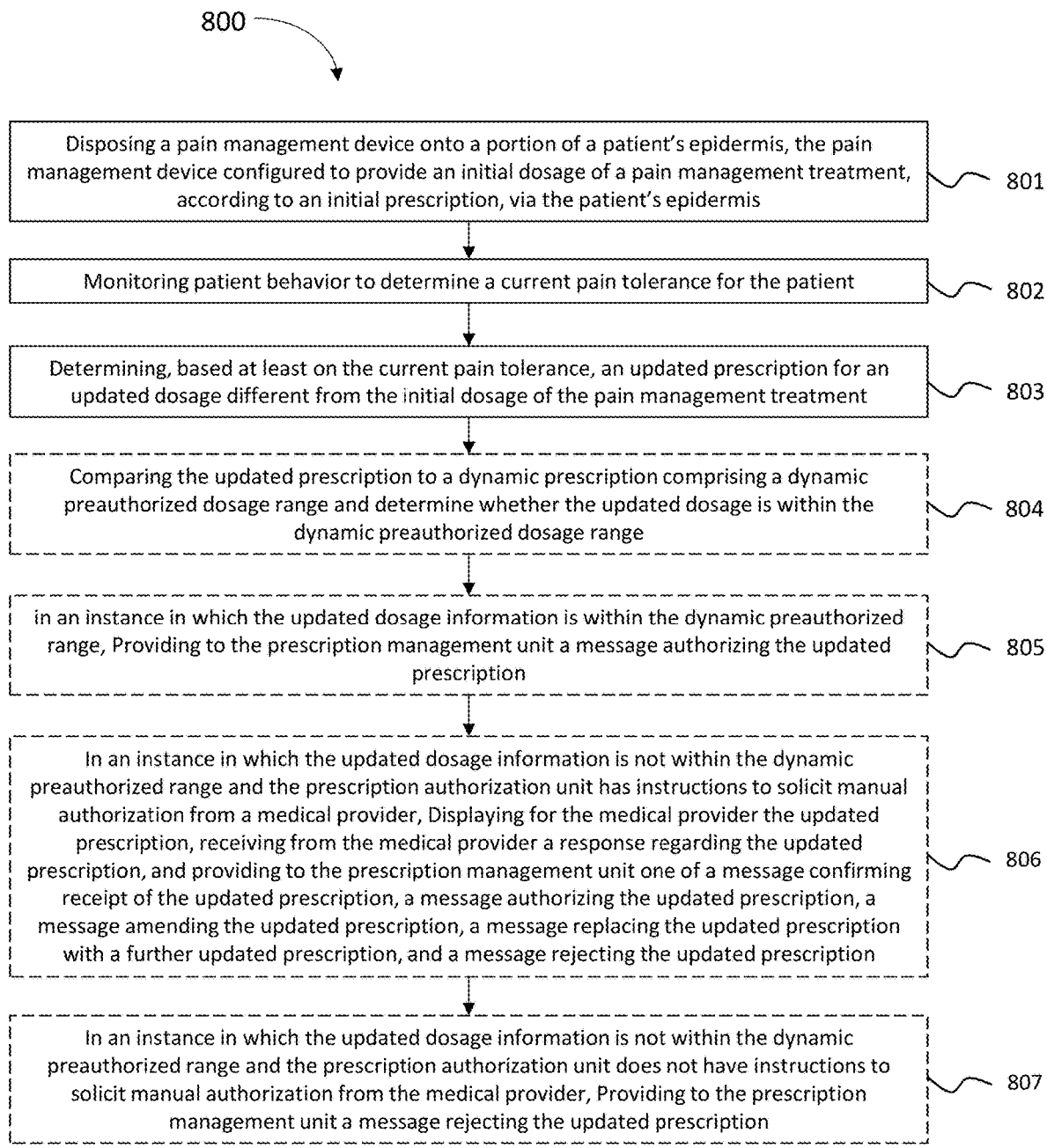
Figure 9:
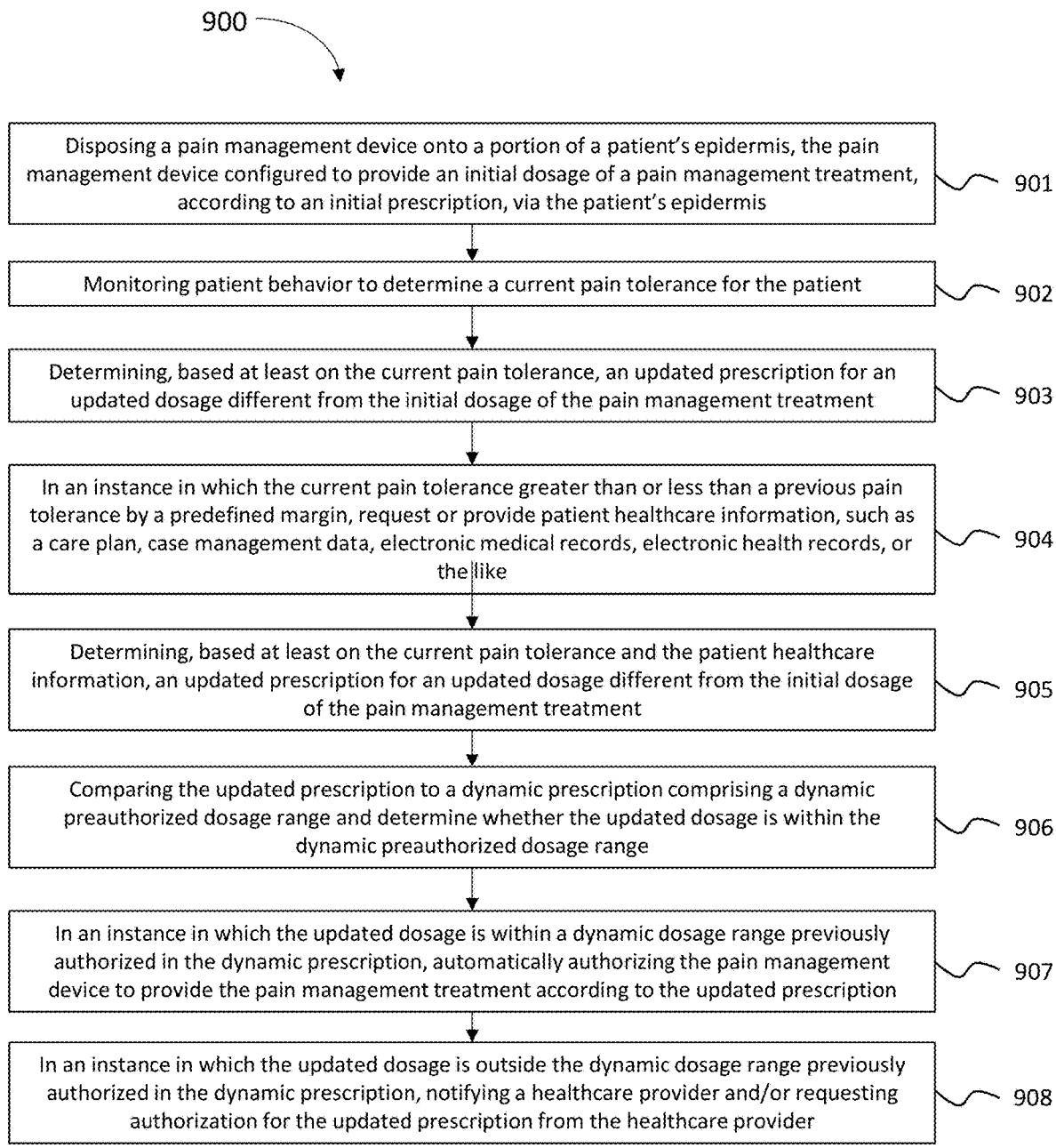

Having thus described the invention in general terms, reference will now be made to the accompanying drawings, which are not necessarily drawn to scale, and wherein:

FIG. 1A provides an exemplary overview of a system for dynamically administering pain management treatments remotely, according to some embodiments described herein;

FIG. 1B provides an exemplary overview of a system for dynamically administering pain management treatments remotely, according to some embodiments described herein;

FIG. 1C provides an exemplary overview of a system for dynamically administering pain management treatments remotely, according to some embodiments described herein;

FIG. 2A illustrates an exemplary pain management device configured to be operably coupled to a patient for remote pain management, according to some embodiments described herein;

FIG. 2B illustrates an exemplary pain management device configured to be operably coupled to a patient for remote pain management, according to some embodiments described herein;

FIG. 2C illustrates an exemplary pain management device configured to be operably coupled to a patient for remote pain management, according to some embodiments described herein;

FIG. 3A illustrates an exemplary pain management device configured to be operably coupled to a patient for remote pain management, according to some embodiments described herein;

FIG. 3B illustrates an exemplary pain management device configured to be operably coupled to a patient for remote pain management, according to some embodiments described herein;

FIG. 3C illustrates an exemplary pain management device configured to be operably coupled to a patient for remote pain management, according to some embodiments described herein;

FIG. 3D illustrates an exemplary pain management device configured to be operably coupled to a patient for remote pain management, according to some embodiments described herein;

FIG. 4 provides an example predictive data analysis computing entity in accordance with some embodiments discussed herein;

FIG. 5 provides an example external computing entity in accordance with some embodiments discussed herein;

FIG. 6 is a block flow diagram of an example process for dynamically administering a pain management treatment remotely, according to some embodiments described herein;

FIG. 7 is a block flow diagram of an example process for dynamically administering a pain management treatment remotely, according to some embodiments described herein;

FIG. 8 is a block flow diagram of an exemplary method for dynamically administering a pain management treatment remotely using a smart bandage, according to some embodiments described herein; and FIG. 9 is a block flow diagram of an exemplary method for dynamically administering a pain management treatment remotely using a neuromodulation device, according to some embodiments described herein.

DETAILED DESCRIPTION

Various embodiments of the present disclosure will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

As used herein, the terms "data," "content," "information," and similar terms may be used interchangeably, according to some example embodiments of the present invention, to refer to data capable of being transmitted, received, operated on, displayed, and/or stored. Thus, use of any such terms should not be taken to limit the spirit and scope of the disclosure. Further, where a computing device is described herein to receive data from another computing device, it will be appreciated that the data may be received directly from the other computing device or may be received indirectly via one or more computing devices, such as, for example, one or more servers, relays, routers, network access points, base stations, and/or the like.

As used herein, the term "computer-readable medium" as used herein refers to any medium configured to participate in providing information to a processor, including instructions for execution. Such a medium may take many forms, including, but not limited to a non-transitory computer-readable storage medium (for example, non-volatile media, volatile media), and transmission media. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Examples of non-transitory computer-readable media include a floppy disk, a flexible disk, hard disk, magnetic tape, any other non-transitory magnetic medium, a compact disc read only memory (CD-ROM), compact disc compact disc-rewritable (CD-RW), digital versatile disc (DVD), Blu-Ray, any other non-transitory optical medium, punch cards, paper tape, optical mark sheets, any other physical medium with patterns of holes or other optically recognizable indicia, a random access memory (RAM), a programmable read only memory (PROM), an erasable programmable read only memory (EPROM), a FLASH-EPROM, any other memory chip or cartridge, a carrier wave, or any other non-transitory medium from which a computer can read. The term computer-readable storage medium is used herein to refer to any computer-readable medium except transmission media. However, it will be appreciated that where embodiments are described to use a computer-readable storage medium, other types of computer-readable mediums may be substituted for or used in addition to the computer-readable storage medium in alternative embodiments.

As used herein, the term "circuitry" refers to all of the following: (a) hardware-only circuit implementations (such as implementations in only analog and/or digital circuitry); (b) to combinations of circuits and computer program product(s) comprising software (and/or firmware instructions stored on one or more computer readable memories), such as (as applicable): (i) to a combination of processor(s) or (ii) to portions of processor(s)/software (including digital signal processor(s)), software, and memory(ies) that work together to cause an apparatus, such as a mobile phone or server, to perform various functions described herein); and (c) to circuits, such as, for example, a microprocessor(s) or a portion of a microprocessor(s), that require software or firmware for operation, even if the software or firmware is not physically present. This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, other network device, and/or other computing device.

As used herein, the term "computing device" refers to a specialized, centralized device, network, or system, comprising at least a processor and a memory device including computer program code, and configured to provide guidance or direction related to the charge transactions carried out in one or more charging networks.

As used herein, the terms "about," "substantially," and "approximately" generally mean plus or minus 10% of the value stated, e.g., about 250 μm would include 225 μm to 275 μm, about 1,000 μm would include 900 μm to 1,100 μm.

As used herein, the terms "provider," "doctor," "physician," and "medical professional" generally refer to any entity, whether an individual, an organization, a system, a network, a device, an apparatus, or a person, that provides oversight for the remote administration of pain management treatments to a patient.

As used herein, the terms "patient" and "user" generally refer to a person to whom a pain management treatment is being remotely administered.

Overview

Patients often experience pain due to a surgical procedure, a body's wear and tear due to age, challenging activities like sports, and the like. In many cases, a patient consults with their doctor or other healthcare provider, patient health records are created, biometric and biological characteristics are measured and/or monitored, and pain management treatments may be administered to reduce or eliminate pain experienced by the patient.

Without wishing to be bound by any particular theory, the transmission of pain in a human may be divided into four stages: transduction, transmission, perception, and modulation. In transduction, the pain stimulus is transformed into a nerve impulse. Nociceptors are receptors on the surface of the nerve endings which respond to the noxious stimulus. The noxious stimulus can be thermal, mechanical (pressure), or chemical. The stimulus interacts with the receptors causing chemical changes in the body that causes the nerve to create an electrical signal or action potential. The stimulus must be strong enough in order for the sensory nerve fiber to create an action potential. If the stimulus is large enough the nerve and nearby cells release chemical pain mediators such as prostaglandin and others which can lead to primary sensitization or the activation of more receptors. During transmission the nerve impulse travels from the site of transduction to the brain releasing neurotransmitters. Perception is when the pain becomes a conscious awareness. During modulation pain is increased or decreased by the body through descending and ascending mechanisms. Signs of pain in the body may include elevated heart rate, elevated blood pressure, and elevated respiratory rate. Receiving information from the body such as physiological changes and release of mediators can provide support to the prescriber about the need to adjust medications.

For instance, when a patient goes through a surgical procedure, pain medication may be prescribed in doses that are determined to be needed on the basis of the patient's pain tolerance or pain threshold that particular day, in view of the patient's historical health records, current biometric or biological characteristics, and the provider's judgement and expertise. However, the dosage for a prescribed pain medication is typically only reviewed and updated, e.g., based on changes in the patient's pain tolerance/threshold or a change in the patient's biometric characteristics, at an interval of, e.g., one month or, at the most frequent, every week. This can lead to a lack of responsiveness in making changes in pain medication dosage in response to changes in the patient's symptoms, biological characteristics (e.g., symptoms, vocal pattern, gait, facial expressions, and/or the like), and a patient's response to questions about their pain tolerance and pain threshold, and/or the like.

Some pain medication numbs the sensory detail, binding opioid receptors in the brain or spinal cord to alleviate the pain. Over usage or under usage of such pain medications may have adverse effects on a patient and unused opioids can lead to or exacerbate serious issues like addiction and drug abuse. By way of example only, some recent reports indicate that between about 21% and about 29% of patients misuse opioids prescribed for chronic pain. In some sections of the United States, for example, opioid abuse has increased by 30% or more in recent years. However, even when a patient conforms to a prescribed pain medication, they may still unknowingly become addicted to the prescribed pain medication, e.g., an opioid.

Approximately 20% of the US population lives in rural areas, which have a median age of 50 years. However, there is a shortage of doctors/care providers available in those rural areas and it's a well-recognized phenomenon.

Access to care is minimized in rural areas, especially when patients need specific care like managing chronic pain. Compared to those in urban areas, patients in rural areas may need to travel 2 to 3 times farther to get the desired care. Telemedicine is slowly gaining popularity due to a lack of access to doctors in rural areas and because of the flexibility that telemedicine can offer to treat non-life-threatening conditions or for continuing care and during at-home patient recovery. As described below with regard to various embodiments of the present disclosure, the use of telemedicine, implemented for instance using artificial intelligence and connected devices like internet-of-things (IoT) devices, can lead to profound improvements in the quality and safety of telemedical patient care and remote pain management.

Furthermore, there are many innovations taking place in the medical device industry, where less invasive treatments like neuromodulation gaining momentum in place of complex back and spine surgeries. Even though these neuromodulation appointments are outpatient procedures, until the patient feels better with the correct adjustment, there are many visits they need to make to the hospital. With the rise of issues like opioid addiction, we need to find an innovative way to administer pain medication by controlling the use of pills to minimum amount. We need a new way to reduce the outpatient visits to adjust neuromodulation.

Given that opioid addiction is a growing issue, there are many alternatives coming in place to manage pain. For example, neuromodulation is gaining popularity in the recent years as an alternative pain management treatment, in addition to other alternative treatments such as physical therapy, Ayurveda and other similar treatments. However, with neuromodulation for example patients need to go and back forth and see their physician for adjustments of the device until it is suitably adjusted for the patient's needs, which likely also change over time, leading to a need for the patient to return overly frequently to their provider's office for adjustments, which can be time-consuming and costly for both the patient and their provider. On the other hand, when patients go through a surgical procedure, depending on the nature of the surgery, patient history, and a patient's recovery, pain medications may be prescribed. When the pain medications are not dispensed/consumed properly, it often leads to drug abuse.

As wearable devices continue to gain momentum in the wellness industry, wearable smart bandages/application-controlled pain sensors may be used for managing a patient's pain without exacerbating addiction and drug abuse and without placing an undue burden on patients and providers to meet in person to make regular adjustments to the pain management treatment.

As such, this disclosure provides systems, methods, apparatuses, and computer program products for patients to manage their pain on-demand by auto adjusting the medication dosage via smart bandage like a transdermal patch. The smart bandage is controlled through a smart phone which analyzes patient attributes and auto adjusts the dosage of the prescription accordingly. The system optionally incorporates the guidance of care providers/clinical staff and leverages artificial intelligence and IoT device technologies to provide safer, more responsive, and less costly pain management treatments to remote patients experiencing pain.

The presently disclosed systems, methods, apparatuses, and computer program products address the growing issue of opioid addiction and provide alternative approaches to pain management. Via this methodology, pain medication is auto administered on-demand in personalized doses and executed through an IoT-enabled or connected smart bandage, transdermal patch, neuromodulation device, or the like, configured to provide chemical, electrical, electrochemical, physical, or other such pain management treatments to a patient. As such, discussed herein are systems, methods, apparatuses, and computer program products for administering pain management solutions, treatments, medications, and electrical stimulation remotely.

Various embodiments of the present invention address technical challenges related to remote, dynamic administration of pain management solutions. For example, in some embodiments, proposed solutions utilize systems, methods, apparatuses, and computer program products that provide pain management remotely, according to a dynamic prescription. In some embodiments, the dynamic prescription provides for changes in a dosage of a medication or electrical stimulation, based for instance upon changes in the patient's pain tolerance level, biological indicators, or behavioral characteristics. In some embodiments, if it is determined that a dosage change is needed, the dosage change can be compared against the dynamic prescription to determine whether the dosage change is permitted within the scope of the dynamic prescription. In some embodiments, if the dosage change is determined to be outside what is permitted by the scope of the dynamic prescription, the updated dosage information can be provided to the patient's physician for authorization of the updated dosage. In some embodiments, the patient's pain tolerance level, biological indicators, or behavioral characteristics may be provided to the patient's physician along with the updated dosage information in order for the physician to determine if the updated dosage is warranted.

In some embodiments, a system can be provided for carrying out dynamic pain management remotely. In some embodiments, the system can comprise: an epidermal treatment device configured to be placed in operable contact with a patient's epidermis and provide an initial dosage of a pain management treatment to the patient's epidermis according to an initial prescription; and a prescription management unit in wireless communication with the transdermal patch, the prescription management unit configured to: receive patient behavior information, determine, based at least upon the patient behavior information, the patient's current pain tolerance, and determine, based on at least the patient's current pain tolerance, an updated prescription comprising updated dosage information for pain management treatment. In some embodiments, the prescription management unit is further configured to provide the updated prescription to the epidermal treatment device, wherein the epidermal treatment device is further configured, upon receiving the updated prescription from the prescription management unit, to provide an updated dosage different from the initial dosage of the pain management treatment to the patient's epidermis according to the updated prescription. In some embodiments, the system can further comprise: a patient monitoring unit and/or control unit configured to monitor one or more biometric characteristics of the patient, generate the patient behavior information, and provide the patient behavior information to the prescription management unit. In some embodiments, the patient monitoring unit can be or be hosted on or provided by a user device or a control device. In some embodiments, the patient monitoring unit, user device, and/or control device can comprise or be in operable communication with one or more devices configured to detect, measure, determine, monitor, evaluate, sense, calculate, estimate, or otherwise provide for generation or provision of the patient behavior information and/or the one or more biometric characteristics of the patient. In some embodiments, the patient monitoring unit, user device, and/or control device may comprise or be in operable communication with one or more cameras configured to capture images or video of a patient, a portion of the patient, a face of the patient, a portion of the face of the patient, and/or the like. In some embodiments, the patient monitoring unit, user device, and/or control device may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the patient monitoring unit, user device, and/or control device may comprise or be in operable communication with one or more microphones configured to capture audio associated with a patient, vocal audio of the patient, non-verbal sounds associated with the patient, and/or the like. In some embodiments, the patient monitoring unit, user device, and/or control device may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the patient monitoring unit, user device, and/or control device may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the patient monitoring unit, user device, and/or control device may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, an apparatus comprising one or more processors and one or more memory storing computer program instructions for storing and processing such information data and/or the like. In some embodiments, such as when one of the patient monitoring unit, user device, or control unit comprises a camera and is configured to capture images or video of a patient's face, the device or system can further comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time. In some embodiments, the one or more biometric characteristics are selected from among posture, gait, speech patterns, eye movements, heart rate, blood pressure, core temperature, epidermal temperature, respiration rate, epidermal perspiration rate, facial expressions, changes in facial expressions, and Prkachin and Solomon Pain Intensity (PSPI) indicators. In some embodiments, the patient behavior information is generated based at least upon the one or more biometric characteristics and at least one of: manual inputs from the patient regarding the patient's current pain level, the patient's medical records, the dosage information from the initial prescription, and the patient's historical prescription information. In some embodiments, the system can further comprise: a prescription authorization unit in wireless communication with the prescription management unit, the prescription management unit being further configured to communicate wirelessly to the prescription authorization unit at least one of: the patient behavior information, the patient's pain tolerance, the updated prescription, and the updated dosage information for pain management treatment. In some embodiments, the prescription authorization unit can be configured to: compare the updated prescription to a dynamic prescription comprising a dynamic preauthorized dosage range and determine whether the updated dosage is within the dynamic preauthorized dosage range. In some embodiments, the prescription authorization unit can be further configured to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription, receive from the medical provider a response regarding the updated prescription, and provide to the prescription management unit one of a message confirming receipt of the updated prescription, a message authorizing the updated prescription, a message amending the updated prescription, a message replacing the updated prescription with a further updated prescription, and a message rejecting the updated prescription; or, in an instance in which the updated dosage information is not within the dynamic preauthorized range and the prescription authorization unit does not have instructions to solicit manual authorization from the medical provider, provide to the prescription management unit a message rejecting the updated prescription. In some embodiments, the epidermal treatment device comprises one or more of a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, and a intrathecal drug delivery device.

In some embodiments, a method is provided. In one embodiment, the method comprises: disposing a pain management device onto a portion of a patient's epidermis, the pain management device configured to provide an initial dosage of a pain management treatment, according to an initial prescription, via the patient's epidermis; monitoring patient behavior to determine a current pain tolerance for the patient; and determining, based at least on the current pain tolerance, an updated prescription for an updated dosage different from the initial dosage of the pain management treatment. In some embodiments, the method can further comprise communicating with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the method can further comprise, in an instance in which the updated dosage information is within the dynamic preauthorized range, providing to the prescription management unit a message authorizing the updated prescription, in an instance in which the updated dosage information is not within the dynamic preauthorized range and the prescription authorization unit has instructions to solicit manual authorization from a medical provider, displaying for the medical provider the updated prescription, receiving from the medical provider a response regarding the updated prescription, and providing to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, providing to the prescription management unit a message rejecting the updated prescription.

In some embodiments, a computer program product is provided. The computer program product may comprise at least one computer-readable storage medium having computer-readable program code portions stored therein, the computer-readable program code portions comprising executable portions configured to: communicate with a pain management device disposed on a portion of a patient's epidermis, the pain management device configured to provide an initial dosage of a pain management treatment, according to an initial prescription, via the patient's epidermis; monitor patient behavior to determine a current pain tolerance for the patient and determine, based at least on the current pain tolerance, an updated prescription for an updated dosage different from the initial dosage of the pain management treatment. In some embodiments, the computer-readable program code portions can further comprise executable portions configured to: communicate with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the computer-readable program code portions can further comprise executable portions configured to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription; receive from the medical provider a response regarding the updated prescription; and provide to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, provide to the prescription management unit a message rejecting the updated prescription.

In some embodiments, an apparatus comprising at least one processor and at least one memory including computer program code is provided. In one embodiment, the at least one memory and the computer program code may be configured to, with the processor, cause the apparatus to: communicate with a pain management device disposed on a portion of a patient's epidermis, the pain management device configured to provide an initial dosage of a pain management treatment, according to an initial prescription, via the patient's epidermis; monitor patient behavior to determine a current pain tolerance for the patient and determine, based at least on the current pain tolerance, an updated prescription for an updated dosage different from the initial dosage of the pain management treatment. In some embodiments, the at least one memory and the computer program code may be configured to, with the processor, cause the apparatus to: communicate with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the at least one memory and the computer program code may be configured to, with the processor, cause the apparatus to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription; receive from the medical provider a response regarding the updated prescription; and provide to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, provide to the prescription management unit a message rejecting the updated prescription.

In some embodiments, an apparatus can comprise at least one processor and at least one memory including computer program code. In some embodiments, the apparatus can be configured to carry out dynamic pain management remotely. In some embodiments, the apparatus can comprise: an epidermal treatment device configured to be placed in operable contact with a patient's epidermis and provide an initial dosage of a pain management treatment to the patient's epidermis according to an initial prescription, wherein the apparatus is configured to: receive patient behavior information, determine, based at least upon the patient behavior information, the patient's current pain tolerance, and determine, based on at least the patient's current pain tolerance, an updated dosage different from the initial dosage, according to an updated prescription, for pain management treatment. In some embodiments, the apparatus can be further configured to: provide, via the epidermal treatment device, an updated dosage different from the initial dosage of the pain management treatment to the patient's epidermis according to the updated prescription. In some embodiments, the apparatus is further configured to receive the patient behavior information from a patient monitoring unit and/or control device configured to monitor one or more biometric characteristics of the patient and generate the patient behavior information. In some embodiments, the apparatus can comprise or be in operable communication with one or more devices configured to detect, measure, determine, monitor, evaluate, sense, calculate, estimate, or otherwise provide for generation or provision of the patient behavior information and/or the one or more biometric characteristics of the patient. In some embodiments, the apparatus may comprise or be in operable communication with one or more cameras configured to capture images or video of a patient, a portion of the patient, a face of the patient, a portion of the face of the patient, and/or the like. In some embodiments, the apparatus may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the apparatus may comprise or be in operable communication with one or more microphones configured to capture audio associated with a patient, vocal audio of the patient, non-verbal sounds associated with the patient, and/or the like. In some embodiments, the apparatus may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the apparatus may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the apparatus may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, one or more processors and one or more memory storing computer program instructions for storing and processing such information data and/or the like. In some embodiments, such as when the apparatus comprises a camera and is configured to capture images or video of a patient's face, the apparatus can comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time. In some embodiments, the one or more biometric characteristics are selected from among posture, gait, speech patterns, eye movements, heart rate, blood pressure, core temperature, epidermal temperature, respiration rate, epidermal perspiration rate, facial expressions, changes in facial expressions, and Prkachin and Solomon Pain Intensity (PSPI) indicators. In some embodiments, the patient behavior information is generated based at least upon the one or more biometric characteristics and at least one of: manual inputs from the patient regarding the patient's current pain level, the patient's medical records, the dosage information from the initial prescription, and the patient's historical prescription information. In some embodiments, the apparatus can be further configured to: communicate wirelessly, to a prescription authorization unit, at least one of the patient behavior information, the patient's pain tolerance, the updated prescription, and the updated dosage information for pain management treatment. In some embodiments, the apparatus can be further configured to: receive, from the prescription authorization unit, one or more of a message confirming receipt of the updated prescription, a message approving the updated prescription, a message amending the updated prescription, a message replacing the updated prescription with a further updated prescription, and a message rejecting the updated prescription. In some embodiments, the epidermal treatment device comprises one or more of a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, and a intrathecal drug delivery device.

In some embodiments, there is provided a system for administering pain management remotely. The system can comprise an epidermal treatment device configured to store an initial prescription and operable to provide a pain management treatment to a patient (e.g., a user). In some embodiments, the epidermal treatment device can be coupled to the user, abutted to the user, embedded in the user's skin, implanted in the user, removably coupled to the user, or in any other manner caused to provide a pain management treatment to the patient when the patient is not with their provider (e.g., configured to administer the pain management treatment remotely). The system can further comprise a patient monitoring unit configured to iteratively, discretely, or continuously, observe the user and measure, monitor, estimate, calculate, interpolate, or otherwise determine biometric characteristics about the user. The system can further comprise a prescription management unit that is in operable communication with the patient monitoring unit, the prescription management unit being configured to review the user's biometric characteristics and to determine whether the initial prescription is sufficient to reduce or eliminate the user's pain based on the user's pain tolerance or pain threshold, which is determined based on at least the biometric characteristics. The prescription management unit can also be configured to determine when a change in the initial prescription dosage is necessary based on changes in the user's biometric characteristics. In an instance in which the prescription management unit determines that a change in the dosage of the pain management treatment is needed, based at least upon the user's biometric characteristics, the prescription management unit can a) determine that the change in dosage of the pain management treatment is automatically approved based upon some initial instructions regarding a change tolerance or margin about the initial dosage that the prescription management unit is instructed to automatically authorize, b) determine that the dosage change is an errant dosage change based upon the magnitude of the change relative to the dosage of the initial prescription and request further biometric characteristics be provided from the patient monitoring unit, or c) determine that the change in dosage of pain management treatment is needed but that it falls outside of any provided change tolerance or margin relative to the initial dosage, and request authorization for the updated dosage from a provider or a provider device. With regard to option c) from above, the system can further comprise a prescription authorization unit configured to store or receive a dynamic prescription associated with the user and with the particular pain management treatment. The dynamic prescription can be developed based upon provider-provided and/or patient-provided data such as electronic health records, individual health records, international or domestic health regulations, provider management systems, patient preferences, the patient's insurance details, the patient's historical biometric data, historical biological data, historical medical records, and the like. The dynamic prescription can comprise a set of 'if/then' elements or the like that the prescription authorization unit is configured to answer in a particular order. In some embodiments, the dynamic prescription can include an initial question or initial set of questions that relate, for instance, to a change in the patient's pain tolerance or pain threshold. In some embodiments, the dynamic prescription can include subsequent questions or set of questions that relate, for instance, to a provider limit on the dosage of the pain management treatment that considers the patient's biometric, biological, medical, or other characteristics or data (e.g., the patient's heart rate, blood pressure, gait, or the like). In some embodiments, the dynamic prescription can also include a question or a set of questions related to domestic or international regulations related to what and how much pain management treatments can be administered/changed remotely, absolute or relative dosage limits, and/or the like. In some embodiments, the dynamic prescription can include a question or a set of questions related to past changes in the dosage, the rate and magnitude of such changes, the remaining supply of pain medication (when applicable), and/or the like. Said otherwise, the dynamic prescription, instead of providing a static dosage, can provide a dosage range that changes in response to changes in a patient's pain tolerance or pain threshold, accounting for medical or legal limits placed on dosage changes that are specific to the pain management treatment, jurisdiction, provider, application type, patient, provider, and/or the like.

By way of example only, a patient may be a 50 year old male, living in an urban area with excessive auditory environmental noxious stimuli, living alone in a two-story house, with the patient's bedroom being on the second floor and in which the only bathroom facility is on the second floor and the kitchen is on the first floor. The exemplary patient does not have an in-home health aide for meal preparation or any in-home nurse visitations scheduled, e.g., for bandage changes; the exemplary patient has a medical history of high blood pressure, is moderately obese, with three days having elapsed since receiving a total knee replacement; the patient is naïve to opioids, is only 75% adherent to the current blood pressure medication regimen; the patient's baseline blood pressure readings average between 120-130/70-80 and heart rate averages between 70-80 beats per minute when he takes his medication, but blood pressure averages between 150-160/85-90 and heart rate averages between 85-90 beats per minute when he doesn't take his meds. For such a patient, an example of a dynamic prescription may provide an initial range and then stipulate that, in an instance in which the patient's current blood pressure is at or below 155/85 and current resting heart rate is at or below 88 beats per minutes, the patient's surgical bandage was last changed 20 minutes ago, the patient recently stood for 10 min to cook breakfast after descending a flight of stairs without using a cane, the patient has a baseline pain level range of between 3-7, and the patient's current pain level is 8, then the current dosage of pain medication is not changed, the patient is advised that the current pain level may not be contributing to outlier biometrics, and the patient may be advised to sit and rest and take his blood pressure medicine; however, in an instance in which the patient's blood pressure reaches or exceeds a threshold blood pressure, such as 170/96, the patient's resting heart rate reaches or exceeds a threshold heart rate, such as 98 beats per minutes, the patient's current pain level is a 10, and the patient has already taken his blood pressure medication, then the pain management medication dosage may be increased by a first amount, at a first rate of increase, to a first updated dosage for an opioid naïve patients, or the pain management medication dosage may be increased by a second amount, at a second rate of increase, to a second updated dosage for a patient with a history of opioid use. By way of another example, a dynamic prescription can comprise a "if/then" statements, a logical progression of conditional questions, and/or an algorithm which can be used by a control unit or the like to determine if a proposed updated dosage is proper or to elect an updated dosage, e.g., from a range of dosages prescribed based upon a dynamic prescription. For instance, a dynamic prescription can comprise, at least in part, IF <Patient X> in downtown "TN" AND (age-range between 45 TO 50 AND heart-rate>147 bpm OR gait-speed<1 m/s) THEN Dosage change=+0.002 mg. Said otherwise, the preceding statement indicates that, if the patient lives in an urban location in Tennessee, is between 45 and 50, and has either a heart rate greater than 147 beats per minute for more than two minutes or a gait speed of less than 1 m/s, then the dosage of the patient's pain management medication can be increased by 0.002 mg over the same period of time. In some embodiments, the dynamic prescription can include an upper dosage range limiting term, such as "THEN Dosage change=+0.002 mg IF current Dosage is less than an upper dosage limit." In some embodiments, the exemplary dynamic prescription provided shows how the medication dosage can be changed by accounting for unusual patient activity and/or a combination of characteristics.

The dynamic prescription can be pre-authorized by the provider. In some embodiments, when the prescription management unit determines that the change in dosage of pain management treatment is needed but that it falls outside of any provided change tolerance or margin relative to the initial dosage, the prescription management unit may transmit a request for authorization of the updated dosage of the updated prescription to the prescription authorization unit. The prescription authorization unit can then review the request for the updated dosage of the updated prescription, e.g., by answering the questions related to the dynamic prescription to determine if the provider-pre-authorized dynamic prescription authorizes the updated dosage for the patient, and then a) automatically provides authorization for the updated prescription to the prescription management unit, b) automatically rejects the updated prescription (e.g., when the dosage change is suspected to be in error, when the dosage change would contravene a law, and/or the like), or c) requests approval for the updated prescription from the provider. In some embodiments, the prescription authorization unit can cause a notification, alert, message, request, or the like to be pushed to, displayed on, sent to, or otherwise provided to a provider device such as a computer, beeper, mobile phone, smart phone, tablet, or the like. The provider can then review the updated prescription and can instruct the prescription authorization unit to either allow or disallow the updated prescription, can mark the updated prescription as being a suspected errant request, can communicate with the patient/user to provide telemedical care or request that the patient/user visits the provider's office, amend the dynamic prescription based upon the updated prescription request, and/or the like. In an instance in which the prescription authorization unit or prescription management unit automatically authorizes the updated prescription, or in an instance in which the provider manually authorizes the updated prescription, the prescription management unit can communicate with either the patient monitoring unit or the epidermal treatment device to provide the updated prescription along with authorization for the epidermal treatment device to administer the pain management treatment to the user according to the updated prescription. The epidermal treatment device can then replace the initial prescription with the updated prescription and comply with the specific dosage/timing requirements of the updated prescription in administering the pain management treatment to the user.

In some embodiments, there is provided an apparatus for accurately determining a pain tolerance or a pain threshold for a patient remotely. The apparatus can comprise one or more processors and one or more memory storing computer program code. The apparatus can be configured to iteratively, discretely, or continuously, observe the user and measure, monitor, estimate, calculate, interpolate, or otherwise determine biometric, biological, medical, or other suitable characteristics about the patient. The apparatus can determine the patient's current pain tolerance or pain threshold based on at least the biometric, biological, medical, or other suitable characteristics. In some embodiments, the apparatus can comprise or be in operable communication with one or more devices configured to detect, measure, determine, monitor, evaluate, sense, calculate, estimate, or otherwise provide for generation or provision of the patient behavior information and/or the one or more biometric characteristics of the patient. In some embodiments, the apparatus may comprise or be in operable communication with one or more cameras configured to capture images or video of a patient, a portion of the patient, a face of the patient, a portion of the face of the patient, and/or the like. In some embodiments, the apparatus may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the apparatus may comprise or be in operable communication with one or more microphones configured to capture audio associated with a patient, vocal audio of the patient, non-verbal sounds associated with the patient, and/or the like. In some embodiments, the apparatus may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the apparatus may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the apparatus may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, one or more processors and one or more memory storing computer program instructions for storing and processing such information data and/or the like. In some embodiments, such as when the apparatus comprises a camera and is configured to capture images or video of a patient's face, the apparatus can comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time. The apparatus can comprise a display and a user interface configured to allow for the patient to interact with an application, program, browser, or the like stored on and/or hosted by the apparatus. In some embodiments, the patient may provide feedback about their current pain tolerance or pain threshold at certain intervals, e.g., regularly, irregularly, when they perceive a change in their pain tolerance or pain threshold, and/or the like. In some embodiments, the apparatus can include one or more sensors, one or more camera devices, one or more keyboards, one or more touchscreens or other such interactive input devices, and/or the like. In some embodiments, the apparatus can include one or more activity monitoring devices or healthcare monitoring devices, such as but not limited to: a gyroscope, a magnetometer, an accelerometer (e.g., a 3-axis accelerometer), a camera, a geospatial positioning system, a barometer, an altimeter, a step counter, a blood pressure monitor, a heart rate monitor, a respiration monitor, ambient pressure sensor, ambient temperature sensor, ambient oxygen sensor, an electrocardiogram device, an electroencephalogram device, skin temperature sensor, a myocardial sensor, a blood oxygen sensor, a elastomeric plethysmography (EP) device (e.g., one or more piezoelectric sensors on an elastic band for elastomeric plethysmography via current variation), an impedance plethysmography (IP) device, a respiratory inductive plethysmography (RIP) device, a photoplethysmography (PPG) device configured to measure blood oxygen saturation using pulse oximetry principles by measuring two adjacent peaks in a blood vessel variation waveform, a continuous glucose monitoring (CGM) device, or the like. In some embodiments, the apparatus can include one or more speakers and/or one or more microphones. In some embodiments, the apparatus is configured to monitor, measure, calculate, estimate, sense, observe, interpret, derive, or otherwise determine one or more biometric, biological, medical, or movement characteristics of the patient and the chance over time thereof, such as but not limited to: facial features, facial expressions, facial micro-expressions, gait, heart rate, heart rate variability, heart rate irregularity, incidents of a fall experienced by the patient, step count, step pace, blood pressure, respiration rate, eye movements, blink rate, pupil dilation, vocal/speech pattern, speech pace, incidents of slurred speech, incidents of key words or sounds that may indicate pain or pain relief, posture, perspiration rate, breathing rate, sudden reduction or loss of hearing (e.g., if a patient suddenly increases the speaker volume on the apparatus when interacting with the apparatus), dermal and subdermal perfusion rates, time spent sitting versus standing, limb and trunk movement and range of motion, sleep duration and sleep type patterns, combinations thereof, and/or the like. For instance, the apparatus can capture a patient's facial expressions when they are using the device, e.g., by using the front facing camera on a smart phone and implement an objective pain evaluation or an objective pain scoring approach, such as a facial action coding system (FACS) in conjunction with Prkachin Solomon Pain Intensity (PSPI) analysis or other suitable approaches, to track pain tolerance or pain threshold changes in the patient. The apparatus can use an algorithm, neural network, machine learning model, and/or the like to determine changes in the patient's pain tolerance or pain threshold.

In some embodiments, there is provided a method for preparing a dynamic prescription of a pain management treatment for a patient. In some embodiment, the method can comprise determining the internet-of-things (IoT) devices and sensors available for a patient and the device and sensor boundaries with respect to particular biological indicators or characteristics. The method can further comprise establishing the patient's current pain threshold/pain tolerance and associating the patient's current pain threshold/pain tolerance with the patient's particular biological indicators or characteristics. The method can further comprise determining a current dosage of a pain management treatment being administered to the patient and associating the current dosage of the pain management treatment with the patient's current pain threshold/pain tolerance and the patient's particular biological indicators or characteristics. The method can further comprise receiving, from a provider, an outside dosage range indicating a magnitude of increase of the dosage and a magnitude of decrease of the dosage that are allowed for the patient. The method can further comprise receiving, from the provider, a set of conditions in which the current dosage of the pain management treatment can be changed, within the outside dosage range. As an initial non-limiting example, the provider may indicate that if the patient's pain tolerance increases to above 9/10 AND the patient belongs to a certain demographic area AND if the patient's age is within a particular age range, then the current dosage can be increased to an updated dosage higher than the current dosage for a particular time period, e.g., before re-analyzing patient pain tolerance/pain threshold or reverting back to the current dosage lower than the updated dosage. As a subsequent non-limiting example, the provider may indicate that if the patients pain tolerance/pain threshold reduces by more than a threshold reduction in pain tolerance/pain threshold AND the patient belongs to a certain demographic area OR if a particular biological indicator is within a predetermined range considered to be suitable for a reduction in dosage, then the current dosage can be decreased to an updated dosage lower than the current dosage for a particular time period, e.g., before re-analyzing patient pain tolerance/pain threshold or reverting back to the current dosage higher than the updated dosage. As a further non-limiting example, the patient may have a wearable device that sends a signal to a provider management system; for example, a cardiology patient taking statins that is determined to be involved in excessive/out-of-normal physical activity, causing a reduction in blood sugar level, which may necessitate a reduction in the dosage of a remotely administered diabetes medication for a particular time period. As yet another non-limiting example, for an oncology patient, to whom a medication is being administered remotely according to any of the processes or methods described herein, a provider may code a dynamic prescription for the oncology patient that indicates, if the oncology patient is exposed to conditions that are not optimal in view of their medical condition and medication being administered AND/OR if the patient is in a particular demographic group (e.g., a particular sex, race, nationality, geographic location, employment type, or any other suitable group of patients) AND/OR if the patient has an age that is within a particular predetermined age range AND/OR if the patient received their last oncology treatment (e.g., radiation therapy, chemotherapy, and/or the like) within a predetermined window preceding the date and time of analysis, then the dynamic prescription can automatically instruct the patient, the provider, the patient's remote pain management treatment administration device (e.g., transdermal patch, neuromodulation device, and/or the like) to increase their dosage of the pain management treatment for a predetermined time period. In some embodiments, in order for a provider to "code" the dynamic prescription via digital means within a provider management system, there may be an "INPUT" which needs to be "ANALYZED" before coding the prescription. For example, an "INPUT" may include without limitation one or more of (a) information related to the sensors or IoT devices that the patient has registered and/or that are in communication with the apparatus or system carrying out the method of establishing the dynamic prescription, (b) capabilities and configurations for the various sensors or IoT devices, either derived from the respective sensor/IoT device, culled from the above-mentioned information, or provided by or retrieved from a third party, (c) a summary of edge computing capabilities for each IoT device, (d) capabilities and configurations for each "coordinating device," such as a smart watch, smart home sensor, vehicle sensor, or the like, that coordinates multiple IoT devices, (e) hierarchy of sensors/IoT devices with regard to channels of communication and the configurations required for data collation and transmission from each of these devices, (f) information related to the interoperability of the various sensors/IoT devices the patient has registered, (g) information related to alternative hierarchies or channels of communication if one or more of the sensors/IoT devices that the patient has registered becomes unreachable or is suspected of being corrupted or providing erroneous data, and/or (h) other suitable information helpful or necessary for the establishment of a stable channel of communication between and within the network and the sensors/IoT devices such that the dynamic prescription can be generated and/or updated based upon inputs from the provider as well as feedback and data provided by the patient and the various sensors/IoT devices. The method for initial coding of the dynamic prescription, in addition to or alternative to the approach and process elements described above, can include presenting the provider with the available "INPUTS," allowing the provider to choose the appropriate collection of sensors/IoT devices that are appropriate for considering with regard to the dynamic prescription. The provider can then indicate or code in the dynamic prescription (which may for instance be carried out by selecting among a drop-down list or conducting a search) the appropriate biological indicators, patient movement data, healthcare metrics, and/or environmental data that should be considered from among the data received from the collection of approved sensors/IoT devices the patient has registered. The provider can then identify, for each sensor or IoT device and/or for each type of feedback or data, the expected range or value, optionally one or more secondary indicators or considerations that should be considered in such an instance, and a dosage change that should be carried out in such an instance. For example, for a patient's heart rate monitor, the provider can code a particular heart rate range that is expected for the patient, such that when the heart rate monitor returns a heart rate outside the provider-indicated expected range of heart rates, the dynamic prescription can increase or decrease the dosage based on such an indication. When coding the dynamic prescription, the provider may select a particular frequency or a particular time frame and iteration count for any or all of the analyses being done remotely to determine the patient's pain tolerance or pain threshold, and/or can indicate how the dosage should change based upon changes in the respective analyses. The provider may also indicate the duration of pain management treatment and/or can indicate one or more stages of pain management treatment (e.g., through a staged weaning period). When coding the dynamic prescription, the provider may select a particular activity or group of activities to indicate how the prescription changes based on a particular input, such as information related to the initial cause of pain, the intensiveness of any preceding surgeries or inpatient/outpatient treatments, how many calories the patient has consumed, the number of stiches the patient received following a surgery, or any other suitable input. When coding the dynamic prescription, the provider may select one or more user contexts, such as the demographic information of the patient, to consider when dynamically changing the prescription. When coding the dynamic prescription, the provider may select one or more environmental conditions or changes to consider when dynamically changing the prescription, such environmental conditions or changes including but not limited to exposure to contaminants or harsh environmental conditions, the frequency and/or type of human interaction the patient has (e.g., by tracking emails, SMS texts, phone calls, or the like for a period of time following a surgery), the patient's social media accounts and their interactions with others on these social media platforms, application programming interface (API) calls to the weather system or a third-party weather service, temperature sensor readings, barometric pressure sensor readings, patient activity/motion data, and/or the like. When coding the dynamic prescription, the provider may select a prescription renewal time, e.g., by analyzing the consumption rate of the drug, and authorize the dynamic prescription and/or associated machine learning algorithm or artificial intelligence program carrying out the dynamic prescription to suggest changes or pre-authorize changes only at particular times or with a consideration for the remaining stock of a drug that the patient has on hand. In some embodiments, when the dynamic prescription is updated and/or when their effective dosage is changed according to the dynamic prescription, the patient may be notified through push notification from an application, email, phone call, SMS text message, or the like regarding the change in their prescription or effective dosage. In some embodiments, when the dynamic prescription is updated and/or when their effective dosage is changed according to the dynamic prescription, the patient may be asked to authorize the change in their prescription or effective dosage. In some embodiments, when the dynamic prescription is updated and/or when their effective dosage is changed according to the dynamic prescription, the patient may be notified regarding the change in their prescription or effective dosage and given an opportunity to temporarily stop the change in their prescription or effective dosage until the provider has reviewed the change and has authorized the change. In some embodiments, the patient may be notified regarding the change in their prescription or effective dosage only when the dynamic prescription and/or associated machine learning algorithm or artificial intelligence program carrying out the dynamic prescription determines that the calculated necessary dosage change is outside the range preauthorized under the dynamic prescription, elevated the request for a dosage change to the provider, and the provider has authorized a change not only to the dosage but also to the dynamic prescription. In some embodiments, the dynamic prescription and/or associated machine learning algorithm or artificial intelligence program carrying out the dynamic prescription can track and/or request updates from the patient's sensors/IoT devices regarding the quantity of a remaining stock of the patient's medication. In some embodiments, in an instance in which the dynamic prescription and/or associated machine learning algorithm or artificial intelligence program carrying out the dynamic prescription determine that a change in the dosage will unduly diminish the quantity of the remaining stock of the patient's medication, and/or will result in a depletion of the patient's medication before such a time as the patient is scheduled (or legally allowed) to replenish their stock of the medication, can take these competing challenges and interests into account when determining a necessary change in the dosage of the patient's medication and/or can disallow changes to the dosage administered in order to maintain sufficient stock so that the patient does not run out of their medication before they receive a replenishing supply. In some embodiments, the dynamic prescription and/or associated machine learning algorithm or artificial intelligence program carrying out the dynamic prescription, upon determining that the patient's stock of a medication is low or that a change made to their dosage will result in a more rapid diminishment of the patient's stock of the medication, can provide an alert to the provider such that the provider can coordinate providing the patient with a replenishing supply of their medication, amend the patient's plan of care with regard to the time horizon for administering the drug, contravene the dosage change, and/or contact the patient for follow-up telemedical care.

In some embodiments, the provider may initially develop one or more databases comprising historical patient data, regulatory limits for pain management treatments, provider instructions for each patient, and the like. One or more databases may comprise electronic health records, individual health records, international and domestic health regulations, provider management systems, patient preferences, the patient's insurance details, the patient's historical biometric data, historical biological data, historical medical records, and the like. One or more networks can be established by which the provider databases and devices can communicate with the device(s) used for remote pain management treatment administration, and/or intermediary devices. In some embodiments, the provider can manage one or more computing entities (e.g., servers, cloud computing environments, personal computers, tablets, smart phones, and/or the like) that store the one or more databases, host the prescription authorization unit, store the dynamic prescription, and/or carry out one or more algorithms for determining that the updated prescription complies with the dynamic prescription. The provider's computing entity(ies) can comprise one or more displays configured to display information to the provider, e.g., configured to display an alert, an alarm, a request, or the like, from the prescription authorization unit, associated with the updated prescription, a request for manual authorization of the updated prescription, or the like. In some embodiments, the provider's computing entity(ies) can comprise, for instance, a keyboard, a mouse, a touchscreen, a voice assistant, a process, or memory device, a wired or wireless input channel, one or more input ports, or the like. In some embodiments, the provider's computing entity(ies) can be accessible by the provider but actually managed by a third party, such as an insurance provider, a health records manager, a governmental agency, a non-governmental organization, or the like. In some embodiments, the provider's computing entity(ies) can be configured such that the provider can input or amend information in the computing entity(ies), databases stored thereon, the dynamic prescription, or the like. In some embodiments, the provider's computing entity(ies) can be configured to communicate, e.g., via wired or wireless communication, with one or more intermediary computing entity(ies) storing the prescription management unit and/or the patient monitoring unit or one or more user computing entity(ies) storing the epidermal treatment device, the patient monitoring unit, and/or the prescription management unit. Any or all of the provider's computing entity(ies), intermediary computing entity(ies), and/or the user computing entity(ies) can comprise one or more transmitter-receivers that are configured to send and receive messages, information, data, signals, instructions, computer program code, alerts, or the like therebetween.

In some embodiments, the epidermal treatment device can comprise a smart bandage, such as transdermal patch, that is configured to be connected to one or more networks, such as a network comprising the intermediary computing entity(ies) and/or the provider's computing entity(ies). In some embodiments, the epidermal treatment device can be applied directly to the user's skin. In some embodiments, the epidermal treatment device can comprise an adhesive underside portion and a medicated underside portion that are configured to directly abut the user's skin such that the epidermal treatment device is removably coupled to the user's skin, via the adhesive underside portion, and configured to administer a dosage of the pain management treatment to the user's skin, via the medicated underside portion. In some embodiments, the epidermal treatment device can comprise one or more stimulation elements that are configured to provide a dosage of an electrical, magnetic, electromagnetic, acoustic, or the like pain management treatment to the user. In some embodiments, the epidermal treatment device can be embedded in, implanted in, or otherwise located in or partially in the user. In some embodiments, the epidermal treatment device can comprise a transmitter-receiver configured to communicate with the intermediary computing entity(ies) and/or the provider's computing entity(ies). In some embodiments, the epidermal treatment device can be configured to communicate with an intermediary computing entity(ies), such as a smart phone, on which the patient can review their current medical information, initial or updated prescription information, monitor dosage change requests and authorization processes, report feedback about their pain tolerance or pain threshold at any suitable interval, and/or the like.

Exemplary Systems

FIGS. 1A-1C provide exemplary overviews of a system 100 that can be used to practice embodiments of the present invention, according to some embodiments. According to some embodiments, such as illustrated in FIG. 1A, the system 100 can include a user device 105 comprising an epidermal treatment device 110 configured to be operably coupled to a USER and to provide a dosage of a pain management treatment according to an initial prescription 112 stored at or received by the epidermal treatment device 110. In some embodiments, the initial prescription 112 can include instructions, permissions, settings, controls, device configurations, computer program code, or the like, suitable for the epidermal treatment device 110 to provide the dosage of the pain management treatment to the USER. In some embodiments, the initial prescription 112 can comprise a volume dosage rate of a chemical pain management treatment, a mass dosage rate of a chemical pain management treatment, a molar dosage rate of a chemical pain management treatment, or the like. In some embodiments, the initial prescription 112 can comprise a voltage, a wattage, an amperage, an amplitude, a frequency, a pulse rate, a waveform shape, or a change over time thereof, of an electrical, a magnetic, an electromagnetic, an acoustic signal, combinations thereof and/or the like.

In some embodiments, the epidermal treatment device 110 can be configured to store the initial prescription 112 and operable to provide a pain management treatment to the USER. In some embodiments, the epidermal treatment device 110 can be coupled to the USER, abutted to the USER, embedded in the USER's skin, implanted in the USER, removably coupled to the USER, or in any other manner caused to provide a pain management treatment to the USER (e.g., configured to administer the pain management treatment remotely).

In some embodiments, the system 100 can further comprise a control unit 115. In some embodiments, the control unit 115 can comprise a patient monitoring unit 120 and a prescription management unit 130. In some embodiments, the control unit 115 can be housed in a single device or apparatus. The control unit 115 can include or comprise one or more of a smart home device, a smart phone, a desktop computer, a laptop computer, a tablet, an Internet-of-things (IoT) device, a wearable device, a connected medication management unit, a patient portal, combinations thereof, and/or the like.

In some embodiments, the patient monitoring unit 120 can be configured to monitor, measure, receive, store, and/or transmit biometric characteristics 122 associated with the USER. The patient monitoring unit 120 can be configured to iteratively, discretely, or continuously, observe the user and measure, monitor, estimate, calculate, interpolate, or otherwise determine biometric characteristics about the user. In some embodiments, as described in further detail below, the patient monitoring unit 120 can comprise one or more of a camera, a sensor, a meter, an instrument, a detection unit, a biosensing device, a biomonitoring device, a biometric monitor, or the like. In some embodiments, the biometric characteristics 122 associated with the USER, as described in further detail below, can be used to monitor and/or measure a pain tolerance metric or a pain threshold metric of the USER, which can refer to a magnitude or degree of pain felt by the USER or a maximum amount of pain that can be tolerated by the USER without pain management intervention. In some embodiments, the biometric characteristics 122 can comprise one or more of a heart rate, a vocal scan, a gait, a posture, a blood pressure, a core body temperature, a respiration rate, a perspiration rate, facial expressions, iris characteristics, a blink rate, user-provided responses to questions regarding a user's pain tolerance, or the like. In some embodiments, the patient monitoring unit 120 can be configured to monitor, observe, or otherwise sense the biometric characteristics 122 of the USER either continuously or in a discrete manner. In some embodiments, the patient monitoring unit 120 can be configured to transmit the biometric characteristics 122 of the USER to the prescription management unit 130. In some embodiments, the prescription management unit 130 can be stored in the same apparatus, device, sub-process, sub-system, or the like as the patient monitoring unit 120.

More particularly, in some embodiments, the patient monitoring unit 120 can be configured to accurately determining a pain tolerance or a pain threshold for a patient remotely. In some embodiments, the patient monitoring unit 120 can comprise one or more processors (not shown) and one or more memory (not shown) storing computer program code. In some embodiments, the patient monitoring unit 120 can be configured to iteratively, discretely, or continuously, observe the user and measure, monitor, estimate, calculate, interpolate, or otherwise determine biometric, biological, medical, or other suitable characteristics about the patient (e.g., some or all of which may form a basis of the biometric characteristics 122). In some embodiments, the patient monitoring unit 120 can determine the patient's current pain tolerance or pain threshold based on at least the biometric, biological, medical, or other suitable characteristics. In some embodiments, the patient monitoring unit 120 can comprise a display (not shown) and a user interface (not shown) configured to allow for the patient to interact with an application, program, browser, or the like stored on and/or hosted by the patient monitoring unit 120. In some embodiments, the patient may provide feedback about their current pain tolerance or pain threshold at certain intervals, e.g., regularly, irregularly, when they perceive a change in their pain tolerance or pain threshold, and/or the like. In some embodiments, the patient monitoring unit 120 can include one or more sensors, one or more camera devices, one or more keyboards, one or more touchscreens or other such interactive input devices, and/or the like.

In some embodiments, the patient monitoring unit 120 can be or be hosted on or provided by the user device 105 or control device 115. In some embodiments, the patient monitoring unit 120, user device 105, and/or control device 115 can be configured to, comprise, or be in operable communication with one or more devices configured to, detect, measure, determine, monitor, evaluate, sense, calculate, estimate, or otherwise provide for generation or provision of the patient behavior information and/or the one or more biometric characteristics 122 of the USER. In some embodiments, the patient monitoring unit 120, user device 105, and/or control device 115 may comprise or be in operable communication with one or more cameras configured to capture images or video of the USER, a portion of the USER, a face of the USER, a portion of the face of the USER, and/or the like. In some embodiments, the patient monitoring unit 120, user device 105, and/or control device 115 may comprise or be in operable communication with one or more sensors configured to detect, measure, calculate, or estimate a gait of the patient, a posture of the patient, a stride distance of the patient, a step count of the patient, a stance of the patient, an activity level of the patient, an activity type of the patient, a motor function or range of a limb of the patient, and/or the like. In some embodiments, the patient monitoring unit 120, user device 105, and/or control device 115 may comprise or be in operable communication with one or more microphones configured to capture audio associated with a patient, vocal audio of the patient, non-verbal sounds associated with the patient, and/or the like. In some embodiments, the patient monitoring unit 120, user device 105, and/or control device 115 may comprise or be in operable communication with one or more other devices or apparatuses configured to detect, determine, monitor, measure, calculate, estimate, evaluate, or sense a biometric, physiological, psychological, psychiatric, medical, physical, emotional, mental, kinesthetic, motor-functional, and/or social condition of a patient, such as the patient's heart rate, blood pressure, body temperature, glucose level, adherence to a medical prescription plan, and/or the like. In some embodiments, the patient monitoring unit 120, user device 105, and/or control device 115 may be configured to capture, store, provide, and/or evaluate the images, image data, video, video data, audio, audio data, sensor data, biometric data, patient behavior data, patient activity data, patient social information, patient medical data, patient biometric data, patient physiological data, patient psychological data, patient psychiatric data, patient physical data, patient emotion data, patient mental data, patient kinesthetic data, patient motor-functional data, and/or the like. In some embodiments, the patient monitoring unit 120, user device 105, and/or control device 115 may be configured to process, analyze, or otherwise evaluate any of the disclosed information, data, images, image data, video, video data, audio, audio data, and/or the like, such as by using image processing circuitry, image processing software, an image processing program, audio processing circuitry, audio processing software, an audio processing program, video processing circuitry, video processing software, a video processing program, a computer entity configured to store and/or evaluate such information and data, an apparatus comprising one or more processors and one or more memory storing computer program instructions for storing and processing such information data and/or the like. In some embodiments, such as when one of the patient monitoring unit 120, user device 105, and/or control device 115 comprises a camera and is configured to capture images or video of a patient's face, the system 100 can further comprise a processor configured to carry out an algorithm, a computer program, computer-implemented instructions, a machine learning algorithm, a neural network, an artificial intelligence program, or the like to analyze one or more of the images of the patient's face to identify changes in the patient's facial expressions and to assign a pain tolerance level or a pain threshold level to the patient at a particular point in time based upon at least said changes in the facial expressions of the patient between a previous point in time and that particular point in time.

In some embodiments, one of the patient monitoring unit 120, user device 105, and/or control device 115 can be configured to capture images of the face of the USER or video of the face of the USER, and then, using a facial expression analysis technique, determine changes in the USER's pain tolerance or pain threshold. In some embodiments, the analysis of images/video for determining pain tolerance can be carried out remotely, in an automated manner, by a device (e.g., user device 105) registered in the system 100 by the USER, in the 'background', and/or 'passively'. This analysis, e.g., of the facial expressions, vocal changes, speech pattern changes, posture/gait changes, medical/biometric changes, and/or the like can be accounted for or considered as part of the dynamic prescription. In some embodiments, by using remote pain tolerance/threshold analysis to drive changes in a dosage of a medication or pain management treatment for the USER, the system 100 can be carried out, at least in part, remotely and within the bounds of the dynamic prescription. In some embodiments, when a change in the USER's pain threshold/tolerance level is determined to call for or require a change in the dosage of a pain management treatment that is determined to be outside the range allowed under the dynamic prescription, the request for a new dosage can be escalated to the PROVIDER for their authorization. In some embodiments, a user device 105 or the like can comprise specialized hardware and associated computer program(s) for capturing, detecting, sensing, monitoring, measuring, calculating, and/or estimating images, video, audio, information, or data associated with the USER, for storing/providing/receiving/transmitting such images, video, audio, information, or data, and for carrying out analysis such as predictive analysis by an artificial intelligence program using an algorithm or the like, to calculate, estimate, predict, evaluate, monitor, or otherwise determine a pain tolerance/threshold level of the USER. In some embodiments, the analysis can be carried out locally, remotely, in a distributed manner, in a centralized manner, using one or more processing circuitry, using one or more computing entities, using one or more cloud computing entities, using one or more specialized analysis devices such as audio processing circuitry, video processing circuitry, image processing circuitry, and/or the like. In some embodiments, the patient monitoring unit 120, user device 105, and/or control unit 115 can be configured to capture, e.g., using a camera, or receive from a device comprising or operating a camera, images and/or video of the USER's face and associated image data and/or video data, can be configured to transmit, store, or receive such images/video and associated image/video data, can be configured to analyze, e.g., by implementing an artificial intelligence program and/or an algorithm or the like, the images/video and associated image data/video data to determine based upon, e.g., changes in the USER's facial expressions, positioning in facial landmarks, relative orientation/position/size of facial features, change in a pupil or an iris of the USER, changes in the form factor, shape, configuration, orientation, position, location, and/or dimensions of the USER's mouth, eyes, eyebrows, chin, and/or the like, and to correlate such facial features, changes in facial features, expressions associated with facial features, and/or changes in expressions associated with facial features, e.g., according to PSPI analysis or the like, to track the USER's pain tolerance or paint threshold over time. In some embodiments, the USER's gait, posture, step count, step distance, speech patterns, and/or the like can be analyzed according to a similar or different manner or approach to determine changes in the USER's pain tolerance/pain threshold level(s). In some embodiments, sensors/devices/equipment such as described herein can be used to capture signals, information, images, and/or data associated with biometric characteristics of the USER, the user device 105, patient monitoring unit 120, and/or the control unit 115 can be configured to or used to analyze the signals, information, images and/or data to correlate a particular biometric characteristic with a current pain tolerance/threshold of the USER, e.g., using a program such as an artificial intelligence program or deep learning program, using an algorithm, using a machine learning algorithm, using a neural network, using any suitable model or other such program, and/or the like to predict the USER's current pain tolerance/threshold level based upon one or more of these biometric characteristics and changes thereof over time.

In some embodiments, the patient monitoring unit 120 can include one or more activity monitoring devices or healthcare monitoring devices, such as but not limited to: a gyroscope, a magnetometer, an accelerometer (e.g., a 3-axis accelerometer), a geospatial positioning system, a barometer, an altimeter, a step counter, a blood pressure monitor, a heart rate monitor, a respiration monitor, ambient pressure sensor, ambient temperature sensor, ambient oxygen sensor, an electrocardiogram device, an electroencephalogram device, skin temperature sensor, a myocardial sensor, a blood oxygen sensor, a elastomeric plethysmography (EP) device (e.g., one or more piezoelectric sensors on an elastic band for elastomeric plethysmography via current variation), an impedance plethysmography (IP) device, a respiratory inductive plethysmography (RIP) device, a photoplethysmography (PPG) device configured to measure blood oxygen saturation using pulse oximetry principles by measuring two adjacent peaks in a blood vessel variation waveform, a continuous glucose monitoring (CGM) device, or the like. In some embodiments, the patient monitoring unit 120 can include one or more speakers and/or one or more microphones. In some embodiments, the patient monitoring unit 120 can be configured to monitor, measure, calculate, estimate, sense, observe, interpret, derive, or otherwise determine one or more biometric, biological, medical, or movement characteristics of the patient and the chance over time thereof, such as but not limited to: facial feature, facial expressions, facial micro-expressions, gait, heart rate, heart rate variability, heart rate irregularity, incidents of a fall experienced by the patient, step count, step pace, blood pressure, respiration rate, eye movements, blink rate, pupil dilation, vocal/speech pattern, speech pace, incidents of slurred speech, posture, perspiration rate, breathing rate, sudden reduction or loss of hearing (e.g., if a patient suddenly increases the speaker volume on the patient monitoring unit 120 when interacting with the patient monitoring unit 120), dermal and subdermal perfusion rates, time spent sitting versus standing, limb and trunk movement and range of motion, sleep duration and sleep type patterns, combinations thereof, and/or the like. In some embodiments, the patient monitoring unit 120 can capture a patient's facial expressions when they are using the device, e.g., by using the front facing camera on a smart phone, and implement a facial action coding system (FACS) in conjunction with Prkachin Solomon Pain Intensity (PSPI) analysis to track pain tolerance or pain threshold changes in the patient. In some embodiments, the patient monitoring unit 120 can use an algorithm, neural network, machine learning model, and/or the like to determine changes in the patient's pain tolerance or pain threshold.

The prescription management unit 130 can be configured to review the USER's biometric characteristics 122 and to determine whether the initial prescription 112 is sufficient to reduce or eliminate the USER's pain based on changes in the USER's pain tolerance or pain threshold, which can be determined based on at least the biometric characteristics 122. The prescription management unit 130 can also be configured to determine when a change in the dosage of the initial prescription 112 is necessary based on changes in the biometric characteristics 122 associated with the USER. In an instance in which the prescription management unit determines that a change in the dosage of the pain management treatment is needed, based at least upon changes in the biometric characteristics 122, the prescription management unit 130 may a) determine that the change in dosage of the pain management treatment is automatically approved based upon some initial instructions regarding a change tolerance or margin about the initial dosage that the prescription management unit 130 is instructed to automatically authorize, b) determine that the dosage change is an errant dosage change based upon the magnitude of the change relative to the dosage of the initial prescription 112 and request further biometric characteristics 122 be provided from the patient monitoring unit 120, or c) determine that a change in dosage of pain management treatment is needed but that it falls outside of any provided change tolerance or margin relative to the initial dosage and request authorization for the updated dosage from the PROVIDER or a provider device (e.g., 140).

In some embodiments, the prescription management unit 130 can be configured to receive the biometric characteristics 122 associated with the USER and compare the biometric characteristics 122 to historical biometric data (not shown, e.g., stored at or received by the patient monitoring unit 120 or the prescription management unit 130) associated with the USER. In some embodiments, once the prescription management unit 130 compares the biometric characteristics to historical biometric data to measure, estimate, or calculate a change in the pain tolerance metric or the pain threshold metric.

In some embodiments, the prescription management unit 130 may compare the USER's historical biometric data at the time that the initial prescription 112 was created or received by the epidermal treatment device 110 to the biometric characteristics 122 received by the prescription management unit 130 to determine if the dosage associated with the initial prescription 112 is sufficient to manage or reduce the USER's new pain tolerance metric or new pain threshold metric, or whether a new dosage of the pain management treatment is necessary. Said otherwise, in some embodiments, the dosage of pain management treatment administered to the USER may be associated with a range of pain tolerance metric values or a range of pain threshold metric values, and the prescription management unit 130 may be configured to determine if a change in the pain tolerance metric or the pain threshold metric constitutes a change outside the range of one of these metrics that is associated with the dosage of pain management treatment administered by the epidermal treatment device 110 according to the initial prescription 112.

In some embodiments, in an instance in which the prescription management unit 130 determines that a change in the dosage of pain management treatment is needed due to a change in the USER's pain tolerance metric or pain threshold metric, the prescription management unit 130 can be configured to determine the new dosage of the pain management treatment that is necessitated to manage or reduce the USER's new pain tolerance metric or pain threshold metric. In some embodiments, the prescription management unit 130 can communicate the new dosage to the user device 105 in order for the epidermal treatment device 110 to administer the new dosage of the pain management treatment. In some embodiments, the updated prescription 132 can be generated by, received by, and/or transmitted by the prescription management unit 130 to the epidermal treatment device, in some cases by way of the patient monitoring unit 120, and in other cases by direct wired or wireless communication with the epidermal treatment device 110.

In some embodiments, when the prescription management unit 130 determines that a change in the USER's pain tolerance metric or pain threshold metric warrants a change in the dosage of the pain management treatment administered to the USER, the prescription management unit 130 may create or cause creation of an updated prescription 132 that comprises or conveys the new dosage required to sufficiently reduce or manage the USER's pain. In some embodiments, to determine if the change in the USER's biometric characteristics 122 warrants the creation of the updated prescription 132, the prescription management unit 130 may communicate with a provider device 140 that is operated by or in operable communication with a PROVIDER associated with the USER, the PROVIDER being an entity that provided or authorized the initial prescription 112. In some embodiments, the provider device 140 can comprise a prescription authorization unit 150 that is configured to store one or more dynamic prescriptions 152, e.g., associated with the USER for the particular pain management treatment administered by the epidermal treatment device 110. In some embodiments, the provider device 140 can comprise one or more processors (not shown) and one or more memory devices (not shown) that can be configured to carry out one or more computer-implemented methods or algorithms to compare the updated prescription 132 to the dynamic prescription 152. In some embodiments, a dynamic prescription 152 can comprise a set dosage ranges, USER biometric data, temporal conditions, if/then statements, conditional statements, or the like that can be used to determine if the new dosage associated with the updated prescription 132 is appropriate for administering the pain management treatment to the USER based upon the historical biometric data of the USER, the initial prescription 112, the biometric characteristics 122, the updated prescription 132, and/or the dynamic prescription 152.

In some embodiments, the dynamic prescription 152 can be developed based upon provider-provided and/or patient-provided data such as electronic health records, individual health records, international or domestic health regulations, provider management systems, patient preferences, the patient's insurance details, the patient's historical biometric data, historical biological data, historical medical records, and the like. The dynamic prescription 152 can comprise a set of 'if/then' elements or the like that the prescription authorization unit is configured to answer in a particular order. In some embodiments, the dynamic prescription 152 can include an initial question or initial set of questions that relate, for instance, to a change in the patient's pain tolerance or pain threshold. In some embodiments, the dynamic prescription 152 can include subsequent questions or set of questions that relate, for instance, to a provider-provide limit on the dosage of the pain management treatment that considers the patient's biometric, biological, medical, or other characteristics or data (e.g., the patient's heart rate, blood pressure, gait, or the like). In some embodiments, the dynamic prescription 152 can also include a question or a set of questions related to domestic or international regulations related to what and how much pain management treatments can be administered/changed remotely, absolute or relative dosage limits, and/or the like. In some embodiments, the dynamic prescription 152 can include a question or a set of questions related to past changes in the dosage, the rate and magnitude of such changes, the remaining supply of pain medication (when applicable), and/or the like. Said otherwise, the dynamic prescription 152, instead of providing a static dosage, can provide a dosage range that changes in response to changes in a patient's pain tolerance or pain threshold, accounting for medical or legal limits placed on dosage changes that are specific to the pain management treatment, jurisdiction, provider, application type, patient, provider, and/or the like. The dynamic prescription 152 can be pre-authorized by the provider. In some embodiments, when the prescription management unit determines that the change in dosage of pain management treatment is needed but that it falls outside of any provided change tolerance or margin relative to the initial dosage, the prescription management unit may transmit a request for authorization of the updated dosage of the updated prescription to the prescription authorization unit. The prescription authorization unit can then review the request for the updated dosage of the updated prescription, e.g., by answering the questions related to the dynamic prescription to determine if the dynamic prescription 152 authorizes the updated dosage for the patient, and then a) automatically provides authorization for the updated prescription to the prescription management unit, b) automatically rejects the updated prescription (e.g., when the dosage change is suspected to be in error, when the dosage change would contravene a law, and/or the like), or c) requests approval for the updated prescription from the provider. In some embodiments, the prescription authorization unit can cause a notification, alert, message, request, or the like to be pushed to, displayed on, sent to, or otherwise provided to a provider device such as a computer, beeper, mobile phone, smart phone, tablet, or the like. The provider can then review the updated prescription and can instruct the prescription authorization unit to either allow or disallow the updated prescription, can mark the updated prescription as being a suspected errant request, can communicate with the patient/user to provide telemedical care or request that the patient/user visits the provider's office, amend the dynamic prescription 152 based upon the updated prescription request, and/or the like. In an instance in which the prescription authorization unit or prescription management unit automatically authorizes the updated prescription, or in an instance in which the provider manually authorizes the updated prescription, the prescription management unit can communicate with either the patient monitoring unit or the epidermal treatment device to provide the updated prescription along with authorization for the epidermal treatment device to administer the pain management treatment to the user according to the updated prescription. The epidermal treatment device can then replace the initial prescription with the updated prescription and comply with the specific dosage/timing requirements of the updated prescription in administering the pain management treatment to the user.

In some embodiments, the dynamic prescription 152 can be developed by determining the internet-of-things (IoT) devices and sensors available for a patient and the device and sensor boundaries with respect to particular biological indicators or characteristics. The USER's current pain threshold/pain tolerance can then be established and the USER's current pain threshold/pain tolerance can be associated with the biometric characteristics 122. Then, the dosage of the initial prescription 112 can be determined and associated with the USER's current pain threshold/pain tolerance and biometric characteristics 122. The PROVIDER can then establish or define an outside dosage range indicating a magnitude of increase of the dosage and a magnitude of decrease of the dosage that are allowed for the USER. The PROVIDER can then establish, define, or provide a set of conditions in which the current dosage of the pain management treatment can be changed, within the outside dosage range.

As an initial non-limiting example, the PROVIDER may indicate that if the USER's pain tolerance increases to above 9/10 AND the USER belongs to a certain demographic group or area AND if the USER's age is within a particular age range, then the current dosage can be increased to an updated dosage higher than the current dosage for a particular time period, e.g., before re-analyzing patient pain tolerance/pain threshold or reverting back to the current dosage lower than the updated dosage.

As a subsequent non-limiting example, the PROVIDER may indicate that if the USER's pain tolerance/pain threshold reduces by more than a threshold reduction in pain tolerance/pain threshold AND the USER belongs to a certain demographic area OR if one or more of the biometric characteristics 122 are within a predetermined range considered to be suitable for a reduction in dosage, then the current dosage can be decreased to an updated dosage lower than the current dosage for a particular time period, e.g., before re-analyzing patient pain tolerance/pain threshold or reverting back to the current dosage higher than the updated dosage.

As a further non-limiting example, the USER may have a wearable device (e.g., the epidermal treatment device 110 or different from the epidermal treatment device 110) that sends a signal to a provider management system (e.g., the prescription authorization unit 150); for example the USER may be a cardiology patient taking statins that is determined to be involved in excessive/out-of-normal physical activity, causing a drop in blood sugar level, which may necessitate a reduction in the dosage of a remotely administered diabetes medication for a particular time period.

As yet another non-limiting example, the USER may be an oncology patient to whom a medication is being administered remotely according to any of the processes or methods described herein, and the PROVIDER may code the dynamic prescription 152 for the USER that indicates, if the USER is exposed to conditions that are not optimal in view of their medical condition and medication being administered AND/OR if the USER is in a particular demographic group (e.g., a particular sex, race, nationality, geographic location, employment type, or any other suitable group of patients) AND/OR if the USER has an age that is within a particular predetermined age range AND/OR if the USER received their last oncology treatment (e.g., radiation therapy, chemotherapy, and/or the like) within a predetermined window preceding the date and time of analysis, then the dynamic prescription 152 can automatically instruct the PROVIDER, USER, epidermal treatment device 110, or the like to increase the dosage of the pain management treatment for a predetermined time period.

In some embodiments, in order for the PROVIDER to "code" the dynamic prescription via digital means within a provider management system, there may be an "INPUT" which needs to be "ANALYZED" before coding the prescription. For example, an "INPUT" may include without limitation one or more of (a) information related to the sensors or IoT devices that the USER has registered and/or that are in communication with the apparatus or system establishing or otherwise managing the dynamic prescription 152, (b) capabilities and configurations for the various sensors or IoT devices, either derived from the respective sensor/IoT device, culled from the above-mentioned information, or provided by or retrieved from a third party, (c) a summary of edge computing capabilities for each IoT device, (d) capabilities and configurations for each "coordinating device," such as a smart watch, smart home sensor, vehicle sensor, or the like, that coordinates multiple IoT devices, (e) hierarchy of sensors/IoT devices with regard to channels of communication and the configurations required for data collation and transmission from each of these devices, (f) information related to the interoperability of the various sensors/IoT devices the USER has registered, (g) information related to alternative hierarchies or channels of communication if one or more of the sensors/IoT devices that the USER has registered becomes unreachable or is suspected of being corrupted or providing erroneous data, and/or (h) other suitable information helpful or necessary for the establishment of a stable channel of communication between and within the network and the sensors/IoT devices such that the dynamic prescription 152 can be generated, maintained, and/or updated based upon inputs from the PROVIDER as well as feedback and data provided by the USER, the patient monitoring unit 120, the prescription management unit 130, and/or the various sensors/IoT devices.

In some embodiments, in order to initially code the dynamic prescription 152 for the USER, in addition to or alternative to the approach and process elements described above, the process can include presenting the PROVIDER with the available "INPUTS" and allowing the PROVIDER to choose the appropriate collection of sensors/IoT devices that are appropriate for considering with regard to the dynamic prescription 152. The PROVIDER can then indicate or code in the dynamic prescription 152 (which may for instance be carried out by selecting among a drop-down list or conducting a search) the appropriate biological indicators, patient movement data, healthcare metrics, and/or environmental data (e.g., biometric characteristics 122) that should be considered from among the data received from the collection of approved sensors/IoT devices the USER has registered. The PROVIDER can then identify, for each sensor or IoT device and/or for each type of feedback or data, the expected range or value, optionally one or more secondary indicators or considerations that should be considered in such an instance, and a dosage change that should be carried out in such an instance. For example, for a USER has registered a heart rate monitor, the PROVIDER can code a particular heart rate range that is expected for the USER, such that if/when the heart rate monitor returns a heart rate outside the PROVIDER-indicated expected range of heart rates, the dynamic prescription 152 can increase or decrease the dosage based on such an indication.

When coding the dynamic prescription 152, the PROVIDER may select a particular frequency or a particular time frame and iteration count for any or all of the analyses being done remotely to determine the USER's pain tolerance or pain threshold, and/or can indicate how the dosage should change based upon changes in the respective analyses. The PROVIDER may also indicate the duration of pain management treatment and/or can indicate one or more stages of pain management treatment (e.g., through a staged weaning period). When coding the dynamic prescription 152, the PROVIDER may select a particular activity or group of activities to indicate how the prescription changes based on a particular input, such as information related to the initial cause of pain, the intensiveness of any preceding surgeries or inpatient/outpatient treatments, how many calories the patient has consumed or burned, the number of stiches the patient received following a surgery, or any other suitable input. When coding the dynamic prescription 152, the PROVIDER may select one or more user contexts, such as the demographic information of the patient, to consider when dynamically changing the prescription. When coding the dynamic prescription 152, the PROVIDER may select one or more environmental conditions or changes to consider when dynamically changing the prescription, such environmental conditions or changes including but not limited to exposure to contaminants or harsh environmental conditions, the frequency and/or type of human interaction the USER has (e.g., by tracking emails, SMS texts, phone calls, or the like for a period of time following a surgery), the USER's social media accounts and their interactions with others on these social media platforms, application programming interface (API) calls to the weather system or a third-party weather service, temperature sensor readings, barometric pressure sensor readings, patient activity/motion data, and/or the like. When coding the dynamic prescription 152, the PROVIDER may select a prescription renewal time, e.g., by analyzing the consumption rate of the drug, and authorize the dynamic prescription 152 and/or associated machine learning algorithm or artificial intelligence program carrying out the dynamic prescription 152 to suggest changes or pre-authorize changes only at particular times or with a consideration for the remaining stock of a drug that the patient has on hand.

In some embodiments, when the dynamic prescription 152 is updated and/or when their effective dosage is changed according to the dynamic prescription 152, the USER may be notified through push notification from an application, email, phone call, SMS text message, or the like regarding the change in their prescription or effective dosage. In some embodiments, when the dynamic prescription 152 is updated and/or when their effective dosage is changed according to the dynamic prescription 152, the USER may be asked to authorize the change in their prescription or effective dosage. In some embodiments, when the dynamic prescription 152 is updated and/or when their effective dosage is changed according to the dynamic prescription 152, the USER may be notified regarding the change in their prescription or effective dosage and given an opportunity to temporarily stop the change in their prescription or effective dosage until the PROVIDER has reviewed the change and has authorized the change. In some embodiments, the USER may be notified regarding the change in their prescription or effective dosage only when the dynamic prescription 152 and/or associated machine learning algorithm or artificial intelligence program carrying out the dynamic prescription 152 determines that the calculated necessary dosage change is outside the range preauthorized under the dynamic prescription 152, elevates the request for a dosage change to the PROVIDER, and the PROVIDER authorizes the change, e.g., to the dosage and/or to the dynamic prescription 152.

In some embodiments, the dynamic prescription 152 and/or an associated machine learning algorithm or artificial intelligence program carrying out the dynamic prescription 152 can track and/or request updates from the USER's sensors/IoT devices regarding the quantity of a remaining stock of the USER's medication. In some embodiments, in an instance in which the dynamic prescription 152 and/or the associated machine learning algorithm or artificial intelligence program carrying out the dynamic prescription 152 determine that a change in the dosage will unduly diminish the quantity of the remaining stock of the USER's medication, and/or will result in a depletion of the USER's medication before such a time as the USER is scheduled (or legally allowed) to replenish their stock of the medication, can take these competing challenges and interests into account when determining a necessary change in the dosage of the USER's medication and/or can disallow changes to the dosage administered in order to maintain sufficient stock so that the USER does not run out of their medication before they receive a replenishing supply. In some embodiments, the dynamic prescription 152 and/or the associated machine learning algorithm or artificial intelligence program carrying out the dynamic prescription 152, upon determining that the USER's stock of a medication is low or that a change made to their dosage will result in a more rapid diminishment of the USER's stock of the medication, can provide an alert to the prescription authorization unit 150 or a device of the PROVIDER such that the PROVIDER can coordinate providing the USER with a replenishing supply of their medication, amend the USER's plan of care with regard to the time horizon for administering the medication, contravene the dosage change, and/or contact the USER for follow-up telemedical care.

While in some embodiments, such as illustrated in FIG. 1A the epidermal treatment device 110 is part of a separate device (e.g., the user device 105) than that which stores and/or hosts the patient monitoring unit 120, in other embodiments, both the epidermal treatment device 110 and the patient monitoring unit 120 can be stored on the same device (as illustrated in FIG. 1B). Likewise, while the patient monitoring unit 120 and the prescription management unit 130 are illustrated in FIGS. 1A and 1B as being part of the same device (the control unit 115 and the user device 105, respectively), in other embodiments, the patient monitoring unit 120 and the prescription management unit 130 can be stored on different devices (e.g., in FIG. 1C, in which the patient monitoring unit 120 is stored and/or hosted on the user device 105 while the prescription management unit 130 is stored and/or hosted on the provider device 140). Furthermore, while FIGS. 1A-1C illustrate the user device 105 as including the epidermal treatment device 110, the user device 105 can include instead an embedded treatment device (not shown), an implanted treatment device (not shown), or any other suitable treatment device that is configured to provide a pain management treatment to the USER. While the system 100 illustrated in FIGS. 1A-1C is illustrated as including the user device 105 and no other user devices, one of ordinary skill in the art will understand that the control unit 115 can be owned by, operated by, under the control of, and/or communicate most typically with the USER. However, one of ordinary skill in the art will further understand, especially given the discussion herein regarding the various sensors and IoT devices that the USER can register with the provider device 140 or other systems/networks of the PROVIDER, that the system 100 can comprise many and multiple other devices, units, components, sub-systems, apparatuses, and/or the like, e.g., as part of the patient monitoring unit 120 or in communication with the patient monitoring unit 120.

Exemplary Treatment Devices

FIGS. 2A and 2B provide a top view and a side view of a treatment device 210 which can be substantially similar in form and/or function as the epidermal treatment device 110 described hereinabove. FIG. 2C illustrates at least some of the possible locations for placement of the treatment device 210 on a user 220. In some embodiments, the treatment device 210 can comprise an adhesive portion 214, a treatment delivery portion 216, and a communications element 218 configured to store the initial prescription 112 and configured to communicate with one or more components or elements of the remote pain treatment system (e.g., which can be substantially similar in form and/or function to the system 100 described hereinabove). In some embodiments, the treatment device 210 can be configured to be removably coupled to the skin of the user 220. In some embodiments, the adhesive portion 216 can comprise a fabric or the like with an applied adhesive material configured to retain the treatment device 210 on the user's 220 skin for the desired duration of treatment. Any suitable fabric or other material can be used for the adhesive portion 216, and many possible fabrics or other materials will be readily known to one of ordinary skill in the art. Likewise, any suitable adhesive material can be used on the adhesive portion 216 of the treatment device 210 to retain the treatment device 210 on the skin of the user 220, and many possible adhesive materials will be readily known to one of ordinary skill in the art.

In some embodiments, the treatment delivery portion 216 can comprise a medication storing material that is configured to store a volume of a medication. In some embodiments, the treatment delivery portion 216 can comprise a reservoir for storing a stock of the medication. In some embodiments, the treatment delivery portion 216 can comprise a delivery mechanism configured to communicate a particular volume of the medication from the reservoir or from the medication storing material to the skin of the user 220. In some embodiments, the delivery mechanism can include a simple interface between an underside of the treatment delivery portion 216 that is configured to directly abut the skin of the user 220 such that the skin of the user 220 is exposed to a controlled volume or volume rate of the medication that is delivered to the simple interface, and the medication is absorbed by the skin for metabolization by the user 220. In some embodiments, the treatment delivery portion 216 can comprise a port (not shown), a needle (not shown), or the like for non-dermal introduction of the medication into the user 220.

In some embodiments, the communications element 218 can be configured to communicate with one or more of a control device 230a or 230b, which can be substantially similar in form and/or function to the control device 115, the patient monitoring unit 120, and/or the prescription management unit 130 described hereinabove. In some embodiments, the communications element 218 can be configured to communication with a provider device 240, which can be substantially similar in form and/or function to the provider device 140 described hereinabove. Without wishing to be bound by any particular theory, the communications element 218 can be configured to communicate via any of the methods, protocols, signals, approaches, or technologies described herein, such as WiFi, Bluetooth, infrared radiation (IR) signal transmissions, radio frequency identification (RFID) communications, near-field communication (NFC), radio frequency signal transmissions, narrow-band IoT communications, GSM, GPRS, CDMA, EDGE, LTE, third generation (3G) spectrum, fourth generation (4G) spectrum, fifth generation (5G) network(s), other wireless and satellite telecommunications approaches, and any other suitable spectrums, frequencies, protocols, bands, and/or the like.

In some embodiments, the rate at which the medication is communicated from the medication storing material or the reservoir to the skin of the user 220 or otherwise into the user 220 can be controlled by changing an outflow rate of medication from the medication storing material or the reservoir. In some embodiments, the outflow rate of medication from the medication storing material or the reservoir can be changed or otherwise monitored/controlled by the communications element 218, which can be configured to receive and store the initial prescription 112 or the updated prescription 132, e.g., from the prescription management unit 130 or the like. In some embodiments, the communications element 218 can refer to dosage instructions provided in or with the initial prescription 112 or the updated prescription 132 in order to determine, for the particular treatment device 210 being used by the user 220, the appropriate outflow rate from the medication storing material or the reservoir. In some embodiments, the communications element 218 is also configured to determine and/or monitor the remaining stock of medication in the medication storing material or the reservoir. In some embodiments, the communications element 218 is also configured to receive, e.g., from the control device 230a/230b or the provider device 240, the updated prescription 132, determine a dosage change by comparing the dosage associated with the updated prescription 132 to the dosage associated with the initial prescription 112, and adjusting the outflow from the medication storing material or the reservoir accordingly to achieve the new dosage associated with the updated prescription 132. In some embodiments, the communications element 218 can communicate a confirmation of the updated prescription 132, and/or a confirmation that the treatment device 210 will adhere to the dosage instructions of the updated prescription 132, to the control device 230a/230b or the provider device 240. In some embodiments, the communications element 218 can communicate, with a confirmation such as describe above, a status of the remaining medication in the medication storing material or the reservoir.

FIGS. 3A-3C provide, respectively, a top view, a bottom view, and a side view of a treatment device 310 which can be substantially similar in form and/or function as the epidermal treatment device 110 described hereinabove. In some embodiments, the treatment device 310 can be or comprise a neuromodulation device, a repetitive transcranial magnetic stimulation device, a transcranial pulsed electromagnetic fields device a transcutaneous electrical nerve stimulation device, an electroconvulsive therapy device, an intrathecal drug delivery device, combinations thereof, and/or the like. FIG. 3D illustrates at least some of the possible locations for placement of the treatment device 310 on a user 320.

In some embodiments, the treatment device 310 can comprise an adhesive portion 314, a treatment delivery portion 316, and a communications element 218 configured to store the initial prescription 112 and configured to communicate with one or more components or elements of the remote pain treatment system (e.g., which can be substantially similar in form and/or function to the system 100 described hereinabove). In some embodiments, the treatment device 310 can be configured to be removably coupled to the skin of the user 320. In some embodiments, the adhesive portion 316 can comprise a fabric or the like with an applied adhesive material configured to retain the treatment device 310 on the user's 320 skin for the desired duration of treatment. Any suitable fabric or other material can be used for the adhesive portion 316, and many possible fabrics or other materials will be readily known to one of ordinary skill in the art. Likewise, any suitable adhesive material can be used on the adhesive portion 316 of the treatment device 310 to retain the treatment device 310 on the skin of the user 320, and many possible adhesive materials will be readily known to one of ordinary skill in the art.

In some embodiments, the treatment delivery portion 316 can comprise a plurality of stimulation elements 316a-316f that are configured to provide a stimulating treatment to the skin of the user 320. In some embodiments, the plurality of stimulation elements 316a-316f can be disposed on an underside of the treatment device 310 and configured to be in operable communication with and/or directly abutting the skin of the user 320 during operation of the treatment device 310. In some embodiments, the plurality of stimulation elements 316a-316f can be configured to communicate a dosage of a neuromodulation stimulus, electrical pulse, electromagnetic signal, magnetic field, acoustic signal, other suitable neurologically stimulating energies and fields, waveform variations thereof, frequency variations thereof, pulse rate variations thereof, combinations thereof, and/or the like to the skin of the user 320.

In some embodiments, the communications element 318 can be configured to communicate with one or more of a control device 330a or 330b, which can be substantially similar in form and/or function to the control device 115, the patient monitoring unit 120, and/or the prescription management unit 130 described hereinabove. In some embodiments, the communications element 318 can be configured to communication with a provider device 340, which can be substantially similar in form and/or function to the provider device 140 described hereinabove. Without wishing to be bound by any particular theory, the communications element 318 can be configured to communicate via any of the methods, protocols, signals, approaches, or technologies described herein, such as WiFi, Bluetooth, infrared radiation (IR) signal transmissions, radio frequency identification (RFID) communications, near-field communication (NFC), radio frequency signal transmissions, narrow-band IoT communications, GSM, GPRS, CDMA, EDGE, LTE, third generation (3G) spectrum, fourth generation (4G) spectrum, fifth generation (5G) network(s), other wireless and satellite telecommunications approaches, and any other suitable spectrums, frequencies, protocols, bands, and/or the like.

In some embodiments, the dosage of pain management treatment can be referred to as a stimulation dosage, which can be a function of one or more characteristics or settings of the treatment device 310 and/or the stimulation elements 316a-316f, including but not limited to current, frequency, magnitude, amplitude, waveform, voltage, electrostatic force, field, amperage, intensity, force, field, direction, vector, inductance, energy type, stimulation location, and/or the like. In some embodiments, the stimulation dosage can be controlled by the number and placement of the stimulation elements 316a-316f and/or the spacing therebetween. In some embodiments, the stimulation dosage can be used to moderate, normalize, or otherwise correct nervous tissue functioning in the user 320.

In some embodiments, the communications element 318 can be configured to control the stimulation dosage. In some embodiments, the communications element 218 can be configured to receive and store the initial prescription 112 or the updated prescription 132, e.g., from the prescription management unit 130 or the like. In some embodiments, the communications element 318 can refer to dosage instructions provided in or with the initial prescription 112 or the updated prescription 132 in order to determine, for the particular treatment device 310 being used by the user 320, the appropriate stimulation dosage. In some embodiments, the communications element 318 is also configured to determine and/or monitor a remaining potential stimulation energy stored by, for example, a battery (not shown) or the like electrochemical storage device configured to provide the energy required to carry out the stimulation. In some embodiments, the communications element 318 is also configured to receive, e.g., from the control device 330a/330b or the provider device 340, the updated prescription 132, determine a dosage change by comparing the dosage associated with the updated prescription 132 to the dosage associated with the initial prescription 112, and adjusting one or more settings of the treatment device 310 or a subcomponent thereof (e.g., the plurality of stimulation elements 316a-316f) to achieve the new dosage associated with the updated prescription 132. In some embodiments, the communications element 318 can communicate a confirmation of the updated prescription 132, and/or a confirmation that the treatment device 310 will adhere to the dosage instructions of the updated prescription 132, to the control device 330a/330b or the provider device 340. In some embodiments, the communications element 318 can communicate, with a confirmation such as describe above, a status of the remaining potential stimulation energy.

Exemplary Computing Entity

FIG. 4 provides a schematic of a computing entity 401 according to one embodiment of the present invention. In some embodiments, the computing entity 401 can be substantially similar in form and/or function to the user device 105, the epidermal treatment device 110, the control unit 115, the patient monitoring unit 120, the prescription management unit 130, the provider device 140, and/or the prescription authorization unit 150, or vice versa. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As shown in FIG. 4, in one embodiment, the computing entity 401 may include or be in communication with one or more processing elements 405 (also referred to as processors, processing circuitry, and/or similar terms used herein interchangeably) that communicate with other elements within the computing entity 401 via a bus, for example. As will be understood, the processing element 405 may be embodied in a number of different ways. For example, the processing element 405 may be embodied as one or more complex programmable logic devices (CPLDs), microprocessors, multi-core processors, coprocessing entities, application-specific instruction-set processors (ASIPs), microcontrollers, and/or controllers. Further, the processing element 405 may be embodied as one or more other processing devices or circuitry. The term circuitry may refer to an entirely hardware embodiment or a combination of hardware and computer program products. Thus, the processing element 405 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 405 may be configured for a particular use or configured to execute instructions stored in volatile or non-volatile media or otherwise accessible to the processing element 405. As such, whether configured by hardware or computer program products, or by a combination thereof, the processing element 405 may be capable of performing steps or operations according to embodiments of the present invention when configured accordingly.

In one embodiment, the computing entity 401 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 410, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the computing entity 401 may further include or be in communication with volatile media (also referred to as volatile storage, memory, memory storage, memory circuitry and/or similar terms used herein interchangeably). In one embodiment, the volatile storage or memory may also include one or more volatile storage or memory media 415, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 405. Thus, the databases, database instances, database management systems, data, applications, programs, program modules, scripts, source code, object code, byte code, compiled code, interpreted code, machine code, executable instructions, and/or the like may be used to control certain aspects of the operation of the computing entity 401 with the assistance of the processing element 405 and operating system.

In some embodiments, the computing entity 401 may also include one or more communications interfaces 420 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOC SIS), or any other wired transmission protocol. Similarly, the computing entity 401 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the computing entity 401 may include or be in communication with one or more input elements, such as a keyboard input, a mouse input, a touch screen/display input, motion input, movement input, audio input, pointing device input, joystick input, keypad input, and/or the like. The computing entity 401 may also include or be in communication with one or more output elements (not shown), such as audio output, video output, screen/display output, motion output, movement output, and/or the like.

Exemplary External Computing Entity

FIG. 5 provides an illustrative schematic representative of an external computing entity 501 that can be used in conjunction with embodiments of the present invention. In some embodiments, the external computing entity 501 can be substantially similar in form and/or function to the user device 105, the epidermal treatment device 110, the control unit 115, the patient monitoring unit 120, the prescription management unit 130, the provider device 140, and/or the prescription authorization unit 150, or vice versa. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 501 can be operated by various parties. As shown in FIG. 5, the external computing entity 501 can include an antenna 512, a transmitter 504 (e.g., radio), a receiver 506 (e.g., radio), and a processing element 508 (e.g., CPLDs, microprocessors, multi-core processors, coprocessing entities, ASIPs, microcontrollers, and/or controllers) that provides signals to and receives signals from the transmitter 504 and receiver 506, correspondingly.

The signals provided to and received from the transmitter 504 and the receiver 506, correspondingly, may include signaling information/data in accordance with air interface standards of applicable wireless systems. In this regard, the external computing entity 501 may be capable of operating with one or more air interface standards, communication protocols, modulation types, and access types. More particularly, the external computing entity 501 may operate in accordance with any of a number of wireless communication standards and protocols, such as those described above with regard to the computing entity 401. In a particular embodiment, the external computing entity 501 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 501 may operate in accordance with multiple wired communication standards and protocols, such as those described above with regard to the computing entity 401 via a network interface 520.

Via these communication standards and protocols, the external computing entity 501 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 501 can also download changes, add-ons, and updates, for instance, to its firmware, software (e.g., including executable instructions, applications, program modules), and operating system.

According to one embodiment, the external computing entity 501 may include location determining aspects, devices, modules, functionalities, and/or similar words used herein interchangeably. For example, the external computing entity 501 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 501 position in connection with a variety of other systems, including cellular towers, Wi-Fi access points, and/or the like. Similarly, the external computing entity 501 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 501 may also comprise a user interface (that can include a display 516 coupled to a processing element 508) and/or a user input interface (coupled to a processing element 508). For example, the user interface may be a user application, browser, user interface, and/or similar words used herein interchangeably executing on and/or accessible via the external computing entity 501 to interact with and/or cause display of information/data from the computing entity 401, as described herein. The user input interface can comprise any of a number of devices or interfaces allowing the external computing entity 501 to receive data, such as a keypad 518 (hard or soft), a touch display, voice/speech or motion interfaces, or other input device. In embodiments including a keypad 518, the keypad 518 can include (or cause display of) the conventional numeric (0-9) and related keys (#, *), and other keys used for operating the external computing entity 501 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 501 can also include volatile storage or memory 522 and/or non-volatile storage or memory 524, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 501. As indicated, this may include a user application that is resident on the entity or accessible through a browser or other user interface for communicating with the computing entity 501 and/or various other computing entities.

In another embodiment, the external computing entity 501 may include one or more components or functionality that are the same or similar to those of the computing entity 501, as described in greater detail above. As will be recognized, these architectures and descriptions are provided for exemplary purposes only and are not limiting to the various embodiments.

In various embodiments, the external computing entity 501 may be embodied as an artificial intelligence (AI) computing entity, such as an Amazon Echo, Amazon Echo Dot, Amazon Show, Google Home, and/or the like. Accordingly, the external computing entity 501 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include RAM, dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

FIG. 6 provides a block flow diagram of a process 600 for administering a pain management treatment remotely. The process 600 can comprise applying, once a patient comes out of a surgical procedure, a smart bandage such as a transdermal patch, at 601. The smart bandage can be enabled with a sensor, infused with a pain medication, and monitored/controlled by an IoT device, at 602. The doctor may code the prescribed dosage to be dispensed using the smart bandage, at 603. Then, if the patient has not provided any feedback, at 604, no adjustments are made and the patch is continually monitored for a defined period of time based on use conditions and patient/provider preferences, at 605. However, if the patient has provided feedback, at 604, then the process 600 can further comprise gathering patient reported outcomes, at 606, generating biometric markers of the patient, at 607, and compiling data from the patient's care plan and case management data, along with electronic medical record data and the like, at 608. Then, based upon the patient's data and records that were gathered, generated, and compiled in 606-608, if it is determined (e.g., using an artificial intelligence program to analyze the data and records) that there is a need to adjust the dosage prescribed to the patient, and/or if there is no need to notify the patient's physician of changes to the dosage, at 609, then the process 600 can further comprise continuing to systematically monitor and observe the patient with regard to the need for dosage changes, at 610. However, if it is determined (e.g., using an artificial intelligence program to analyze the data and records) that there is a need to adjust the dosage prescribed to the patient and that the patient's physician should be notified of changes to the dosage, at 609, then the process 600 can further comprise informing the physician and/or care specialist per the patient records system, of the recommended adjustments to the patient's dosage, at 611. The physician or care specialist can then approve the recommended adjustments to the patient's dosage and a message can be sent to the patient's application (e.g., on their smart phone that is in communication with the smart bandage) of the approval, at 612. The physician can then remotely administer or remotely cause administration of the dosage through the smart bandage, at 613. The smart bandage then modifies the dosage to comply with the updated prescription, as approved by the physician or care specialist, and the patient is monitored to determine if there are any adverse reactions to the new dosage and/or to determine if the new dosage is correct based on patient feedback, at 615. Once it is determined that, at least after a predetermined time period within which no negative symptomatic or pain threshold/pain tolerance feedback is received, the process 600 can be terminated for the time being while the patient is continuously monitored by the smart bandage and/or other components of the system, at 616.

FIG. 7 provides a block flow diagram of a process 700 for administering a pain management treatment remotely. The process 700 can comprise applying, installing, or implanting a neuromodulation device to a patient once the patient comes out of a surgical procedure, at 701. The neuromodulation device can then be connected to a hospital care system via an IoT network connection or by way of a patient device such as a smart phone or tablet device, at 702. The doctor then prescribes an application to the patient, using which the doctor can monitor the neuromodulation device remotely, at 703. Then, if the doctor or an artificial intelligence program, such as that described herein, determines the neuromodulation device does not need to be adjusted, at 704, e.g., based upon a sufficiently low patient pain threshold level or pain tolerance level, no adjustments are made to the neuromodulation device and the device is continuously monitored and allowed to continue operating according to the initial dosage of pain management treatment and the patient's plan of care, at 705. However, if the doctor or an artificial intelligence program, such as that described herein, determines the neuromodulation device does need to be adjusted, at 704, e.g., based upon an increased patient pain threshold level or pain tolerance level, the process 700 can further comprise gathering patient reported outcomes, at 706, generating biometric markers of the patient, at 707, and compiling data from the patient's care plan and case management data, along with electronic medical record data and the like, at 708. Then, based upon the patient's data and records that were gathered, generated, and compiled in 706-708, if it is determined (e.g., using an artificial intelligence program to analyze the data and records) that there is a need to adjust the dosage prescribed to the patient, and/or if there is no need to notify the patient's physician of changes to the dosage, at 709, then the process 700 can further comprise continuing to systematically monitor and observe the patient with regard to the need for dosage changes, at 710. However, if it is determined (e.g., using an artificial intelligence program to analyze the data and records) that there is a need to adjust the dosage prescribed to the patient and that the patient's physician needs to be notified of changes to the dosage, at 709, then the process 700 can further comprise informing the physician and/or care specialist per the patient records system, of the recommended adjustments to the patient's dosage, at 711. The physician or care specialist can then approve the recommended adjustments to the patient's dosage and a message can be sent to the patient's application (e.g., on their smart phone that is in communication with the neuromodulation device) of the approval, at 712. The patient can then be prompted to authorize the recommended changes to the dosage for their neuromodulation device, at 713. Once the patient approves the changes to the dosage for the neuromodulation device, the physician can then remotely administer or remotely cause administration of the dosage through the neuromodulation device, e.g., by adjusting settings and/or configurations of the neuromodulation device remotely through the patient's connected IoT device, at 714. The patient is then monitored to determine if there are any adverse reactions to the new dosage and/or to determine if the new dosage is correct based on patient feedback, at 715. Once it is determined that, at least after a predetermined time period within which no negative symptomatic or pain threshold/pain tolerance feedback is received, the process 700 can be terminated for the time being while the patient is continuously monitored by the smart bandage and/or other components of the system, at 716.

FIG. 8 is a block flow diagram of a method 800 comprising disposing a pain management device onto a portion of a patient's epidermis, the pain management device configured to provide an initial dosage of a pain management treatment, according to an initial prescription, via the patient's epidermis, at 801. The method 800 can further comprise monitoring patient behavior to determine a current pain tolerance for the patient, at 802. The method 800 can further comprise determining, based at least on the current pain tolerance, an updated prescription for an updated dosage different from the initial dosage of the pain management treatment, at 803. The method 800 can, optionally, further comprise comparing the updated prescription to a dynamic prescription comprising a dynamic preauthorized dosage range and determine whether the updated dosage is within the dynamic preauthorized dosage range, at 804. The method 800 can, optionally, further comprise, in an instance in which the updated dosage information is within the dynamic preauthorized range, providing to the prescription management unit a message authorizing the updated prescription, at 805. The method 800 can, optionally, further comprise, in an instance in which the updated dosage information is not within the dynamic preauthorized range and the prescription authorization unit has instructions to solicit manual authorization from a medical provider, displaying for the medical provider the updated prescription, receiving from the medical provider a response regarding the updated prescription, and providing to the prescription management unit one of a message confirming receipt of the updated prescription, a message authorizing the updated prescription, a message amending the updated prescription, a message replacing the updated prescription with a further updated prescription, and a message rejecting the updated prescription, at 806. The method 800 can, optionally, further comprise, in an instance in which the updated dosage information is not within the dynamic preauthorized range and the prescription authorization unit does not have instructions to solicit manual authorization from the medical provider, providing to the prescription management unit a message rejecting the updated prescription, at 807.

FIG. 9 is a block flow diagram of a method 900 comprising disposing a pain management device onto a portion of a patient's epidermis, the pain management device configured to provide an initial dosage of a pain management treatment, according to an initial prescription, via the patient's epidermis, at 901. The method 900 can further comprise monitoring patient behavior to determine a current pain tolerance for the patient, at 902. The method 900 can further comprise determining, based at least on the current pain tolerance, an updated prescription for an updated dosage different from the initial dosage of the pain management treatment, at 903. The method 900 can further comprise, in an instance in which the current pain tolerance greater than or less than a previous pain tolerance by a predefined margin, request or provide patient healthcare information, such as a care plan, case management data, electronic medical records, electronic health records, or the like, at 904. The method 900 can further comprise determining, based at least on the current pain tolerance and the patient healthcare information, an updated prescription for an updated dosage different from the initial dosage of the pain management treatment, at 905. The method 900 can further comprise comparing the updated prescription to a dynamic prescription comprising a dynamic preauthorized dosage range and determine whether the updated dosage is within the dynamic preauthorized dosage range, at 906. The method 900 can further comprise, in an instance in which the updated dosage is within a dynamic dosage range previously authorized in the dynamic prescription, automatically authorizing the pain management device to provide the pain management treatment according to the updated prescription, at 907. The method 900 can further comprise, in an instance in which the updated dosage is outside the dynamic dosage range previously authorized in the dynamic prescription, notifying a healthcare provider and/or requesting authorization for the updated prescription from the healthcare provider, at 908.

To summarize, embodiments of the present invention provide methods, apparatus, systems, computing devices, computing entities, and/or the like for administering pain management solutions remotely. Certain embodiments utilize systems, methods, and computer program products that provide pain management remotely, according to a dynamic prescription. In some embodiments, the dynamic prescription provides for changes in a dosage of a medication or electrical stimulation, based for instance upon changes in the patient's pain tolerance level, biological indicators, or behavioral characteristics. In some embodiments, if it is determined that a dosage change is needed, the dosage change can be compared against the dynamic prescription to determine whether the dosage change is permitted within the scope of the dynamic prescription. In some embodiments, if the dosage change is determined to be outside what is permitted by the scope of the dynamic prescription, the updated dosage information can be provided to the patient's physician for authorization of the updated dosage. In some embodiments, the patient's pain tolerance level, biological indicators, or behavioral characteristics may be provided to the patient's physician along with the updated dosage information in order for the physician to determine if the updated dosage is warranted.

In accordance with a first aspect, a system can be provided for carrying out dynamic pain management remotely. In some embodiments, the system can comprise: an epidermal treatment device configured to be placed in operable contact with a patient's epidermis and provide an initial dosage of a pain management treatment to the patient's epidermis according to an initial prescription; and a prescription management unit in wireless communication with the transdermal patch, the prescription management unit configured to: receive patient behavior information, determine, based at least upon the patient behavior information, the patient's current pain tolerance, and determine, based on at least the patient's current pain tolerance, an updated prescription comprising updated dosage information for pain management treatment. In some embodiments, the prescription management unit is further configured to provide the updated prescription to the epidermal treatment device, wherein the epidermal treatment device is further configured, upon receiving the updated prescription from the prescription management unit, to provide an updated dosage different from the initial dosage of the pain management treatment to the patient's epidermis according to the updated prescription. In some embodiments, the system can further comprise: a patient monitoring unit configured to monitor one or more biometric characteristics of the patient, generate the patient behavior information, and provide the patient behavior information to the prescription management unit. In some embodiments, the one or more biometric characteristics are selected from among posture, gait, speech patterns, eye movements, heart rate, blood pressure, core temperature, epidermal temperature, respiration rate, epidermal perspiration rate, facial expressions, changes in facial expressions, and Prkachin and Solomon Pain Intensity (PSPI) indicators. In some embodiments, the patient behavior information is generated based at least upon the one or more biometric characteristics and at least one of: manual inputs from the patient regarding the patient's current pain level, the patient's medical records, the dosage information from the initial prescription, and the patient's historical prescription information. In some embodiments, the system can further comprise: a prescription authorization unit in wireless communication with the prescription management unit, the prescription management unit being further configured to communicate wirelessly to the prescription authorization unit at least one of: the patient behavior information, the patient's pain tolerance, the updated prescription, and the updated dosage information for pain management treatment.

In some embodiments, the prescription authorization unit can be configured to: compare the updated prescription to a dynamic prescription comprising a dynamic preauthorized dosage range, and determine whether the updated dosage is within the dynamic preauthorized dosage range. In some embodiments, the prescription authorization unit can be further configured to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription, receive from the medical provider a response regarding the updated prescription, and provide to the prescription management unit one of a message confirming receipt of the updated prescription, a message authorizing the updated prescription, a message amending the updated prescription, a message replacing the updated prescription with a further updated prescription, and a message rejecting the updated prescription; or, in an instance in which the updated dosage information is not within the dynamic preauthorized range and the prescription authorization unit does not have instructions to solicit manual authorization from the medical provider, provide to the prescription management unit a message rejecting the updated prescription. In some embodiments, the epidermal treatment device comprises one or more of a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, and a intrathecal drug delivery device.

In accordance with a second aspect, a method is provided. In one embodiment, the method comprises: disposing a pain management device onto a portion of a patient's epidermis, the pain management device configured to provide an initial dosage of a pain management treatment, according to an initial prescription, via the patient's epidermis; monitoring patient behavior to determine a current pain tolerance for the patient; and determining, based at least on the current pain tolerance, an updated prescription for an updated dosage different from the initial dosage of the pain management treatment. In some embodiments, the method can further comprise communicating with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the method can further comprise, in an instance in which the updated dosage information is within the dynamic preauthorized range, providing to the prescription management unit a message authorizing the updated prescription, in an instance in which the updated dosage information is not within the dynamic preauthorized range and the prescription authorization unit has instructions to solicit manual authorization from a medical provider, displaying for the medical provider the updated prescription, receiving from the medical provider a response regarding the updated prescription, and providing to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, providing to the prescription management unit a message rejecting the updated prescription.

In accordance with a third aspect, a computer program product is provided. The computer program product may comprise at least one computer-readable storage medium having computer-readable program code portions stored therein, the computer-readable program code portions comprising executable portions configured to: communicate with a pain management device disposed on a portion of a patient's epidermis, the pain management device configured to provide an initial dosage of a pain management treatment, according to an initial prescription, via the patient's epidermis; monitor patient behavior to determine a current pain tolerance for the patient and determine, based at least on the current pain tolerance, an updated prescription for an updated dosage different from the initial dosage of the pain management treatment. In some embodiments, the computer-readable program code portions can further comprise executable portions configured to: communicate with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the computer-readable program code portions can further comprise executable portions configured to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription; receive from the medical provider a response regarding the updated prescription; and provide to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, provide to the prescription management unit a message rejecting the updated prescription.

In accordance with a fourth aspect, an apparatus comprising at least one processor and at least one memory including computer program code is provided. In one embodiment, the at least one memory and the computer program code may be configured to, with the processor, cause the apparatus to: communicate with a pain management device disposed on a portion of a patient's epidermis, the pain management device configured to provide an initial dosage of a pain management treatment, according to an initial prescription, via the patient's epidermis; monitor patient behavior to determine a current pain tolerance for the patient and determine, based at least on the current pain tolerance, an updated prescription for an updated dosage different from the initial dosage of the pain management treatment. In some embodiments, the at least one memory and the computer program code may be configured to, with the processor, cause the apparatus to: communicate with a prescription authorization unit regarding at least one of: the patient behavior, the patient's current pain tolerance, the updated prescription, and the updated dosage information for pain management treatment, wherein the prescription authorization unit is configured to compare the updated prescription to a dynamic prescription comprising a dynamic preauthorized dosage range and determine whether the updated dosage is within the dynamic preauthorized dosage range. In some embodiments, the at least one memory and the computer program code may be configured to, with the processor, cause the apparatus to: in an instance in which the updated dosage information is within the dynamic preauthorized range, provide to the prescription management unit a message authorizing the updated prescription; in an instance in which the updated dosage information is not within the dynamic preauthorized range and the prescription authorization unit has instructions to solicit manual authorization from a medical provider, display for the medical provider the updated prescription; receive from the medical provider a response regarding the updated prescription; and provide to the prescription management unit one of a message confirming receipt of the updated prescription, a message authorizing the updated prescription, a message amending the updated prescription, a message replacing the updated prescription with a further updated prescription, and a message rejecting the updated prescription, or, in an instance in which the updated dosage information is not within the dynamic preauthorized range and the prescription authorization unit does not have instructions to solicit manual authorization from the medical provider, provide to the prescription management unit a message rejecting the updated prescription.

In accordance with a fifth aspect, an apparatus can comprise at least one processor and at least one memory including computer program code. In some embodiments, the apparatus can be configured to carry out dynamic pain management remotely. In some embodiments, the apparatus can comprise: an epidermal treatment device configured to be placed in operable contact with a patient's epidermis and provide an initial dosage of a pain management treatment to the patient's epidermis according to an initial prescription, wherein the apparatus is configured to: receive patient behavior information, determine, based at least upon the patient behavior information, the patient's current pain tolerance, and determine, based on at least the patient's current pain tolerance, an updated dosage different from the initial dosage, according to an updated prescription, for pain management treatment. In some embodiments, the apparatus can be further configured to: provide, via the epidermal treatment device, an updated dosage different from the initial dosage of the pain management treatment to the patient's epidermis according to the updated prescription. In some embodiments, the apparatus is further configured to receive the patient behavior information from a patient monitoring unit configured to monitor one or more biometric characteristics of the patient and generate the patient behavior information. In some embodiments, the one or more biometric characteristics are selected from among posture, gait, speech patterns, eye movements, heart rate, blood pressure, core temperature, epidermal temperature, respiration rate, epidermal perspiration rate, facial expressions, changes in facial expressions, and Prkachin and Solomon Pain Intensity (PSPI) indicators. In some embodiments, the patient behavior information is generated based at least upon the one or more biometric characteristics and at least one of: manual inputs from the patient regarding the patient's current pain level, the patient's medical records, the dosage information from the initial prescription, and the patient's historical prescription information. In some embodiments, the apparatus can be further configured to: communicate wirelessly, to a prescription authorization unit, at least one of the patient behavior information, the patient's pain tolerance, the updated prescription, and the updated dosage information for pain management treatment. In some embodiments, the apparatus can be further configured to: receive, from the prescription authorization unit, one or more of a message confirming receipt of the updated prescription, a message approving the updated prescription, a message amending the updated prescription, a message replacing the updated prescription with a further updated prescription, and a message rejecting the updated prescription. In some embodiments, the epidermal treatment device comprises one or more of a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, and a intrathecal drug delivery device.

In accordance with a sixth aspect, there is provided a system for administering a pain management treatment remotely. The system can comprise an epidermal treatment device configured to store an initial prescription and operable to provide a pain management treatment to a patient (e.g., a user). In some embodiments, the epidermal treatment device can be coupled to the user, abutted to the user, embedded in the user's skin, implanted in the user, removably coupled to the user, or in any other manner caused to provide a pain management treatment to the patient when the patient is not with their provider (e.g., configured to administer the pain management treatment remotely). The system can further comprise a patient monitoring unit configured to iteratively, discretely, or continuously, observe the user and measure, monitor, estimate, calculate, interpolate, or otherwise determine biometric characteristics about the user.

The system can further comprise a prescription management unit that is in operable communication with the patient monitoring unit, the prescription management unit being configured to review the user's biometric characteristics and to determine whether the initial prescription is sufficient to reduce or eliminate the user's pain based on the user's pain tolerance or pain threshold, which is determined based on at least the biometric characteristics. The prescription management unit can also be configured to determine when a change in the initial prescription dosage is necessary based on changes in the user's biometric characteristics. In an instance in which the prescription management unit determines that a change in the dosage of the pain management treatment is needed, based at least upon the user's biometric characteristics, the prescription management unit can a) determine that the change in dosage of the pain management treatment is automatically approved based upon some initial instructions regarding a change tolerance or margin about the initial dosage that the prescription management unit is instructed to automatically authorize, b) determine that the dosage change is an errant dosage change based upon the magnitude of the change relative to the dosage of the initial prescription and request further biometric characteristics be provided from the patient monitoring unit, or c) determine that the change in dosage of pain management treatment is needed but that it falls outside of any provided change tolerance or margin relative to the initial dosage, and request authorization for the updated dosage from a provider or a provider device. With regard to option c) from above, the system can further comprise a prescription authorization unit configured to store or receive a dynamic prescription associated with the user and with the particular pain management treatment. The dynamic prescription can be developed based upon provider-provided and/or patient-provided data such as electronic health records, individual health records, international or domestic health regulations, provider management systems, patient preferences, the patient's insurance details, the patient's historical biometric data, historical biological data, historical medical records, and the like. The dynamic prescription can comprise a set of 'if/then' elements or the like that the prescription authorization unit is configured to answer in a particular order. In some embodiments, the dynamic prescription can include an initial question or initial set of questions that relate, for instance, to a change in the patient's pain tolerance or pain threshold. In some embodiments, the dynamic prescription can include subsequent questions or set of questions that relate, for instance, to a provider-provide limit on the dosage of the pain management treatment that considers the patient's biometric, biological, medical, or other characteristics or data (e.g., the patient's heart rate, blood pressure, gait, or the like). In some embodiments, the dynamic prescription can also include a question or a set of questions related to domestic or international regulations related to what and how much pain management treatments can be administered/changed remotely, absolute or relative dosage limits, and/or the like. In some embodiments, the dynamic prescription can include a question or a set of questions related to past changes in the dosage, the rate and magnitude of such changes, the remaining supply of pain medication (when applicable), and/or the like. Said otherwise, the dynamic prescription, instead of providing a static dosage, can provide a dosage range that changes in response to changes in a patient's pain tolerance or pain threshold, accounting for medical or legal limits placed on dosage changes that are specific to the pain management treatment, jurisdiction, provider, application type, patient, provider, and/or the like. The dynamic prescription can be pre-authorized by the provider. In some embodiments, when the prescription management unit determines that the change in dosage of pain management treatment is needed but that it falls outside of any provided change tolerance or margin relative to the initial dosage, the prescription management unit may transmit a request for authorization of the updated dosage of the updated prescription to the prescription authorization unit. The prescription authorization unit can then review the request for the updated dosage of the updated prescription, e.g., by answering the questions related to the dynamic prescription to determine if the provider-pre-authorized dynamic prescription authorizes the updated dosage for the patient, and then a) automatically provides authorization for the updated prescription to the prescription management unit, b) automatically rejects the updated prescription (e.g., when the dosage change is suspected to be in error, when the dosage change would contravene a law, and/or the like), or c) requests approval for the updated prescription from the provider. In some embodiments, the prescription authorization unit can cause a notification, alert, message, request, or the like to be pushed to, displayed on, sent to, or otherwise provided to a provider device such as a computer, beeper, mobile phone, smart phone, tablet, or the like. The provider can then review the updated prescription and can instruct the prescription authorization unit to either allow or disallow the updated prescription, can mark the updated prescription as being a suspected errant request, can communicate with the patient/user to provide telemedical care or request that the patient/user visits the provider's office, amend the dynamic prescription based upon the updated prescription request, and/or the like. In an instance in which the prescription authorization unit or prescription management unit automatically authorizes the updated prescription, or in an instance in which the provider manually authorizes the updated prescription, the prescription management unit can communicate with either the patient monitoring unit or the epidermal treatment device to provide the updated prescription along with authorization for the epidermal treatment device to administer the pain management treatment to the user according to the updated prescription. The epidermal treatment device can then replace the initial prescription with the updated prescription and comply with the specific dosage/timing requirements of the updated prescription in administering the pain management treatment to the user.

In accordance with a seventh aspect, there is provided an apparatus for accurately determining a pain tolerance or a pain threshold for a patient remotely. The apparatus can comprise one or more processors and one or more memory storing computer program code. The apparatus can be configured to iteratively, discretely, or continuously, observe the user and measure, monitor, estimate, calculate, interpolate, or otherwise determine biometric, biological, medical, or other suitable characteristics about the patient. The apparatus can determine the patient's current pain tolerance or pain threshold based on at least the biometric, biological, medical, or other suitable characteristics. The apparatus can comprise a display and a user interface configured to allow for the patient to interact with an application, program, browser, or the like stored on and/or hosted by the apparatus. In some embodiments, the patient may provide feedback about their current pain tolerance or pain threshold at certain intervals, e.g., regularly, irregularly, when they perceive a change in their pain tolerance or pain threshold, and/or the like. In some embodiments, the apparatus can include one or more sensors, one or more camera devices, one or more keyboards, one or more touchscreens or other such interactive input devices, and/or the like. In some embodiments, the apparatus can include one or more activity monitoring devices or healthcare monitoring devices, such as but not limited to: a gyroscope, a magnetometer, an accelerometer (e.g., a 3-axis accelerometer), a geospatial positioning system, a barometer, an altimeter, a step counter, a blood pressure monitor, a heart rate monitor, a respiration monitor, ambient pressure sensor, ambient temperature sensor, ambient oxygen sensor, an electrocardiogram device, an electroencephalogram device, skin temperature sensor, a myocardial sensor, a blood oxygen sensor, a elastomeric plethysmography (EP) device (e.g., one or more piezoelectric sensors on an elastic band for elastomeric plethysmography via current variation), an impedance plethysmography (IP) device, a respiratory inductive plethysmography (RIP) device, a photoplethysmography (PPG) device configured to measure blood oxygen saturation using pulse oximetry principles by measuring two adjacent peaks in a blood vessel variation waveform, a continuous glucose monitoring (CGM) device, or the like. In some embodiments, the apparatus can include one or more speakers and/or one or more microphones. In some embodiments, the apparatus is configured to monitor, measure, calculate, estimate, sense, observe, interpret, derive, or otherwise determine one or more biometric, biological, medical, or movement characteristics of the patient and the chance over time thereof, such as but not limited to: facial feature, facial expressions, facial micro-expressions, gait, heart rate, heart rate variability, heart rate irregularity, incidents of a fall experienced by the patient, step count, step pace, blood pressure, respiration rate, eye movements, blink rate, pupil dilation, vocal/speech pattern, speech pace, incidents of slurred speech, posture, perspiration rate, breathing rate, sudden reduction or loss of hearing (e.g., if a patient suddenly increases the speaker volume on the apparatus when interacting with the apparatus), dermal and subdermal perfusion rates, time spent sitting versus standing, limb and trunk movement and range of motion, sleep duration and sleep type patterns, combinations thereof, and/or the like. For instance, the apparatus can capture a patient's facial expressions when they are using the device, e.g., by using the front facing camera on a smart phone, and implement a facial action coding system (FACS) in conjunction with Prkachin Solomon Pain Intensity (PSPI) analysis to track pain tolerance or pain threshold changes in the patient. The apparatus can use an algorithm, neural network, machine learning model, and/or the like to determine changes in the patient's pain tolerance or pain threshold.

In accordance with an eighth aspect, there is provided a method for preparing a dynamic prescription of a pain management treatment for a patient. In some embodiment, the method can comprise determining the internet-of-things (IoT) devices and sensors available for a patient and the device and sensor boundaries with respect to particular biological indicators or characteristics. The method can further comprise establishing the patient's current pain threshold/pain tolerance and associating the patient's current pain threshold/pain tolerance with the patient's particular biological indicators or characteristics. The method can further comprise determining a current dosage of a pain management treatment being administered to the patient and associating the current dosage of the pain management treatment with the patient's current pain threshold/pain tolerance and the patient's particular biological indicators or characteristics. The method can further comprise receiving, from a provider, an outside dosage range indicating a magnitude of increase of the dosage and a magnitude of decrease of the dosage that are allowed for the patient. The method can further comprise receiving, from the provider, a set of conditions in which the current dosage of the pain management treatment can be changed, within the outside dosage range. As an initial non-limiting example, the provider may indicate that if the patient's pain tolerance increases to above 9/10 AND the patient belongs to a certain demographic area AND if the patient's age is within a particular age range, then the current dosage can be increased to an updated dosage higher than the current dosage for a particular time period, e.g., before re-analyzing patient pain tolerance/pain threshold or reverting back to the current dosage lower than the updated dosage. As a subsequent non-limiting example, the provider may indicate that if the patients pain tolerance/pain threshold reduces by more than a threshold reduction in pain tolerance/pain threshold AND the patient belongs to a certain demographic area OR if a particular biological indicator is within a predetermined range considered to be suitable for a reduction in dosage, then the current dosage can be decreased to an updated dosage lower than the current dosage for a particular time period, e.g., before re-analyzing patient pain tolerance/pain threshold or reverting back to the current dosage higher than the updated dosage. As a further non-limiting example, the patient may have a wearable device that sends a signal to a provider management system; for example, a cardiology patient taking statins that is determined to be involved in excessive/out-of-normal physical activity, causing a reduction in blood sugar level, which may necessitate a reduction in the dosage of a remotely administered diabetes medication for a particular time period. As yet another non-limiting example, for an oncology patient, to whom a medication is being administered remotely according to any of the processes or methods described herein, a provider may code a dynamic prescription for the oncology patient that indicates, if the oncology patient is exposed to conditions that are not optimal in view of their medical condition and medication being administered AND/OR if the patient is in a particular demographic group (e.g., a particular sex, race, nationality, geographic location, employment type, or any other suitable group of patients) AND/OR if the patient has an age that is within a particular predetermined age range AND/OR if the patient received their last oncology treatment (e.g., radiation therapy, chemotherapy, and/or the like) within a predetermined window preceding the date and time of analysis, then the dynamic prescription can automatically instruct the patient, the provider, the patient's remote pain management treatment administration device (e.g., transdermal patch, neuromodulation device, and/or the like) to increase their dosage of the pain management treatment for a predetermined time period. In some embodiments, in order for a provider to "code" the dynamic prescription via digital means within a provider management system, there may be an "INPUT" which needs to be "ANALYZED" before coding the prescription. For example, an "INPUT" may include without limitation one or more of (a) information related to the sensors or IoT devices that the patient has registered and/or that are in communication with the apparatus or system carrying out the method of establishing the dynamic prescription, (b) capabilities and configurations for the various sensors or IoT devices, either derived from the respective sensor/IoT device, culled from the above-mentioned information, or provided by or retrieved from a third party, (c) a summary of edge computing capabilities for each IoT device, (d) capabilities and configurations for each "coordinating device," such as a smart watch, smart home sensor, vehicle sensor, or the like, that coordinates multiple IoT devices, (e) hierarchy of sensors/IoT devices with regard to channels of communication and the configurations required for data collation and transmission from each of these devices, (f) information related to the interoperability of the various sensors/IoT devices the patient has registered, (g) information related to alternative hierarchies or channels of communication if one or more of the sensors/IoT devices that the patient has registered becomes unreachable or is suspected of being corrupted or providing erroneous data, and/or (h) other suitable information helpful or necessary for the establishment of a stable channel of communication between and within the network and the sensors/IoT devices such that the dynamic prescription can be generated and/or updated based upon inputs from the provider as well as feedback and data provided by the patient and the various sensors/IoT devices. The method for initial coding of the dynamic prescription, in addition to or alternative to the approach and process elements described above, can include presenting the provider with the available "INPUTS," allowing the provider to choose the appropriate collection of sensors/IoT devices that are appropriate for considering with regard to the dynamic prescription. The provider can then indicate or code in the dynamic prescription (which may for instance be carried out by selecting among a drop-down list or conducting a search) the appropriate biological indicators, patient movement data, healthcare metrics, and/or environmental data that should be considered from among the data received from the collection of approved sensors/IoT devices the patient has registered. The provider can then identify, for each sensor or IoT device and/or for each type of feedback or data, the expected range or value, optionally one or more secondary indicators or considerations that should be considered in such an instance, and a dosage change that should be carried out in such an instance. For example, for a patient's heart rate monitor, the provider can code a particular heart rate range that is expected for the patient, such that when the heart rate monitor returns a heart rate outside the provider-indicated expected range of heart rates, the dynamic prescription can increase or decrease the dosage based on such an indication. When coding the dynamic prescription, the provider may select a particular frequency or a particular time frame and iteration count for any or all of the analyses being done remotely to determine the patient's pain tolerance or pain threshold, and/or can indicate how the dosage should change based upon changes in the respective analyses. The provider may also indicate the duration of pain management treatment and/or can indicate one or more stages of pain management treatment (e.g., through a staged weaning period). When coding the dynamic prescription, the provider may select a particular activity or group of activities to indicate how the prescription changes based on a particular input, such as information related to the initial cause of pain, the intensiveness of any preceding surgeries or inpatient/outpatient treatments, how many calories the patient has consumed, the number of stiches the patient received following a surgery, or any other suitable input. When coding the dynamic prescription, the provider may select one or more user contexts, such as the demographic information of the patient, to consider when dynamically changing the prescription. When coding the dynamic prescription, the provider may select one or more environmental conditions or changes to consider when dynamically changing the prescription, such environmental conditions or changes including but not limited to exposure to contaminants or harsh environmental conditions, the frequency and/or type of human interaction the patient has (e.g., by tracking emails, SMS texts, phone calls, or the like for a period of time following a surgery), the patient's social media accounts and their interactions with others on these social media platforms, application programming interface (API) calls to the weather system or a third-party weather service, temperature sensor readings, barometric pressure sensor readings, patient activity/motion data, and/or the like. When coding the dynamic prescription, the provider may select a prescription renewal time, e.g., by analyzing the consumption rate of the drug, and authorize the dynamic prescription and/or associated machine learning algorithm or artificial intelligence program carrying out the dynamic prescription to suggest changes or pre-authorize changes only at particular times or with a consideration for the remaining stock of a drug that the patient has on hand. In some embodiments, when the dynamic prescription is updated and/or when their effective dosage is changed according to the dynamic prescription, the patient may be notified through push notification from an application, email, phone call, SMS text message, or the like regarding the change in their prescription or effective dosage. In some embodiments, when the dynamic prescription is updated and/or when their effective dosage is changed according to the dynamic prescription, the patient may be asked to authorize the change in their prescription or effective dosage. In some embodiments, when the dynamic prescription is updated and/or when their effective dosage is changed according to the dynamic prescription, the patient may be notified regarding the change in their prescription or effective dosage and given an opportunity to temporarily stop the change in their prescription or effective dosage until the provider has reviewed the change and has authorized the change. In some embodiments, the patient may be notified regarding the change in their prescription or effective dosage only when the dynamic prescription and/or associated machine learning algorithm or artificial intelligence program carrying out the dynamic prescription determines that the calculated necessary dosage change is outside the range preauthorized under the dynamic prescription, elevated the request for a dosage change to the provider, and the provider has authorized a change not only to the dosage but also to the dynamic prescription. In some embodiments, the dynamic prescription and/or associated machine learning algorithm or artificial intelligence program carrying out the dynamic prescription can track and/or request updates from the patient's sensors/IoT devices regarding the quantity of a remaining stock of the patient's medication. In some embodiments, in an instance in which the dynamic prescription and/or associated machine learning algorithm or artificial intelligence program carrying out the dynamic prescription determine that a change in the dosage will unduly diminish the quantity of the remaining stock of the patient's medication, and/or will result in a depletion of the patient's medication before such a time as the patient is scheduled (or legally allowed) to replenish their stock of the medication, can take these competing challenges and interests into account when determining a necessary change in the dosage of the patient's medication and/or can disallow changes to the dosage administered in order to maintain sufficient stock so that the patient does not run out of their medication before they receive a replenishing supply. In some embodiments, the dynamic prescription and/or associated machine learning algorithm or artificial intelligence program carrying out the dynamic prescription, upon determining that the patient's stock of a medication is low or that a change made to their dosage will result in a more rapid diminishment of the patient's stock of the medication, can provide an alert to the provider such that the provider can coordinate providing the patient with a replenishing supply of their medication, amend the patient's plan of care with regard to the time horizon for administering the drug, contravene the dosage change, and/or contact the patient for follow-up telemedical care.

CONCLUSION

To provide an overall understanding, certain illustrative embodiments have been described; however, it will be understood by one of ordinary skill in the art that systems, apparatuses, and methods described herein can be adapted and modified to provide systems, apparatuses, and methods for other suitable applications and that other additions and modifications can be made without departing from the scope of systems, apparatuses, and methods described herein.

The embodiments described herein have been particularly shown and described, but it will be understood that various changes in form and details may be made. Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems, apparatuses, or methods of the present disclosure.

Conventional terms in the fields of pain management, IoT devices, medical devices, transdermal patches, neuromodulation devices, artificial intelligence, and machine learning have been used herein. The terms are known in the art and are provided only as a non-limiting example for convenience purposes. Accordingly, the interpretation of the corresponding terms in the claims, unless stated otherwise, is not limited to any particular definition. Thus, the terms used in the claims should be given their broadest reasonable interpretation.

Although specific embodiments have been illustrated and described herein, it will be appreciated by those of ordinary skill in the art that any arrangement that is adapted to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," and/or the like are used merely as labels, and are not intended to impose numerical requirements or any relative order of operations or organization on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure and is submitted with the understanding that it will not be used to interpret or limit the scope or meaning of the claims.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

What is claimed is:

1. A system for dynamic pain management, the system comprising:
   one or more processors communicatively coupled to an epidermal treatment device that is configured to abe placed in operable contact with an epidermis of a patient and (ii) provide an initial dosage of a pain management treatment to the patient via a portion of the epidermis of the patient,
   wherein the one or more processors are configured to:
      receive, during or after the initial dosage of the pain management treatment is provided to the patient using the epidermal treatment device, patient behavior information;
      determine, based at least in part on the patient behavior information, a current pain tolerance of the patient;
      determine, based at least in part on the current pain tolerance of the patient, an updated dosage for the pain management treatment; and
      in an instance in which the updated dosage of the pain management treatment is allowed to be provided to the patient in accordance with a dynamic prescription for the pain management treatment associated with the patient, cause reconfiguration of the epidermal treatment device to provide the updated dosage of the pain management treatment to the patient via the portion of the epidermis of the patient in contact with the epidermal treatment device.

2. The system of claim 1, wherein the system is further configured to:
   in an instance in which the updated dosage of the pain management treatment is not allowed to be provided to the patient in accordance with the dynamic prescription for the pain management treatment associated with the patient, send a request for an updated dynamic prescription, the request comprising one or more of: the updated dosage, the patient behavior information, or information about the current pain tolerance of the patient.

3. The system of claim 1, wherein the system is further configured to:
   receive, from a patient monitoring device configured to monitor one or more biometric characteristics of the patient, the patient behavior information.

4. The system of claim 3, wherein the one or more biometric characteristics are selected from among: posture, gait, speech patterns, eye movements, heart rate, blood pressure, core temperature, epidermal temperature, respiration rate, epidermal perspiration rate, facial expressions, changes in facial expressions, or Prkachin and Solomon Pain Intensity (PSPI) indicators.

5. The system of claim 4, wherein the patient behavior information is generated based at least in part on the one or more biometric characteristics and one or more of: manual inputs from the patient regarding the patient's current pain level, medical records of the patient, initial dosage information, information from the dynamic prescription, or historical pain management treatment information for the patient.

6. The system of claim 5, wherein the system is further configured to:
   provide, to a prescription authorization device at least one of the patient behavior information, information about the current pain tolerance of the patient, information about the initial dosage, and or information about the updated dosage of the pain management treatment.

7. The system of claim 6, wherein the system is further configured to:
   receive, from the prescription authorization device one or more of: a message providing the updated prescription, a message providing a further updated prescription indicating another dosage of the pain management treatment that is different from the updated dosage for the pain management treatment, or a message indicating that the updated dosage of the pain management treatment is not authorized for the patient.

8. The system of claim 1, wherein the epidermal treatment device comprises one or more of: a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, or a intrathecal drug delivery device.

9. A system for dynamic pain management, the system comprising:
   an epidermal treatment device configured to be (i) placed in operable contact with an epidermis of a patient and (ii) provide an initial dosage of a pain management treatment to the patient via a portion of the epidermis of the patient; and
   one or more processors communicatively coupled to the epidermal treatment device, the one or more processors being configured to:
      receive or generate a dynamic prescription for the pain management treatment;
      receive patient behavior information;
      determine, based at least in part on the patient behavior information, a current pain tolerance of the patient;
      determine, based at least in part on the current pain tolerance of the patient, updated dosage information for an updated dosage of the pain management treatment;
      determine whether the updated dosage of the pain management treatment is allowed based on the dynamic prescription for the pain management treatment, and if the updated dosage is allowed based on the dynamic prescription for the pain management treatment, cause the epidermal treatment device to provide the updated dosage of the pain management treatment to the epidermis of the patient according to the updated dosage information.

10. The system of claim 9,
wherein the
updated dosage of the pain management treatment is different from the initial dosage of the pain management treatment.

11. The system of claim 9, further comprising:
a patient monitoring device configured to monitor one or more biometric characteristics of the patient, generate the patient behavior information, and provide the patient behavior information to the one or more processors.

12. The system of claim 11, wherein the one or more biometric characteristics are selected from among: posture, gait, speech patterns, eye movements, heart rate, blood pressure, core temperature, epidermal temperature, respiration rate, epidermal perspiration rate, facial expressions, changes in facial expressions, or Prkachin and Solomon Pain Intensity (PSPI) indicators.

13. The system of claim 12, wherein the patient behavior information is generated based at least in part on the one or more biometric characteristics and one or more of: manual inputs from the patient regarding a current pain level of the patient, medical records of the patient, initial dosage information from the dynamic prescription, or historical prescription information of the patient.

14. The system of claim 13, further comprising:
a prescription authorization device communicatively coupled to the one or more processors, the one or more processors being further configured to provide, to the prescription authorization device, one or more of: the patient behavior information, the current pain tolerance, or the updated dosage information for the pain management treatment.

15. The system of claim 14, wherein the prescription authorization device is further configured to:
compare the updated dosage to one or more dynamic preauthorized dosage ranges from the dynamic prescription for the pain management treatment, and
determine whether the updated dosage is within at least one of the one or more dynamic preauthorized dosage ranges from the dynamic prescription.

16. The system of claim 15, wherein the prescription authorization device is further configured to:
in an instance in which the updated dosage is within at least one of the one or more dynamic preauthorized dosage ranges of the dynamic prescription for the pain management treatment, provide a message to the one or more processors authorizing the updated dosage of the pain management treatment;
in an instance in which the updated dosage is not within at least one of the one or more dynamic preauthorized dosage ranges of the dynamic prescription for the pain management treatment and the prescription authorization device has instructions to solicit manual authorization from a medical provider:
cause display, to the medical provider, of information about the updated dosage of the pain management treatment,
receive an indication regarding a response from the medical provider; and
based on the indication regarding the response from the medical provider, provide to the one or more processors, one or more of: a message confirming receipt of the information about the updated dosage, a message authorizing the updated dosage, a message amending the dynamic prescription, a message replacing the dynamic prescription with an updated dynamic prescription, or a message rejecting the updated dosage; or
in an instance in which the updated dosage is not within at least one of the one or more dynamic preauthorized dosage ranges of the dynamic prescription for the pain management treatment and the prescription authorization device does not have instructions to solicit manual authorization from the medical provider, provide to the one or more processors a message rejecting the updated dosage of the pain management treatment for the patient.

17. The system of claim 9, wherein the epidermal treatment device comprises one or more of: a transdermal patch, a single-layer drug-in-adhesive patch, a multi-layer drug-in-adhesive patch, a reservoir transdermal patch, a matrix adhesive patch, a vapor patch, a neuromodulation device, a repetitive transcranial magnetic stimulation device, a transcranial pulsed electromagnetic fields device a transcutaneous electrical nerve stimulation device, an electroconvulsive therapy device, ora intrathecal drug delivery device.

18. A method comprising:
configuring, using one or more processors, a pain management device to provide an initial dosage of a pain management treatment to a portion of an epidermis of a patient, wherein the initial dosage is determined from a dynamic prescription indicating one or more allowable dosage ranges of the pain management treatment for the patient;
determining, based at least upon patient behavior, a current pain tolerance for the patient;
determining, based at least on the current pain tolerance for the patient, an updated dosage of the pain management treatment;
in an instance in which the updated dosage is within an allowable dosage range of the one or more allowable dosage ranges of the pain management treatment indicated in the dynamic prescription for the patient, reconfiguring, using the one or more processors, the pain management device to provide the updated dosage of the pain management treatment to the portion of the epidermis of the patient; and
in an instance in which the updated dosage is outside the one or more allowable dosage ranges of the pain management treatment indicated in the dynamic prescription for the patient, sending a request for an updated dynamic prescription, wherein the request comprises at least one of: the patient behavior, the current pain tolerance for the patient, or the updated dosage of the pain management treatment desired for the patient.

19. The method of claim 18, wherein the request is provided to a prescription authorization device,
the prescription authorization device being configured to determine whether the updated dosage is within the one or more allowable dosage ranges of the pain management treatment indicated in the dynamic prescription for the patient.

20. The method of claim 19, further comprising:
in an instance in which the updated dosage is outside the one or more allowable dosage ranges of the pain management treatment indicated in the dynamic prescription for the patient and the prescription authorization device has instructions to solicit manual authorization of the updated dosage from a medical provider, causing display of information about the updated dosage to the medical provider, receiving a response indicating authorization or rejection of the updated dosage of the pain management treatment for the patient by the medical provider, and providing to the one or more processors one or more of: a message confirming receipt of the information about the updated dosage, a message authorizing the updated dosage of the pain management treatment, a message amending the dynamic prescription, a message replacing the updated_dosage with a further updated dosage, or a message rejecting the updated dosage; or in an instance in which the updated dosage is outside the one or more allowable dosage ranges of the pain management treatment indicated in the dynamic prescription for the patient and the prescription authorization device has no instructions to solicit manual authorization from the medical provider, providing to the one or more processors a message rejecting the updated dosage for the pain management treatment.

* * * * *

UNITED STATES PATENT AND TRADEMARK OFFICE
CERTIFICATE OF CORRECTION

PATENT NO. : 11,823,782 B2
APPLICATION NO. : 16/807674
DATED : November 21, 2023
INVENTOR(S) : Rama S. Ravindranathan et al.

It is certified that error appears in the above-identified patent and that said Letters Patent is hereby corrected as shown below:

In the Claims

In Column 73, Line 33, Claim 1, delete "to abe" an insert -- to (i) be --, therefor.

In Column 74, Lines 21-22, Claim 6, delete "device at least one of the" and insert -- device, at least one of: the --, therefor.

In Column 74, Line 28, Claim 7, delete "device one" and insert -- device, one --, therefor.

In Column 76, Line 27, Claim 17, delete "ora" and insert -- or a --, therefor.

In Column 77, Line 15, Claim 20, delete "updated_dosage" and insert -- updated dosage --, therefor.

Signed and Sealed this
Ninth Day of April, 2024

*Katherine Kelly Vidal*

Katherine Kelly Vidal
*Director of the United States Patent and Trademark Office*